US010279020B2

(12) United States Patent
Podack

(10) Patent No.: US 10,279,020 B2
(45) Date of Patent: May 7, 2019

(54) TUMOR VACCINE

(71) Applicant: University of Miami, Miami, FL (US)

(72) Inventor: Eckhard R. Podack, Coconut Grove, FL (US)

(73) Assignee: University of Miami, Miami, FL (US)

( * ) Notice: Subject to any disclaimer, the term of this patent is extended or adjusted under 35 U.S.C. 154(b) by 165 days.

(21) Appl. No.: 14/812,416

(22) Filed: Jul. 29, 2015

(65) Prior Publication Data

US 2016/0045583 A1   Feb. 18, 2016

Related U.S. Application Data

(63) Continuation of application No. 12/580,554, filed on Oct. 16, 2009, now abandoned, which is a continuation-in-part of application No. 10/950,157, filed on Sep. 24, 2004.

(60) Provisional application No. 61/106,355, filed on Oct. 17, 2008, provisional application No. 60/506,656, filed on Sep. 26, 2003.

(51) Int. Cl.
*A61K 39/00* (2006.01)

(52) U.S. Cl.
CPC .. *A61K 39/0011* (2013.01); *A61K 2039/5152* (2013.01); *A61K 2039/5156* (2013.01)

(58) Field of Classification Search
None
See application file for complete search history.

(56) References Cited

U.S. PATENT DOCUMENTS

| | | |
|---|---|---|
| 3,069,941 A | 12/1962 | Baubles |
| 5,030,621 A | 7/1991 | Bystryn |
| 5,858,776 A | 1/1999 | Ostrand-Rosenberg et al. |
| 5,861,310 A | 1/1999 | Freeman et al. |
| 6,039,941 A | 3/2000 | Blankenstein et al. |
| 6,228,357 B1 | 5/2001 | Maudsley |
| 6,294,660 B1 | 9/2001 | Sharpe et al. |
| 6,319,709 B1 | 11/2001 | Ostrand-Rosenberg et al. |
| 6,503,503 B1 | 1/2003 | Bigner et al. |
| 6,716,823 B1 | 4/2004 | Tang et al. |
| 6,723,705 B1 | 4/2004 | Freeman et al. |

FOREIGN PATENT DOCUMENTS

| | | |
|---|---|---|
| AU | 2004275814 | 4/2005 |
| CA | 2540283 | 4/2005 |
| EP | 1667701 | 2/2007 |
| WO | WO 2005030136 | 4/2005 |
| WO | WO 2005/030136 | 6/2005 |
| WO | WO 05049073 | 6/2005 |
| WO | WO 08027456 | 3/2008 |
| WO | WO 2010/045573 | 4/2010 |

OTHER PUBLICATIONS

Yamazaki et al. (Cancer Research, 1999, vol. 59, p. 4642-4650.*
Vabulas et al. (The Journal of Biological Chemistry, 2002, Vo;. 277, p. 20847-20853).*
Bixby et al. (International Journal of Cancer, 1998, vol. 78, pp. 685-694).*
"Chemotherapy in Non-Small Cell Lung Cancer: A Meta-Analysis Using Updated Data on Individual Patients From 52 Randomised Clinical Trials." *BMJ*. 311(1995): pp. 899-909.
"Clinical Practice Guidelines for the Treatment of Unresectable Non-Small-Cell Lung Cancer." *J. Clin. Oncol.* 15.8(1997): pp. 2996-3018.
Antonia et al. "Phase I Trial of a B7-1 (CD80) Gene Modified Autologous Tumor Cell Vaccine in Combination with Systemic Interleukin-2 in Patients with Metastatic Renal Cell Carcinoma." *J. Urol.* 167.5(2002): pp. 1995-2000.
ATCC Accession No. 256, retrieved from the internet on Oct. 28, 2011.
ATCC Accession No. 5800, retrieved from the internet on Oct. 28, 2011.
ATCC Accession No. 5803, retrieved from the internet on Oct. 28, 2011.
ATCC Accession No. 5807, retrieved from the internet on Oct. 28, 2011.
ATCC Accession No. 5810, retrieved from the Internet on Oct. 28, 2011.
ATCC Accession No. 5816, retrieved from the Internet on Oct. 28, 2011.
ATCC Accession No. 5818, retrieved from the internet on Oct. 28, 2011.
ATCC Accession No. 5834, retrieved from the Internet on Oct. 28, 2011.
ATCC Accession No. 5835, retrieved from the internet on Oct. 28, 2011.
ATCC Accession No. 5844, retrieved from the internet on Oct. 28, 2011.
ATCC Accession No. 5850, retrieved from the internet on Oct. 28, 2011.
ATCC Accession No. 5852, retrieved from the internet on Oct. 28, 2011.

(Continued)

*Primary Examiner* — Agnieszka Boesen
(74) *Attorney, Agent, or Firm* — Myers Bigel, P.A.

(57) ABSTRACT

The invention relates to the fields of medicine, immunology, and oncology. More specifically, the invention relates to methods and compositions for inducing an immune response against a tumor in an animal subject. The invention provides that a lung cancer cell or other tumor cells, genetically modified to express a nucleic acid encoding CD80 (B7.1) and a nucleic acid encoding an HLA antigen, and method for stimulating an immune response to a tumor with the tumor cell so genetically modified. The invention additionally provides a method of inhibiting a tumor, including a cancer such as lung cancer, by administering an allogeneic tumor cell, for example a cancer tumor cell such as a lung cancer tumor cell, genetically modified to express a nucleic acid encoding CD80 (B7.1) and a nucleic acid encoding an HLA antigen.

6 Claims, 9 Drawing Sheets

Specification includes a Sequence Listing.

(56) References Cited

OTHER PUBLICATIONS

ATCC Accession No. 5867, retrieved from the Internet on Oct. 28, 2011.
ATCC Accession No. 5870, retrieved from the internet on Oct. 28, 2011.
ATCC Accession No. 5872, retrieved from the Internet on Oct. 28, 2011.
ATCC Accession No. 5875, retrieved from the Internet on Oct. 28, 2011.
ATCC Accession No. 5876, retrieved from the internet on Oct. 28, 2011.
ATCC Accession No. 5878, retrieved from the internet on Oct. 28, 2011.
ATCC Accession No. 5881, retrieved from the Internet on Oct. 28, 2011.
ATCC Accession No. 5884, retrieved from the internet on Oct. 28, 2011.
ATCC Accession No. 5887, retrieved from the Internet on Oct. 28, 2011.
ATCC Accession No. 5889, retrieved from the Internet on Oct. 28, 2011.
ATCC Accession No. 5891, retrieved from the internet on Oct. 28, 2011.
ATCC Accession No. 5892, retrieved from the Internet on Oct. 28, 2011.
ATCC Accession No. 5893, retrieved from the internet on Oct. 28, 2011.
ATCC Accession No. 5896, retrieved from the internet on Oct. 28, 2011.
ATCC Accession No. 5899, retrieved from the internet on Oct. 28, 2011.
ATCC Accession No. 5900, retrieved from the internet on Oct. 28, 2011.
ATCC Accession No. 5904, retrieved from the Internet on Oct. 28, 2011.
ATCC Accession No. 5907, retrieved from the internet on Oct. 28, 2011.
ATCC Accession No. 5908, retrieved from the internet on Oct. 28, 2011.
ATCC Accession No. 5909, retrieved from the internet on Oct. 28, 2011.
ATCC Accession No. 5912, retrieved from the internet on Oct. 28, 2011.
ATCC Accession No. 5914, retrieved from the Internet on Oct. 28, 2011.
ATCC Accession No. 5918, retrieved from the Internet on Oct. 28, 2011.
ATCC Accession No. 5921, retrieved from the Internet on Oct. 28, 2011.
ATCC Accession No. 5922, retrieved from the Internet on Oct. 28, 2011.
ATCC Accession No. 5923, retrieved from the internet on Oct. 28, 2011.
ATCC Accession No. 5924, retrieved from the internet on Oct. 28, 2011.
ATCC Accession No. 5926, retrieved from the Internet on Oct. 28, 2011.
ATCC Accession No. 5930, retrieved from the internet on Oct. 28, 2011.
ATCC Accession No. 5935, retrieved from the internet on Oct. 28, 2011.
ATCC Accession No. 5939, retrieved from the internet on Oct. 28, 2011.
ATCC Accession No. 5941, retrieved from the internet on Oct. 28, 2011.
ATCC Accession No. 5942, retrieved from the internet on Oct. 28, 2011.
ATCC Accession No. 5944, retrieved from the internet on Oct. 28, 2011.
ATCC Accession No. 5945, retrieved from the internet on Oct. 28, 2011.
ATCC Accession No. 5985, retrieved from the Internet on Oct. 28, 2011.
Bixby, D.L. et al., "CD80 Expression in an HLA-A2-Positive Human Non-Small Cell Lung Cancer Cell Line Enhance Tumor-Specific Cytotoxicity of HLA-A2-Positive T Cells Derived from a Normal Donor and a Patient with Non-Small-Cell Lung Cancer." *Int. J. Cancer*, (1998), 78(6): pp. 685-694.
Boon et al. "Tumor Antigens Recognized by T Lymphocytes." *Annu. Rev. Immunol.* 12(1994): pp. 337-365.
Dohadwala et al. "Non-Small Cell Lung Cancer Cyclooxygenase-2-Dependent Invasion is Mediated by CD44." *J. Biol. Chem.* 276.24(2001): pp. 20809-20812.
European Application No. EP04784998.9, Examination Report dated Jul. 24, 2009, 3 pages.
European Application No. EP04784998.9, Examination Report dated Sep. 25, 2007, 4 pages.
Fong et al. "Dendritic Cells in Cancer Immunotherapy." *Annu. Rev. Immunol.* 18(2000): pp. 245-273.
Fossella et al. "Randomized Phase III Trial of Docetaxel Versus Vinorelbine or Ifosfamide in Patients with Advanced Non-Small-Cell Lung Cancer Previously Treated with Platinam-Containing Chemotherapy Regimens." *J. Clin. Oncol.* 18.12(2000): pp. 2354-2362.
GenBank Accession No. AB030573.
GenBank Accession No. AB030574.
GenBank Accession No. AB030575.
GenBank Accession No. AB032594.
GenBank Accession No. AB032597.
GenBank Accession No. AB048347.
GenBank Accession No. AF221124.
GenBank Accession No. AF221125.
GenBank Accession No. AF389378.
GenBank Accession No. AH000042.
GenBank Accession No. AH003070.
GenBank Accession No. AH003586.
GenBank Accession No. AH006660.
GenBank Accession No. AH006661.
GenBank Accession No. AH006709.
GenBank Accession No. AH007560.
GenBank Accession No. AH009136.
GenBank Accession No. AH013634.
GenBank Accession No. AJ293263.
GenBank Accession No. AJ293264.
GenBank Accession No. BC042665.
GenBank Accession No. K02883.
GenBank Accession No. L15370.
GenBank Accession No. L17005.
GenBank Accession No. L33922.
GenBank Accession No. L34701.
GenBank Accession No. L34703.
GenBank Accession No. L34721.
GenBank Accession No. L34723.
GenBank Accession No. L34724.
GenBank Accession No. L34734.
GenBank Accession No. L34737.
GenBank Accession No. L36318.
GenBank Accession No. L36591.
GenBank Accession No. L38504.
GenBank Accession No. M15497.
GenBank Accession No. M16272.
GenBank Accession No. M16273.
GenBank Accession No. M19756.
GenBank Accession No. M19757.
GenBank Accession No. M20139.
GenBank Accession No. M20179.
GenBank Accession No. M24042.
GenBank Accession No. M24043.
GenBank Accession No. M27537.
GenBank Accession No. M31944.
GenBank Accession No. NM_002116.
GenBank Accession No. NM_002117.

(56) References Cited

OTHER PUBLICATIONS

GenBank Accession No. NM_002127.
GenBank Accession No. NM_005191.
GenBank Accession No. NM_005214.
GenBank Accession No. NM_005514.
GenBank Accession No. NM_006889.
GenBank Accession No. NM_012092.
GenBank Accession No. NM_012292.
GenBank Accession No. NM_152854.
GenBank Accession No. NM_175862.
GenBank Accession No. NT_005612.
GenBank Accession No. NT_008413.
GenBank Accession No. U01848.
GenBank Accession No. U03859.
GenBank Accession No. U03861.
GenBank Accession No. U03862.
GenBank Accession No. U03863.
GenBank Accession No. U03907.
GenBank Accession No. U04243.
GenBank Accession No. U04244.
GenBank Accession No. U04787.
GenBank Accession No. U11267.
GenBank Accession No. U18930.
GenBank Accession No. U21053.
GenBank Accession No. U30904.
GenBank Accession No. U35431.
GenBank Accession No. X02457.
GenBank Accession No. X55710.
GenBank Accession No. X57954.
GenBank Accession No. X60764.
GenBank Accession No. Y13267.
GenBank Accession No. Z23071.
GenBank Accession No. Z27120.
GenBank Accession No. Z30341.
GenBank Accession No. Z33453.
GenBank Accession No. Z46633.
GenBank Accession No. Z70315.
GenBank Accession No. Z97370.
Hoover et al. "Adjuvant Active Specific Immunotherapy for Human Colorectal Cancer: 6.5-year Median Follow-Up of a Phase III Prospectively Randomized Trial." *J. Clin. Oncol.* 11.3(1993): pp. 390-399.
Horig et al. "Phase I Clinical Trial of a Recombinant Canarypoxvirus (ALVAC) Vaccine Expressing Human Carcinoembryonic Antigen and the B7.1 Co-Stimulatory Molecule." *Cancer Immunol. Immunother.* 49.9(2000): pp. 504-514.
Hull et al. "Prostate Cancer Gene Therapy: Comparison of Adenovirus-Mediated Expression of Interleukin 12 with Interleukin 12 plus B7-1 for in Situ Gene Therapy and Gene-Modified, Cell-Based Vaccines." *Clin. Cancer Res.* 6.10(2000): pp. 4101-4109.
International Preliminary Report, Application No. PCT/US2004/031411, dated Mar. 27, 2006.
International Search Report, Application No. PCT/US2009/061035, dated May 1, 2010.
Iwakami et al. "Replication-Deficient Adenovirus-Mediated Transfer of B7-1 (CD80) cDNA Induces Anti-Tumour Immunity in Isolated Human Lung Cancer." *Respirol.* 6.2(2001): pp. 135-144.
Jemal et al. "Cancer Statistics, 2003." *CA Cancer J. Clin.* 53.1(2003): pp. 5-26.
Lee et al. "Increased Immunogenicity of Tumors Bearing Mutant p53 and P1A Epitopes After Transduction of B7-1 via Recombinant Adenovirus". *Cancer Gene Ther.* 3.4(1996): pp. 238-244.
Lissoni et al. "A Randomized Study of Immunotherapy with Low-Dose Subcutaneous Interleukin-2 Plus Melatonin vs Chemotherapy with Cisplatin and Etoposide as First-Line Therapy for Advanced Non-Small Cell Lung Cancer." *Tumori.* 80(1994): pp. 464-467.
Lombardi et al. "Anergic T Cells as Suppressor Cells in Vitro." *Science.* 264(1994): pp. 1587-1589.
Matthias et al. "A Bovine Papilloma Virus Vector with a Dominant Resistance Marker Replicates Extrachromosomally in Mouse and *E. coli* Cells." *EMBO J.* 2.9(1983): pp. 1487-1492.
Morton et al. "Prolonged Survival of Patients Receiving Active Immunotherapy with Canvaxin Therapeutic Polyvalent Vaccine After, Complete Resection of Melanoma Metastatic to Regional Lymph Nodes." *Ann. Surg.* 236.4(2002): pp. 438-449.
Nawrocki et al. "Genetically Modified Tumor Vaccines—Where we are Today." *Cancer Treat. Res.* 25.1(1999): pp. 29-46.
Neuner et al. "Cytokine Secretion: Clinical Relevance of Immunosuppression in Non-Small Cell Lung Cancer." *Lung Cancer.* 34(2001):S79-S82.
Neuner et al. "Prognostic Significance of Cyotkine Modulation in Non-Small Cell Lung Cancer." *Int. J. Cancer.* 101(2002): pp. 287-292.
Ohe et al. "Construction of a Novel Bovine Papillomavirus Vector without Detectable Transforming Activity Suitable for Gene Transfer." *Hum. Gene Ther.* 6(1995): pp. 325-333.
Padmanabhan et al. "Immunotherapy of Non-Immunogenic Tumors: Phase I Clinical Trial of HLA-A,B7.1 Transfected Adenocarcinoma Vaccine Causing Direct Priming of CTLs in Lung Cancer." *Proc. Am. Assc. Cancer Res.* (2002) 43: pp. 557.
Pavlakis et al. "Regulation of a Metallothionein-Growth Hormone Hybrid Gene in Bovine Papilloma Virus." *PNAS.* 80(1983): pp. 397-401.
Podack et al. "Functional Significance of Two Cytolytic Pathways of Cytotoxic T Lymphocytes." *J. Leuk. Biol.* 57(1995): pp. 548-552.
Raez et al. "Allogeneic Vaccination with a B7.1 HLA-A Gene-Modified Adenocarcinoma Cell Line in Patients with Advanced Non-Small-Cell Lung Cancer." *J. Clin. Oncol.* (2004) 22(14): pp. 2800-2807.
Ratto et al. "A Randomized Trial of Adoptive Immunotherapy with Tumor-Infiltrating Lymphocytes and Interleukin-2 Versus Standard Therapy in the Postoperative Treatment of Resected Nonsmall Cell Lung Carcinoma." *Cancer.* 78.2(1996): pp. 244-251.
Ratto et al. "Phase II Study of Combined Immunotherapy, Chemotherapy, and Radiotherapy in the Postoperative Treatment of Advanced Non-Small-Cell Lung Cancer." *J. Immunother.* 23.1(2000): pp. 161-167.
Rokkones et al. "Expression of Human Parathyroid Hormone in Mammalian Cells, *Escherichia coli* and *Saccharomyces cerevisiae.*" *J. Biotechnol.* 33(1994): pp. 293-306.
Sarver et al. "Bovine Papilloma Virus Deoxyribonucleic Acid: A Novel Eucaryotic Cloning Vector." *Mol. Cell. Biol.* 1.6(1981): pp. 486-496.
Schiller et al. "Comparison of Four Chemotherapy Regimens for Advanced Non-Small-Cell Lung Cancer." *N. Eng. J. Med.* 349.2(2002): pp. 92-98.
Schwartz. "Models of T Cell Anergy: Is There a Common Molecular Mechanism?" *J. Exp. Med.* 184(1996): pp. 1-8.
Shepherd et al. "Prospective Randomized Trial of Docetaxel Versus Best Supportive Care in Patients with Non-Small-Cell Lung Cancer Previously Treated with Platinum-Based Chemotherapy." *J. Clin. Oncol.* 18.10(2000): pp. 2095-2103.
So et al. "Generation of Autologous Tumor-Specific T Cell Clones From a Patient with Adenosquamous Carcinoma of the Lung." *Jpn. J. Clin. Oncol.* 31(7): pp. 311-317.
Stephens et al. "The Big Lung Trial (BLT): Determining the Value of Cisplatin-Based Chemotherapy for All Patient with Non-Small Cell Lung Cancer (NSCLC)." *Proc. Am. Soc. Clin. Oncol.* 21(2002): pp. 291a.
Takahashi et al. "Induction of CD8+ Cytotoxic T Cells by Immunization with Purified HIV-1 Envelope Proteins in ISCOMs." *Nature.* 344(1990): pp. 873-875.
Takendyama et al. "Successful Induction of Tumor-Specific Cytotoxic T Lymphocytes from Patients with Non-Small Cell Lung Cancer." *Jpn. J. Cancer Res.* 2001 (92): pp. 309-315.
Velders et al. "Active Immunization Against Cancer Cells: Impediments and Advances." *Sem. Oncol.* 25.6(1998): pp. 697-706.
von Mehren et al. "Pilot Study of a Dual Gene Recombinant Avipox Vaccine Containing Both Carcinoembryonic Antigen (CEA) and B7.1 Transgenes in Patients with Recurrent CEAExpressing Adenocarcinomas." *Clin. Cancer Res.* 6(2000): pp. 2219-2228.

(56) References Cited

OTHER PUBLICATIONS

Warren et al. "Future Prospects for Vaccine Adjuvants." *CRC Crit. Rev. Immunol.* 8.2(1988): pp. 83-101.
Weynants et al. "Derivation of Tumor-Specific Cytolytic T-Cell Clones from Two Lung Cancer Patients with Long Survival." *Am. J. Respir. Crit. Care Med.* 159(1999): pp. 55-62.
Woo et al. "Cutting Edge: Regulatory T Cells from Lung Cancer Patients Directly Inhibit Autologous T Cell Proliferation." *J. Immunol.* 2002 (168): pp. 4272-4276.
Woo et al. "Regulatory CD4+CD25+ T Cells in Tumors from Patients with Early-Stage Non-Small Cell Lung Cancer and Late-Stage Ovarian Cancer." *Cancer Res.* 61.12(2001): pp. 4766-4772.
Woodlock et al. "Active Specific immunotherapy for Metastatic Colorectal Carcinoma: Phase I Study of an Allogeneic Cell Vaccine Plus Low-Dose Interleukin-1_." *J. Immunother.* 22.3(1999): pp. 251-259.
Yamada et al. "Gene and Peptide Analyses of Newly Defined Lung Cancer Antigens Recognized by HLA-A2402-Restricted Tumor-Specific Cytotoxic T Lymphocytes." *Cancer Res.* 63(2003): pp. 2829-2835.
Yamazaki et al. "Small Cell Lung Carcinomas Express Shared and Private Tumor Antigens Presented by HLA-A1 or HLA-A2." *Cancer Res.* 59(1999): pp. 4642-4650.
American Cancer Society 2016 publication. entitled "What is Small Cell Lung Cancer", 4 pages.
Final Office Action corresponding to U.S. Appl. No. 10/950,157, dated Jun. 9, 2016, 13 pages.
Final Office Action corresponding to U.S. Appl. No. 10/950,157, dated May 27, 2011, 9 pages.
Final Office Action corresponding to U.S. Appl. No. 10/950,157, dated May 14, 2016, 19 pages.
Nakanshi et al. "Treatment of lung cancer—state of the art in 2000", *Gan to Kagaku Ryoho*, 27(8):1247-52 (2000) (abstract only).
Non-Final Office Action corresponding to U.S. Appl. No. 10/950,157, dated Nov. 9, 2010, 10 pages.
Non-Final Office Action corresponding to U.S. Appl. No. 10/950,157, dated Aug. 18, 2014, 15 pages.
Non-Final Office Action corresponding to U.S. Appl. No. 10/950,157, dated Jan. 13, 2016, 11 pages.
Non-Final Office Action corresponding to U.S. Appl. No. 10/950,157, dated Sep. 6, 2017, 13 pages.
Sheski et al. "Endoscopic Treatment of Early-Stage Lung Cancer", *Cancer Control*, 7(1):35-44 (2000).
Toh et al. "Differences between small-cell lung cancer and non-small-cell ung cancer among tobacco smokers", *Lung Cancer*, 56(2):161-166 (2007) (abstract only).
Borghael et al. "Nivolumab versus Docetaxel in Advanced Nonsquamous Non—Small-Cell Lung Cancer", *N Engl. J. Med.* 373(17):1527-1639 (2015).
Ciuleanu et al. "Maintenance pemetrexed plus best supportive care versus placebo plus best supportive care for non-small-cell lung cancer: a randomised, double-blind, phase 3 study", *The Lancet* 374:1432-1440 (2009).
Das and Wakelee "Angiogenesis and lung cancer; ramucirumab prolongs survival in 2nd-line metastatic NSCLC", *Transl. Lung Cancer Res.* 3 (6):397-399 (2014).
FDA approved drug notification of Mar. 4, 2015 for nivoiumab.
FDA News Release of Oct. 9, 2015, entitled *FDA expands approved use of Opdivo in advanced lung cancer*.
Final Office Action corresponding to U.S. Appl. No. 10/950,157, dated Mar. 21. 2018, 16 pages.
Gazdar, Adi and Oie, Herbert "Cell Culture Methods for Human Lung Cancer" Cancer Genet. Cytogenet. 19:5-10 (1986).
Haringhuizen et al. "Gefitinib as a last treatment option for non-small-cell lung cancer: durable disease control in a subset of patients" (*Annals Oncol*. 15: 786-792 (2004)).
Hirsch et al. "The Prognostic and Predictive Role of Histology in Advanced Non-small Cell Lung Cancer", *J. Thoracic Oncol.* 3(12)1468-1481 (2008)).
Liu-Jarin et al. Histologic Assessment of Non—-Small Cell Lung Carcinoma after Neoadjuvant Therapy, (*Mod. Pathol* 16 (11): 1102-1108 (2003).
M. Wortman "Targeting Cancer by Subtype", *Yale Medicine* Winter 2002, p. 28-32.
Masters et al. "Systemic Therapy for Stage IV Non—Small-Cell Lung Cancer: American Society of Ciinical Oncology Clinical Practice Guideline Update", *J. Clin Oncol*. 33(3):3488-3515 (2015).
Scagliotti et al. "Phase III Study Comparing Cispiatin Plus Gemcitabine with Cisplatin Plus Pemetrexed in Chemotherapy-Naïve Patients with Advanced-Stage Non—Small-Cell Lung Cancer", *J. Clin. Oncol*26(21):3543-3551, 3549 (2008).
Syrigos et al. "Prognostic and predictive factors in a randomized phase III trial comparing cisplatin-pemetrexed versus cisplatin-gemcitabine in advanced non-small-cell lung cancer" *Ann. Oncol*. 21:556-561 (2009.
Wientraub, A. Cure Today, *Hitting a target in advanced non-small cell lung cancer*; http://www.curetoday.com/publications/cure/2015/lung-2015/hitting-a-target-in-advanced-non-small-ceil-lung-cancer?p=2#sthash.1Oa.ZRT4A.dpuf).
Yeoh et al. "Classification, subtype discovery, and prediction of outcome in pediatric acute lymphoblastic leukemia by gene expression profiling", *Cancer Cell* 1:133-143 (Mar. 2002).
Zhou F. and C. Zhou. "Necitumumab for patients with non-squamous NSCLC: uninspiring results", *The Lancet* 16:246-247 (2015).

\* cited by examiner

* BECAUSE ONE OR MORE PATIENTS ARE STILL ALIVE IN THESE GROUPS, MEAN SURVIVAL IS CONTINUALLY INCREASING, BUT IS AT LEAST AS GREAT AS THE LEVEL SHOWN.

SEQUENCE LISTING

<160> NUMBER OF SEQ ID NOS: 7

<210> SEQ ID NO 1

<211> LENGTH: 30924
<212> TYPE: DNA
<213> ORGANISM: Artificial Sequence
<220> FEATURE:
<223> OTHER INFORMATION: Chemically synthesized Plasmid DNA

<400> SEQUENCE: 1

| | |
|---|---|
| tctagagagc ttggcccatt gcatacgttg tatccatatc ataatatgta agatctctcg | 60 |
| aaccgggtaa cgtatgcaac ataggtatag tattatacat catttatatt ggctcatgtc | 120 |
| caacattacc gccatgttga cattgattat gtaaatataa ccgagtacag gttgtaatgg | 180 |
| cggtacaact gtaactaata tgactagtta ttaatagtaa tcaattacgg ggtcattagt | 240 |
| tcatagccca actgatcaat aattatcatt agttaatgcc ccagtaatca agtatcgggt | 300 |
| tatatggagt tccgcgttac ataacttacg gtaaatggcc cgcctggctg atatacctca | 360 |
| aggcgcaatg tattgaatgc catttaccgg gcggaccgac accgcccaac gacccccgcc | 420 |
| cattgacgtc aataatgacg tatgttccca tggcgggttg ctggggggcgg gtaactgcag | 480 |
| ttattactgc atacaagggt tagtaacgcc aatagggact ttccattgac gtcaatgggt | 540 |
| ggagtattta atcattgcgg ttatccctga aggtaactg cagttaccca cctcataaat | 600 |
| cggtaaactg cccacttggc agtacatcaa gtgtatcata tgccaagtac gccatttgac | 660 |
| gggtgaaccg tcatgtagtt cacatagtat acggttcatg gcccctatt gacgtcaatg | 720 |
| acggtaaatg gcccgcctgg cattatgccc cgggggataa ctgcagttac tgccatttac | 780 |
| cgggcggacc gtaatacggg agtacatgac cttatgggac tttcctactt ggcagtacat | 840 |
| ctacgtatta tcatgtactg gaataccctg aaaggatgaa ccgtcatgta gatgcataat | 900 |
| gtcatcgcta ttaccatggt gatgcggttt tggcagtaca tcaatgggcg cagtagcgat | 960 |
| aatggtacca ctacgccaaa accgtcatgt agttacccgc tggatagcgg tttgactcac | 1020 |
| ggggatttcc aagtctccac cccattgacg acctatcgcc aaactgagtg cccctaaagg | 1080 |
| ttcagaggtg gggtaactgc tcaatgggag ttttgttttgg caccaaaatc aacgggactt | 1140 |
| tccaaaatgt agttaccctc aaacaaaacc gtggttttag ttgccctgaa aggttttaca | 1200 |
| cgtaacaact ccgccccatt gacgcaaatg ggcggtaggc gtgtacggtg gcattgttga | 1260 |
| ggcggggtaa ctgcgtttac ccgccatccg cacatgccac ggaggtctat ataagcagag | 1320 |
| ctcgtttagt gaaccgtcag atcgcctgga cctccagata tattcgtctc gagcaaatca | 1380 |
| cttggcagtc tagcggacct gacgccatcc acgctgtttt gacctccata gaagacaccg | 1440 |
| ggaccgatcc ctgcggtagg tgcgacaaaa ctggaggtat cttctgtggc cctggctagg | 1500 |
| agcctccggt cgatcgaccg atcctgagaa cttcagggtg agtttgggga tcggaggcca | 1560 |
| gctagctggc taggactctt gaagtcccac tcaaaccct ccttgattg ttctttcttt | 1620 |
| ttcgctattg taaaattcat gttatatgga gggaactaac aagaaagaaa aagcgataac | 1680 |
| attttaagta caatatacct gggggcaaag ttttcagggt gttgtttaga atgggaagat | 1740 |
| gtcccttgta cccccgtttc aaaagtccca caacaaatct tacccttcta cagggaacat | 1800 |
| tcaccatgga ccctcatgat aattttgttt ctttcacttt ctactctgtt agtggtacct | 1860 |
| gggagtacta ttaaaacaaa gaaagtgaaa gatgagacaa gacaaccatt gtctcctctt | 1920 |
| attttctttt catttctgt aacttttttcg ctgttggtaa cagaggagaa taaaagaaaa | 1980 |
| gtaaaagaca ttgaaaaagc ttaaacttta gcttgcattt gtaacgaatt tttaaattca | 2040 |
| cttttgttta aatttgaaat cgaacgtaaa cattgcttaa aaatttaagt gaaacaaat | 2100 |
| tttgtcagat tgtaagtact ttctctaatc acttttttt caaggcaatc aaacagtcta | 2160 |

```
acattcatga aagagattag tgaaaaaaaa gttccgttag agggtatatt atattgtact    2220
tcagcacagt tttagagaac aattgttata tcccatataa tataacatga agtcgtgtca    2280
aaatctcttg ttaacaatat attaaatgat aaggtagaat atttctgcat ataaattctg    2340
gctggcgtgg taatttacta ttccatctta taaagacgta tatttaagac cgaccgcacc    2400
aaatattctt attggtagaa acaactacac cctggtcatc atcctgcctt tttataagaa    2460
taaccatctt tgttgatgtg ggaccagtag taggacggaa tctctttatg gttacaatga    2520
tatacactgt ttgagatgag gataaaatac agagaaatac caatgttact atatgtgaca    2580
aactctactc ctattttatg tctgagtcca aaccgggccc ctctgctaac catgttcatg    2640
ccttcttctc agactcaggt ttggcccggg gagacgattg gtacaagtac ggaagaagag    2700
tttcctacag ctcctgggca acgtgctggt tgttgtgctg tctcatcatt aaaggatgtc    2760
gaggacccgt tgcacgacca acaacacgac agagtagtaa ttggcaaaga attcctcgag    2820
gaagccatgg gccacacacg gaggcaggga accgtttct taaggagctc cttcggtacc     2880
cggtgtgtgc ctccgtccct acatcaccat ccaagtgtcc atacctcaat ttctttcagc    2940
tcttggtgct tgtagtggta ggttcacagg tatggagtta agaaagtcg agaaccacga     3000 ggctggtctt tctcacttct gttcaggtgt tatccacgtg accaaggaag ccgaccagaa    3060
agagtgaaga caagtccaca ataggtgcac tggttccttc tgaaagaagt ggcaacgctg    3120
tcctgtggtc acaatgtttc tgttgaagag actttcttca ccgttgcgac aggacaccag    3180
tgttacaaag acaacttctc ctggcacaaa ctcgcatcta ctggcaaaag gagaagaaaa    3240
tggtgctgac gaccgtgttt gagcgtagat gaccgttttc ctcttctttt accacgactg    3300
tatgatgtct ggggacatga atatatggcc cgagtacaag aaccggacca atactacaga    3360
cccctgtact tatataccgg gctcatgttc ttggcctggt tctttgatat cactaataac    3420
ctctccattg tgatcctggc tctgcgccca agaaactata gtgattattg gagaggtaac    3480
actaggaccg agacgcgggt tctgacgagg gcacatacga gtgtgttgtt ctgaagtatg    3540
aaaaagacgc agactgctcc cgtgtatgct cacacaacaa gacttcatac ttttctgcg     3600 tttcaagcgg gaacacctgg ctgaagtgac gttatcagtc aaagctgact aaagttcgcc    3660
cttgtggacc gacttcactg caatagtcag tttcgactga tccctacacc tagtatatct    3720
gactttgaaa ttccaacttc taatattaga agggatgtgg atcatataga ctgaaacttt    3780
aaggttgaag attataatct aggataattt gctcaacctc tggaggtttt ccagagcctc    3840
acctctcctg tcctattaaa cgagttggag acctccaaaa ggtctcggag tggagaggac    3900
gttggaaaat ggagaagaat taaatgccat caacacaaca gtttcccaag caaccttta     3960 cctcttctta atttacggta gttgtgttgt caaagggttc atcctgaaac tgagctctat    4020
gctgttagca gcaaactgga cttcaatatg taggactttg actcgagata cgacaatcgt    4080
cgtttgacct gaagttatac acaaccaacc acagcttcat gtgtctcatc aagtatggac    4140
atttaagagt tgttggttgg tgtcgaagta cacagagtag ttcatacctg taaattctca    4200
gaatcagacc ttcaactgga atacaaccaa gcaagagcat tttcctgata cttagtctgg    4260
aagttgacct tatgttggtt cgttctcgta aaaggactat acctgctccc atcctgggcc    4320
attaccttaa tctcagtaaa tggaattttt tggacgaggg taggacccgg taatggaatt    4380
agagtcattt acctttaaaaa gtgatatgct gcctgaccta ctgctttgcc ccaagatgca    4440
gagagagaag cactatacga cggactggat gacgaaacgg ggttctacgt ctctctcttc    4500
```

```
gaggaatgag agattgagaa gggaaagtgt acgccctgta taacagacta ctccttactc    4560
tctaactctt cccttttcaca tgcgggacat attgtctgat gtcaaattaa gccgaattct    4620
gcagatatcc atcacactgg cggccgctcg cagtttaatt cggcttaaga cgtctatagg    4680
tagtgtgacc gccggcgagc aggaattcac tcctcaggtg caggctgcct atcagaaggt    4740
ggtggctggt tccttaagtg aggagtccac gtccgacgga tagtcttcca ccaccgacca    4800
gtggccaatg ccctggctca caaataccac tgagatcttt ttccctctgc caccggttac    4860
gggaccgagt gtttatggtg actctagaaa aagggagacg caaaaattat ggggacatca    4920
tgaagcccct tgagcatctg acttctggct gttttttaata cccctgtagt acttcgggga    4980
actcgtagac tgaagaccga aataaaggaa atttattttc attgcaatag tgtgttggaa    5040 tttttttgtgt ttatttcctt taaataaaag taacgttatc acacaacctt aaaaaacaca    5100
ctctcactcg gaaggacata tgggagggca aatcatttaa aacatcagaa gagagtgagc    5160
cttcctgtat accctcccgt ttagtaaatt ttgtagtctt tgagtatttg gtttagagtt    5220
tggcaacata tgcccatatg ctggctgcca actcataaac caaatctcaa accgttgtat    5280
acgggtatac gaccgacggt tgaacaaagg ttggctataa agaggtcatc agtatatgaa    5340 acagcccct acttgtttcc aaccgatatt tctccagtag tcatatactt tgtcggggga    5400
gctgtccatt ccttattcca tagaaaagcc ttgacttgag gttagatttt cgacaggtaa    5460
ggaataaggt atcttttcgg aactgaactc caatctaaaa ttttatattt tgttttgtgt    5520 tattttttc tttaacatcc ctaaaatttt aaaatataaa acaaaacaca ataaaaaaag    5580
aaattgtagg gattttaaaa ccttacatgt tttactagcc agattttttcc tcctctcctg    5640 actactccca ggaatgtaca aaatgatcgg tctaaaaagg aggagaggac tgatgagggt    5700
gtcatagctg tccctcttct cttatggaga tccctcgacg gatccctaga cagtatcgac    5760
agggagaaga gaatacctct agggagctgc ctagggatct gtcgaggcga tgcggcgcag    5820
caccatggcc tgaaataacc tctgaaagag cagctccgct acgccgcgtc gtggtaccgg    5880
actttattgg agactttctc gaacttggtt aggtaccttg gttttttaaaa ccagcctgga    5940 gtagagcaga cttgaaccaa tccatggaac caaaaatttt ggtcggacct catctcgtct    6000
tgggttaagg tgagtgaccc ctcagccctg gacattctta tgatgagcccc acccaattcc    6060 actcactggg gagtcgggac ctgtaagaat ctactcgggg ctcaggagta gagaataatg    6120
ttgagatgag ttctgttggc taaaataatc gagtcctcat ctcttattac aactctactc    6180
aagacaaccg attttattag aaggctagtc tttataaaac tgtctcctct tctcctagct    6240
tcgatccaga ttccgatcag aaatattttg acagaggaga agaggatcga agctaggtct    6300
gagagacctg ggcggagctg gtcgctgctc aggaactcca ggaaaggaga ctctctggac    6360
ccgcctcgac cagcgacgag tccttgaggt cctttcctct agctgaggtt accacgctgc    6420
gaatgggttt acgagatag ctggctttcc tcgactccaa tggtgcgacg cttacccaaa    6480
tgcctctatc gaccgaaagg ggggtgagtt ctcgtaaact ccagagcagc gataggccgt    6540
aatatcgggg ccccactcaa gagcatttga ggtctcgtcg ctatccggca ttatagcccc    6600
aaagcactat agggacatga tgttccacac gtcacatggg tcgtcctatc tttcgtgata    6660
tccctgtact acaaggtgtg cagtgtaccc agcaggatag cgagccagtc gtgccaaagg    6720
ggcggtcccg ctgtgcacac tggcgctcca gctcggtcag cacggtttcc ccgccagggc    6780
gacacgtgtg accgcgaggt gggagctctg cactccgccc gaaaagtgcg ctcggctctg    6840
ccaggacgcg ccctcgagac gtgaggcggg cttttcacgc gagccgagac ggtcctgcgc    6900
```

```
gggcgcgtga ctatgcgtgg gctggagcaa ccgcctgctg ggtgcaaacc cccgcgcact   6960
gatacgcacc cgacctcgtt ggcggacgac ccacgtttgg ctttgcgccc ggactcgtcc   7020
aacgactata agagggcag gctgtcctct gaaacgcggg cctgagcagg ttgctgatat    7080
ttctcccgtc cgacaggaga aagcgtcacc acgacttcaa cgtcctgagt accttctcct   7140
cacttactcc ttcgcagtgg tgctgaagtt gcaggactca tggaagagga gtgaatgagg   7200
gtagctccag cttcaccacc aagctcctcg acgtcgaccc cagacgccga catcgaggtc   7260
gaagtggtgg ttcgaggagc tgcagctggg gtctgcggct ggatggccgt catggcgccc   7320
cgaaccctcc tcctgctact ctcggggggcc cctaccggca gtaccgcggg gcttgggagg  7380
aggacgatga gagccccggg ctggccctga cccagacctg ggcgggctcc cactccatga   7440
ggtatttctt gaccgggact gggtctggac ccgcccgagg gtgaggtact ccataaagaa   7500
cacatccgtg tcccggcccg ccgcggggga gccccgcttc atcgccgtgg gtgtaggcac   7560
agggccgggc cggcgcccct cggggcgaag tagcggcacc gctacgtgga cgacacgcag   7620
ttcgtgcggt tcgacagcga cgccgcgagc cgatgcacct gctgtgcgtc aagcacgcca   7680
agctgtcgct gcggcgctcg cagaagatgg agccgcgggc gccgtggata gagcaggagg   7740
ggccggagta gtcttctacc tcggcgcccg cggcacctat ctcgtcctcc ccggcctcat   7800
ttgggaccag gagacacgga atatgaaggc ccactcacag actgaccgag aaccctggtc   7860
ctctgtgcct tatacttccg ggtgagtgtc tgactggctc cgaacctggg gaccctgcgc   7920
ggctactaca accagagcga ggacggttct gcttggaccc ctgggacgcg ccgatgatgt   7980
tggtctcgct cctgccaaga cacaccatcc agataatgta tggctgcgac gtggggccgg   8040
acgggcgctt gtgtggtagg tctattacat accgacgctg caccccggcc tgcccgcgaa   8100
cctccgcggg taccggcagg acgcctacga cggcaaggat tacatcgccc ggaggcgccc   8160
atggccgtcc tgcggatgct gccgttccta atgtagcggg tgaacgagga cctgcgctct   8220
tggaccgcgg cggacatggc ggctcagatc acttgctcct ggacgcgaga acctggcgcc   8280
gcctgtaccg ccgagtctag accaagcgca agtgggaggc ggcccatgcg gcggagcagc   8340
ggagagtcta tggttcgcgt tcaccctccg ccgggtacgc cgcctcgtcg cctctcagat   8400
cctggatggc cggtgcgtgg acgggctccg cagatacctg gagaacggga ggacctaccg   8460
gccacgcacc tgcccgaggc gtctatggac ctcttgccct aggagacgct gcagcgcacg   8520
gaccccccca agacacatat gacccaccac tcctctgcga cgtcgcgtgc ctgggggggt   8580
tctgtgtata ctgggtggtg cccatctctg accatgaggc caccctgagg tgctgggccc   8640
tgggcttcta gggtagagac tggtactccg gtgggactcc acgacccggg acccgaagat   8700
ccctgcggag atcacactga cctggcagcg ggatggggag gaccagaccc gggacgcctc   8760
tagtgtgact ggaccgtcgc cctacccctc ctggtctggg aggacacgga gctcgtggag   8820
accaggcctg caggggatgg aaccttccag tcctgtgcct cgagcacctc tggtccggac   8880
gtcccctacc ttggaaggtc aagtgggcgg ctgtggtggt gccttctgga gaggagcaga   8940
gatacacctg ttcacccgcc gacaccacca cggaagacct ctcctcgtct ctatgtggac   9000
ccatgtgcag catgagggtc tgcccaagcc cctcaccctg agatgggagc ggtacacgtc   9060
gtactcccag acgggttcgg ggagtgggac tctaccctcg tgtcttccca gcccaccatc   9120
cccatcgtgg gcatcattgc tggcctggtt acagaagggt cgggtggtag gggtagcacc   9180
cgtagtaacg accggaccaa ctccttggag ctgtgatcac tggagctgtg gtcgctgccg   9240
```

```
tgatgtggag gaggaacctc gacactagtg acctcgacac cagcgacggc actacacctc    9300
gaggaagagc tcagatagaa aaggagggag ttacactcag gctgcaagca ctccttctcg    9360
agtctatctt ttcctccctc aatgtgagtc cgacgttcgt gtgacagtgc ccagggctct    9420
gatgtgtccc tcacagcttg taaagtgtga cactgtcacg ggtcccgaga ctacacaggg    9480
agtgtcgaac atttcacact gacagctgcc ttgtgtggga ctgagaggca agagttgttc    9540
ctgcccttcc ctgtcgacgg aacacaccct gactctccgt tctcaacaag gacgggaagg    9600
ctttgtgact tgaagaaccc tgactttgtt tctgcaaagg cacctgcatg gaaacactga    9660
acttcttggg actgaaacaa agacgtttcc gtggacgtac tgtctgtgtt cgtgtaggca    9720
taatgtgagg aggtggggag agcaccccac acagacacaa gcacatccgt attacactcc    9780 tccaccccctc tcgtggggtg ccctgtcca ccatgaccct cttcccacgc tgacctgtgc    9840
tccctcccca ggggacaggt ggtactggga aagggtgcg actggacacg agggaggggt    9900
aaagcttgat atccaattcc tgcagcccgg gggatccact ttttctaggt tttcgaacta    9960
taggttaagg acgtcgggcc ccctaggtga aaaagatcca cgaccgatcc tgagaacttc   10020
agggtgagtt tggggaccct tgattgttct gctggctagg actcttgaag tcccactcaa   10080 accccctggga actaacaaga ttcttttttcg ctattgtaaa attcatgtta tatggagggg   10140
gcaaagtttt aagaaaaagc gataacattt taagtacaat ataccctcccc cgtttcaaaa   10200 cagggtgttg tttagaatgg gaagatgtcc cttgtatcac catggaccct gtcccacaac   10260
aaatcttacc cttctacagg gaacatagtg gtacctggga catgataatt ttgtttctttt   10320 cactttctac tctgttgaca accattgtct gtactattaa aacaaagaaa gtgaaagatg   10380
agacaactgt tggtaacaga cctcttatttt tctttttcatt ttctgtaact ttttcgttaa   10440
actttagctt ggagaataaa agaaaagtaa aagacattga aaaagcaatt tgaaatcgaa   10500
gcatttgtaa cgaattttta aattcacttt tgtttatttg tcagattgta cgtaaacatt   10560
gcttaaaaat ttaagtgaaa acaaataaac agtctaacat agtactttct ctaatcactt   10620 tttttttcaag gcaatcaggg tatattatat tcatgaaaga gattagtgaa aaaaaagttc   10680
cgttagtccc atataatata tgtacttcag cacagttta gagaacaatt gttataatta   10740
aatgataagg acatgaagtc gtgtcaaaat ctcttgttaa caatattaat ttactattcc   10800
tagaatattt ctgcatataa attctggctg gcgtggaaat attcttattg atcttataaa   10860
gacgtatatt taagaccgac cgcacccttta taagaataac gtagaaacaa ctacaccctg   10920
gtcatcatcc tgccttttctc tttatggtta catctttgtt gatgtgggac cagtagtagg   10980
acggaaagag aaataccaat caatgatata cactgtttga gatgaggata aaatactctg   11040
agtccaaacc gttactatat gtgacaaact ctactcctat tttatgagac tcaggtttgg   11100 gggccccctct gctaaccatg ttcatgcctt cttctctttc ctacagctcc cccggggaga   11160
cgattggtac aagtacggaa gaagagaaag gatgtcgagg tgggcaacgt gctggttgtt   11220
gtgctgtctc atcattttgg caaagaattc acccgttgca cgaccaacaa cacgacagag   11280
tagtaaaacc gtttcttaag ctcgaccagt gcaggctgcc tatcagaaag tggtggctgg   11340
tgtggctaat gagctggtca cgtccgacgg atagtctttc accaccgacc acaccgatta   11400
gccctggccc acaagtatca ctaagctcgc tttcttgctg tccaatttct cgggaccggg   11460
tgttcatagt gattcgagcg aaagaacgac aggttaaaga attaaaggtt cctttgttcc   11520
ctaagtccaa ctactaaact gggggatatt taatttccaa ggaaacaagg gattcaggtt   11580
gatgatttga ccccctataa atgaagggcc ttgagcatct ggattctgcc taataaaaaa   11640
```

```
catttatttt tacttcccgg aactcgtaga cctaagacgg attatttttt gtaaataaaa   11700
cattgcaatg atgtatttaa attatttctg aatattttac taaaaaggga gtaacgttac   11760
tacataaatt taataaagac ttataaaatg attttccct atgtgggagg tcagtgcatt    11820
taaaacataa agaaatgaag agctagttca tacaccctcc agtcacgtaa attttgtatt   11880
tctttacttc tcgatcaagt aaccttggga aaatacacta tatcttaaac tccatgaaag   11940
aaggtgaggc ttggaaccct tttatgtgat atagaatttg aggtactttc ttccactccg   12000
tgcaaacagc taatgcacat tggcaacagc ccctgatgcc tatgccttat acgtttgtcg   12060
attacgtgta accgttgtcg gggactacgg atacggaata tcatccctca gaaaaggatt   12120
caagtagagg cttgatttgg aggttaaagt agtagggagt cttttcctaa gttcatctcc   12180
gaactaaacc tccaatttca tttgctatgc tgtattttac attacttatt gtttagctg    12240 tcctcatgaa aaacgatacg acataaaatg taatgaataa caaaatcgac aggagtactt   12300
tgtcttttca ctaccatttt gcttatcctg catctctcag ccttgactcc acagaaaagt   12360
gatgggtaaa cgaataggac gtagagagtc ggaactgagg actcagttct cttgcttaga   12420
gataccacct ttccctgaa gtgttccttc tgagtcaaga aacgaatct ctatggtgga    12480 aaggggactt cacaaggaag catgtttac ggcgagatgg tttctcctcg cctggccact    12540
cagccttagt gtacaaaatg ccgctctacc aagaggagc ggaccggtga gtcggaatca    12600
tgtctctgtt gtcttataga ggtctacttg aagaaggaaa aacaggggc acagagacaa    12660 cagaatatct ccagatgaac ttcttccttt ttgtcccccg atggtttgac tgtcctgtga   12720 gccctcttc cctgcctccc ccactcacag taccaaactg acaggacact cgggaagaag   12780
ggacggaggg ggtgagtgtc tgacccggaa tctgcagtgc tagtctcccg gaactatcac   12840
tctttcacag actgggcctt agacgtcacg atcagagggc cttgatagtg agaaagtgtc   12900
tctgcttggg aaggactggg cttagtatga aaagttagga ctgagaagaa agacgaaacc   12960
ttcctgaccc gaatcatact tttcaatcct gactcttctt tttgaaaggg ggcttttttgt  13020 agcttgatat tcactactgt cttattaccc aaactttccc ccgaaaaaca tcgaactata   13080
agtgatgaca gaataatggg tatcataggc ccaccccaaa tggaagtccc attcttcctc   13140
aggatgttta atagtatccg ggtggggttt accttcaggg taagaaggag tcctacaaat   13200
agattagcat tcaggaagag atcagaggtc tgctggctcc cttatcatgt tctaatcgta   13260
agtccttctc tagtctccag acgaccgagg gaatagtaca cccttatggt gcttctggct   13320
ctgcagttat tagcatagtg ttaccatcaa gggaatacca cgaagaccga gacgtcaata   13380
atcgtatcac aatggtagtt ccaccttaac ttcattttc ttattcaata cctaggtagg    13440
tagatgctag ggtggaattg aagtaaaaag aataagttat ggatccatcc atctacgatc   13500
attctggaaa taaatatga gtctcaagtg gtccttgtcc tctctcccag taagaccttt     13560
attttatact cagagttcac caggaacagg agagagggtc tcaaattctg aatctagttg   13620
gcaagattct gaaatcaagg catataatca agtttaagac ttagatcaac cgttctaaga   13680
ctttagttcc gtatattagt gtaataagta atgatagaag ggtatataga agaattttat   13740
tatatgagag cattattcac tactatcttc ccatatatct tcttaaaata atatactctc   13800
ggtgaaatcc cagcaatttg ggaggctgag gcaggagaat cgcttgatcc ccactttagg   13860
gtcgttaaac cctccgactc cgtcctctta gcgaactagg tgggaggcag aggttgcagt   13920
gagccaagat tgtgccactg cattccagcc accctccgtc tccaacgtca ctcggttcta   13980
```

```
acacggtgac gtaaggtcgg caggtgacag catgagactc cgtcacaaaa aaaaaagaaa    14040
aaaaaggggg gtccactgtc gtactctgag gcagtgtttt tttttctttt tttttccccc    14100
gggggggcgg tggagccaag atgaccgaat aggaacagct ccagtactat cccccccgcc    14160
acctcggttc tactggctta tccttgtcga ggtcatgata agctcccatc gtgagtgacg    14220
cagaagacgg gtgatttctg catttccaac tcgagggtag cactcactgc gtcttctgcc    14280
cactaaagac gtaaaggttg tgaggtacca ggttcatctc acagggaagt gccaggcagt    14340
gggtgcagga actccatggt ccaagtagag tgtcccttca cggtccgtca cccacgtcct    14400
cagtaggtgc agtgcactgt gcatgagccg aagcagggac gaggcatcac gtcatccacg    14460
tcacgtgaca cgtactcggc ttcgtccctg ctccgtagtg ctcacccggg aagcacaagg    14520
ggtcagggaa ttccctttcc tagtcaaaga gagtgggccc ttcgtgttcc ccagtccctt    14580
aagggaaagg atcagtttct aaagggtgac agatggcacc tggaaaatcg ggtcactccc    14640
gccctaatac tttcccactg tctaccgtgg acctttttagc ccagtgaggg cgggattatg    14700
tgcgctcttc caacaagctt gtcttttggaa aatagatcaa tttcccttgg acgcgagaag    14760
gttgttcgaa cagaaacctt ttatctagtt aaagggaacc gaagaagatt tttagcacag    14820
caaggggcag gatgttcaac tgtgagaaaa cttcttctaa aaatcgtgtc gttccccgtc    14880
ctacaagttg acactctttt cgaagaatta gccaaaaaac ttccagtaag cctgcaaaaa    14940
aaaaaaaaaa gcttcttaat cggttttttg aaggtcattc ggacgttttt tttttttttt    15000
ataaaagcta agtttctata aatgttctgt aaatgtaaaa cagaaggtaa tattttcgat    15060
tcaaagatat ttacaagaca tttacatttt gtcttccatt gtcaactgca cctaataaaa    15120
atcacttaat agcaatgtgc tgtgtcagtt cagttgacgt ggattatttt tagtgaatta    15180
tcgttacacg acacagtcaa gtttattgga accacacccg gtacacatcc tgtccagcat    15240
ttgcagtgcg caaataacct tggtgtgggc catgtgtagg acaggtcgta aacgtcacgc    15300
tgcattgaat tattgtgctg gctagacttc atggcgcctg gcaccgaatc acgtaactta    15360
ataacacgac cgatctgaag taccgcggac cgtggcttag ctgccttctc agcgaaaatg    15420
aataattgct ttgttggcaa gaaactaagc gacggaagag tcgcttttac ttattaacga    15480
aacaaccgtt ctttgattcg atcaatggga cgcgtgcaaa gcaccggcgg cggtagatgc    15540
ggggtaagta tagttaccct gcgcacgttt cgtggccgcc gccatctacg ccccattcat    15600 ctgaattta attcgaccta tcccggtaaa gcgaaagcga cacgcttttt gacttaaaat    15660
taagctggat agggccattt cgctttcgct gtgcgaaaaa tttcacacat agcgggaccg    15720
aacacgttat aagtatcgat taggtctatt aaagtgtgta tcgccctggc ttgtgcaata    15780
ttcatagcta atccagataa tttgtctctc tgtcggaacc agaactggta aaagtttcca    15840
ttgcgtctgg aaacagagag acagccttgg tcttgaccat tttcaaaggt aacgcagacc    15900
gcttgtctat cattgcgtct ctatggtttt tggaggatta gacggggcca cgaacagata    15960
gtaacgcaga gataccaaaa acctcctaat ctgccccggt ccagtaatgg tgcatagcgg    16020
atgtctgtac cgccatcggt gcaccgatat ggtcattacc acgtatcgcc tacagacatg    16080
gcggtagcca cgtggctata aggtttgggg ctccccaagg gactgctggg atgacagctt    16140
catattatat tccaaacccc gagggggttcc ctgacgaccc tactgtcgaa gtataatata    16200
tgaatgggcg cataatcagc ttaattggtg aggacaagct acaagttgta acttacccgc    16260
gtattagtcg aattaaccac tcctgttcga tgttcaacat acctgatctc cacaaagtac    16320
gttgccggtc ggggtcaaac cgtcttcggt tggactagag gtgtttcatg caacggccag    16380
```

```
ccccagtttg gcagaagcca gctcgaaacc gccttaaact acagacaggt cccagccaag   16440
taggcggatc cgagctttgg cggaatttga tgtctgtcca gggtcggttc atccgcctag   16500
aaaacctcaa aaaggcggga gccaatcaaa atgcagcatt atattttaag ttttggagtt   16560
tttccgccct cggttagttt tacgtcgtaa tataaaattc ctcaccgaaa ccggtaagta   16620
aagactatgt attttttccc agtgaataat gagtggcttt ggccattcat ttctgataca   16680 taaaaaggg tcacttatta tgttgttaac tataaaaagc gtcatggcaa acgataaagg   16740
tagcaattgg acaacaattg atattttcg cagtaccgtt tgctatttcc atcgttaacc   16800
gattcgggct tgggatgctc atatctgctg actgaggcag aatgtgaaag ctaagcccga   16860
accctacgag tatagacgac tgactccgtc ttacactttc tgacaaagag aatgaggaac   16920
ccggggcagg tgtagaactg tctgtggaat actgtttctc ttactccttg ggccccgtcc   16980
acatcttgac agacaccta ctgatcggta tgatagccag gatgaggatt tgttgacaa   17040 tgcatcagtc gactagccat actatcggtc ctactcctaa aacaactgtt acgtagtcag   17100
tttcagggaa atcacctgga ggtcttccag gcattagaga aaaaggcggg aaagtccctt   17160
tagtggacct ccagaaggtc cgtaatctct ttttccgccc tgaggagcag attttaaatt   17220
tgaaaagaaa agtattgggg agttcgcaaa actcctcgtc taaaatttaa acttttcttt   17280
tcataacccc tcaagcgttt acagcagcgg ttccgaagca tctgaaactc cagttaaaag   17340
acggaaatca tgtcgtcgcc aaggcttcgt agactttgag gtcaattttc tgcctttagt   17400
ggagcaaagc gaagattatt tgctgaaaat gaagctaacc gtgttcttac cctcgtttcg   17460
cttctaataa acgactttta cttcgattgg cacaagaatg gcccctccag gtacaggggg   17520
agggggaggg gaggcaagaa cttaatgagg cggggaggtc catgtccccc tcccctccc   17580 ctccgttctt gaattactcc agcaggcaat tagtcatcta catctgcagc ttgttaaatc   17640
taaaaatgct tcgtccgtta atcagtagat gtagacgtcg aacaatttag attttttacga  17700 acagttttta agctggggct cttaaatct ttgttccttt gtagcttcca tgtcaaaaat   17760
tcgaccccga gaaatttaga aacaaggaaa catcgaaggt tgatattacg aggttgttta   17820
agaatgataa gaccactaat cagcaatggg actataatgc tccaacaaat tcttactatt   17880
ctggtgatta gtcgttaccc tgctggctgt gtttggcctt gcagaggtgt ttttttgaggc  17940 gagtttcgaa acgaccgaca caaaccggaa cgtctccaca aaaaactccg ctcaaagctt   18000
ctcctaaaga agcagtgtag ttttctgcag atgcaaaaaa gatctcatga gaggatttct   18060
tcgtcacatc aaaagacgtc tacgtttttt ctagagtact aggaggaact tgtgcagttt   18120
acttaatctg ctttaacaca gctaaaagca tcctccttga acacgtcaaa tgaattagac   18180
gaaattgtgt cgatttcgt gagaaacagt ccggaatctg atggcaaaca tgctaaatgt   18240
aagagaagag ctcttttgtca ggccttagac taccgtttgt acgatttaca ttctcttctc   18300
tgtttgatgc tgcagccacc taaaattcga ggactcagcg cagctctatt acaaactacg   18360
acgtcggtgg attttaagct cctgagtcgc gtcgagataa ctggtttaaa agtagtttgt   18420
cacccgctac acttaaacat ggtgctttac gaccaaattt tcatcaaaca gtgggcgatg   18480
tgaatttgta ccacgaaatg ctgagtggat acgggcgcaa actactctga acgagagctt   18540
gcagaccgag gactcaccta tgcccgcgtt tgatgagact tgctctcgaa cgtctggctc   18600
aaattcgact tcggaactat ggtgcaatgg gcctatgatc acaaatatgc tttaagctga   18660
agccttgata ccacgttacc cggatactag tgtttatacg tgaggagtct aaaatagcct   18720
```

```
atgaatatgc tttggctgca ggatctgata actcctcaga ttttatcgga tacttatacg   18780
aaaccgacgt cctagactat gcaatgcacg ggcttttttta gcaactaaca gccaagctaa   18840
gcatgtgaag cgttacgtgc ccgaaaaaat cgttgattgt cggttcgatt cgtacacttc   18900
gactgtgcaa ctatggtaag acactatcta agagctgaaa cacaagcatt ctgacacgtt   18960
gataccattc tgtgatagat tctcgacttt gtgttcgtaa aagcatgcct gcatatatta   19020
aagctaggtg caagctggca actggggaag ttcgtacgga cgtatataat ttcgatccac   19080
gttcgaccgt tgaccccttc gaagctggaa gtctatccta actttttta actatcagaa   19140 tattgaatta cttcgacctt cagataggat tgaaaaaaat tgatagtctt ataacttaat   19200
attaccttta ttaatgcttt aaagctctgg ctaaaaggaa ttccaaaaaa taatggaaat   19260
aattacgaaa tttcgagacc gattttcctt aaggttttt aaactgttta gcatttattg   19320
gccctccaaa cacaggcaag tctatgctct tttgacaaat cgtaaataac cgggaggttt   19380
gtgtccgttc agatacgaga gcaactcatt aattcatttt ttgggtggta gtgttttatc   19440
ttttgccaac cgttgagtaa ttaagtaaaa aacccaccat cacaaaatag aaaacggttg   19500
cataaaagtc acttttggct tgcttccta gcagatacta gagctgcttt gtattttcag   19560
tgaaaaccga acgaagggat cgtctatgat ctcgacgaaa agtagatgat gctactcatg   19620
cttgctggag gtactttgac acatacctca tcatctacta cgatgagtac gaacgacctc   19680
catgaaactg tgtatggagt gaaatgcatt ggatggctac cctgtcagta ttgatagaaa   19740
acacaaagca ctttacgtaa cctaccgatg ggacagtcat aactatcttt tgtgtttcgt   19800
gcggttcaaa ttaaagctcc accctcctg gtaaccagta atattgatgt cgccaagttt   19860
aatttcgagg tggggaggac cattggtcat tataactaca gcaggcagag gacagatatt   19920
tgtacttgca tagtcgggtg caaaccttc cgtccgtctc ctgtctataa acatgaacgt   19980
atcagcccac gtttggaaag gctttgagca gccatgcaca gatgaatcgg gtgagcaacc   20040
ttttaatatt cgaaactcgt cggtacgtgt ctacttagcc cactcgttgg aaaattataa   20100
actgatgcag attggaaatc ttttttttgta aggttatggg ggcgtttaga tgactacgtc   20160
taacctttag aaaaaaacat tccaataccc ccgcaaatct cctgattgac gaggaggagg   20220
atagtgaaga ggatggagac agcatgcgaa ggactaactg ctcctcctcc tatcacttct   20280
cctacctctg tcgtacgctt cgtttacatg cagcgcaaga aacacaaatg cagttgattg   20340
agaaaagtag gcaaatgtac gtcgcgttct ttgtgtttac gtcaactaac tcttttcatc   20400
tgataagttg caagatcata tactgtactg gactgctgtt agaactgaga actattcaac   20460
gttctagtat atgacatgac ctgacgacaa tcttgactct acacactgct ttatgctgca   20520
aggaaaaaag gggtgactgt cctaggacac tgtgtgacga aatacgacgt tccttttttc   20580
cccactgaca ggatcctgtg tgcagagtac cacactctgt agtttgtcaa gagagagcca   20640
agcaggccat acgtctcatg gtgtgagaca tcaaacagtt ctctctcggt tcgtccggta   20700
tgaaatgcag ttgtctttgc aggagttaag caaaactgag tttggggatg actttacgtc   20760
aacagaaacg tcctcaattc gttttgactc aaaccctac aaccatggtc tttgcttgac   20820
acaagctggg accgatatat gtcagaacct tggtaccag aaacgaactg tgttcgaccc   20880
tggctatata cagtcttgga aaacggtgct ttaagaaagg cgccagggtg gtagaggtgg   20940
agtttgatgg tttgccacga aattctttcc gcggtcccac catctccacc tcaaactacc   21000
aaatgcaagc aatacaaact ggtacactgt ctacagcaat ttgtacatgc tttacgttcg   21060
ttatgtttga ccatgtgaca gatgtcgtta acatgtacg gcacagagga cggctggcag   21120
```

```
cttgcgaagg ctgggctgac ggaactgggc cgtgtctcct gccgaccgtc gaacgcttcc    21180
gacccgactg ccttgacccg tctactactg caccatggcc ggtgctggac gcatttacta    21240
ttctcgcttt agatgatgac gtggtaccgg ccacgacctg cgtaaatgat aagagcgaaa    21300
ggtgacgagg cagccagatt tagtacaaca gggcattact ctgtaagaga ccactgctcc    21360
gtcggtctaa atcatgttgt cccgtaatga gacattctct tcaggacaga gtgtatgctg    21420
gtgtctcatc cacctcttct gattttagag agtcctgtct cacatacgac cacagagtag    21480
gtggagaaga ctaaaatctc atcgcccaga cggagtctgg gtcgcatccg aaggacctga    21540
aggagaccct tagcgggtct gcctcagacc cagcgtaggc ttcctggact tcctctggga    21600
gcaggaaaag aagccgagcc agcccagcct gtctcttctt tgctcggctc cgtcctttc    21660 ttcggctcgg tcgggtcgga cagagaagaa acgagccgag ccccgcctgc ggtcccatca    21720
gagcaggcct cggttgggta cgggacggtc ggggcggacg ccagggtagt ctcgtccgga    21780
gccaacccat gccctgccag ctcgctcgca cccctacaat tttcctgcag gctcgggggg    21840
ctctattctc gagcgagcgt ggggatgtta aaaggacgtc cgagcccccc gagataagag    21900
cgctcttcct ccaccccgtg cagggcacgg taccggtgga cttggcatca gcgagaagga    21960
ggtggggcac gtcccgtgcc atggccacct gaaccgtagt aggcaggaag aagaggagca    22020
gtcgcccgac tccacagagg aagaaccagt tccgtccttc ttctcctcgt cagcgggctg    22080
aggtgtctcc ttcttggtca gactctccca aggcgcacca ccaatgatgg attccacctg    22140
ttaaaggcag ctgagagggt tccgcgtggt ggttactacc taaggtggac aatttccgtc    22200
gagggtcatg ctttgctcta atttcaggaa ctgctaacca ggtaaagtgc ctcccagtac    22260
gaaacgagat taaagtcctt gacgattggt ccatttcacg tatcgctttc gggtgaaaaa    22320
gaaccataga catcgctacg agaactgcac atagcgaaag cccacttttt cttggtatct    22380
gtagcgatgc tcttgacgtg caccacctgg ttcacagttg ctgacaacgg tgctgaaaga    22440
caaggacaag gtggtggacc aagtgtcaac gactgttgcc acgactttct gttcctgttc    22500
cacaaatact gatcacctt ggatcgccaa gtcaaaggca agactttctg gtgtttatga    22560
ctagtggaaa cctagcggtt cagtttccgt tctgaaagac aaacatgtac cactacctcc    22620
tggaatgaac atttccggct ttacagccag tttgtacatg gtgatggagg accttacttg    22680
taaaggccga aatgtcggtc cttggacttc tgatcactgc cattgccttt tcttcatctg    22740
actggtgtac gaacctgaag actagtgacg gtaacggaaa agaagtagac tgaccacatg    22800
tatgccaaat ctatgcgacc gcattataaa gccgaattct gcagatatcc atacggttta    22860
gatacgctgg cgtaatattt cggcttaaga cgtctatagg atcacactgg cggccatatg    22920
gccgctatgc ggtgtgaaat accgcacaga tagtgtgacc gccggtatac cggcgatacg    22980
ccacacttta tggcgtgtct tgcgtaagga gaaaataccg catcaggcgc tcttccgctt    23040
cctcgctcac acgcattcct ctttatggc gtagtccgcg agaaggcgaa ggagcgagtg    23100
tgactcgctg cgctcggtcg ttcggctgcg gcgagcggta tcagctcact actgagcgac    23160
gcgagccagc aagccgacgc cgctcgccat agtcgagtga caaaggcggt aatacggtta    23220
tccacagaat caggggataa cgcaggaaag gtttccgcca ttatgccaat aggtgtctta    23280
gtcccctatt gcgtcctttc aacatgtgag caaaaggcca gcaaaaggcc aggaaccgta    23340
aaaaggccgc ttgtacactc gttttccggt cgttttccgg tccttggcat ttttccggcg    23400
gttgctggcg ttttttccata ggctccgccc ccctgacgag catcacaaaa caacgaccgc    23460
```

```
aaaaaggtat ccgaggcggg gggactgctc gtagtgtttt atcgacgctc aagtcagagg    23520
tggcgaaacc cgacaggact ataaagatac tagctgcgag ttcagtctcc accgctttgg    23580
gctgtcctga tatttctatg caggcgtttc ccctggaag ctccctcgtg cgctctcctg    23640
ttccgaccct gtccgcaaag ggggaccttc gagggagcac gcgagaggac aaggctggga    23700
gccgcttacc ggatacctgt ccgccttttct cccttcggga agcgtggcgc cggcgaatgg    23760
cctatggaca ggcggaaaga gggaagccct tcgcaccgcg tttctcatag ctcacgctgt    23820
aggtatctca gttcggtgta ggtcgttcgc aaagagtatc gagtgcgaca tccatagagt    23880
caagccacat ccagcaagcg tccaagctgg gctgtgtgca cgaaccccc gttcagcccg    23940 accgctgcgc aggttcgacc cgacacacgt gcttgggggg caagtcgggc tggcgacgcg    24000
cttatccggt aactatcgtc ttgagtccaa cccggtaaga cacgacttat gaataggcca    24060
ttgatagcag aactcaggtt gggccattct gtgctgaata cgccactggc agcagccact    24120
ggtaacagga ttagcagagc gaggtatgta gcggtgaccg tcgtcggtga ccattgtcct    24180
aatcgtctcg ctccatacat ggcggtgcta cagagttctt gaagtggtgg cctaactacg    24240
gctacactag ccgccacgat gtctcaagaa cttcaccacc ggattgatgc cgatgtgatc    24300
aaggacagta tttggtatct gcgctctgct gaagccagtt accttcggaa ttcctgtcat    24360
aaaccataga cgcgagacga cttcggtcaa tggaagcctt aaagagttgg tagctcttga    24420
tccggcaaac aaaccaccgc tggtagcggt tttctcaacc atcgagaact aggccgtttg    24480
tttggtggcg accatcgcca ggttttttg tttgcaagca gcagattacg cgcagaaaaa    24540
aaggatctca ccaaaaaaac aaacgttcgt cgtctaatgc gcgtcttttt ttcctagagt    24600
agaagatcct ttgatctttt ctacggggtc tgacgctcag tggaacgaaa tcttctagga    24660
aactagaaaa gatgccccag actgcgagtc accttgcttt actcacgtta agggattttg    24720
gtcatgagat tatcaaaaag gatcttcacc tgagtgcaat tccctaaaac cagtactcta    24780 atagttttc ctagaagtgg tagatccttt taaattaaaa atgaagtttt aaatcaatct    24840
aaagtatata atctaggaaa atttaatttt tacttcaaaa tttagttaga tttcatatat    24900
tgagtaaact tggtctgaca gttaccaatg cttaatcagt gaggcaccta actcatttga    24960
accagactgt caatggttac gaattagtca ctccgtggat tctcagcgat ctgtctatttt   25020 cgttcatcca tagttgcctg actcccgtc agagtcgcta acagataaa gcaagtaggt    25080 atcaacggac tgaggggcag gtgtagataa ctacgatacg ggagggctta ccatctggcc    25140
ccagtgctgc cacatctatt gatgctatgc cctcccgaat ggtagaccgg ggtcacgacg    25200
aatgataccg cgagacccac gctcaccggc tccagattta tcagcaataa ttactatggc    25260
gctctgggtg cgagtggccg aggtctaaat agtcgttatt accagccagc cggaagggcc    25320
gagcgcagaa gtggtcctgc aactttatcc tggtcggtcg gccttccgg ctcgcgtctt    25380 caccaggacg ttgaaatagg gcctccatcc agtctattaa ttgttgccgg aagctagag    25440 taagtagttc cggaggtagg tcagataatt aacaacggcc cttcgatctc attcatcaag    25500
gccagttaat agtttgcgca acgttgttgc cattgctgca ggcatcgtgg cggtcaatta    25560
tcaaacgcgt tgcaacaacg gtaacgacgt ccgtagcacc tgtcacgctc gtcgtttggt    25620
atggcttcat tcagctccgg ttcccaacga acagtgcgag cagcaaacca taccgaagta    25680
agtcgaggcc aagggttgct tcaaggcgag ttacatgatc ccccatgttg tgcaaaaaag    25740
cggttagctc agttccgctc aatgtactag ggggtacaac acgttttttc gccaatcgag    25800
cttcggtcct ccgatcgttg tcagaagtaa gttggccgca gtgttatcac gaagccagga    25860
```

```
ggctagcaac agtcttcatt caaccggcgt cacaatagtg tcatggttat ggcagcactg   25920
cataattctc ttactgtcat gccatccgta agtaccaata ccgtcgtgac gtattaagag   25980
aatgacagta cggtaggcat agatgctttt ctgtgactgg tgagtactca accaagtcat   26040
tctgagaata tctacgaaaa gacactgacc actcatgagt tggttcagta agactcttat   26100
gtgtatgcgg cgaccgagtt gctcttgccc ggcgtcaaca cgggataata cacatacgcc   26160
gctggctcaa cgagaacggg ccgcagttgt gccctattat ccgcgccaca tagcagaact   26220
ttaaaagtgc tcatcattgg aaaacgttct ggcgcggtgt atcgtcttga aattttcacg   26280
agtagtaacc ttttgcaaga tcggggcgaa aactctcaag gatcttaccg ctgttgagat   26340
ccagttcgat agccccgctt ttgagagttc ctagaatggc gacaactcta ggtcaagcta   26400
gtaacccact cgtgcaccca actgatcttc agcatctttt actttcacca cattgggtga   26460
gcacgtgggt tgactagaag tcgtagaaaa tgaaagtggt gcgtttctgg gtgagcaaaa   26520
acaggaaggc aaaatgccgc aaaaaaggga cgcaaagacc cactcgtttt tgtccttccg   26580
ttttacggcg ttttttccct ataagggcga cacggaaatg ttgaatactc atactcttcc   26640
tttttcaata tattcccgct gtgcctttac aacttatgag tatgagaagg aaaaagttat   26700
ttattgaagc atttatcagg gttattgtct catgagcgga tacatatttg aataacttcg   26760
taaatagtcc caataacaga gtactcgcct atgtataaac aatgtattta gaaaaataaa   26820
caaataggg  ttccgcgcac atttccccga ttacataaat cttttttattt gtttatcccc   26880
aaggcgcgtg taaggggct  aaagtgccac ctgacgtcta agaaaccatt attatcatga   26940
cattaaccta tttcacggtg gactgcagat tctttggtaa taatagtact gtaattggat   27000
taaaaatagg cgtatcacga ggccctttcg tcttcaagaa ttctcatgtt attttttatcc   27060
gcatagtgct ccgggaaagc agaagttctt aagagtacaa tgacagctta tcatcgataa   27120
gcttcacgct gccgcaagca ctcagggcgc actgtcgaat agtagctatt cgaagtgcga   27180
cggcgttcgt gagtcccgcg aagggctgct aaaggaagcg gaacacgtag aaagccagtc   27240
cgcagaaacg ttcccgacga tttccttcgc cttgtgcatc tttcggtcag gcgtctttgc   27300
gtgctgaccc cggatgaatg tcagctactg ggctatctgg acaagggaaa cacgactggg   27360
gcctacttac agtcgatgac ccgatagacc tgttccctttt acgcaagcgc aaagagaaag   27420
caggtagctt gcagtgggct tacatggcga tgcgttcgcg tttctctttc gtccatcgaa   27480
cgtcacccga atgtaccgct tagctagact gggcggtttt atggacagca agcgaaccgg   27540
aattgccagc atcgatctga cccgccaaaa tacctgtcgt tcgcttggcc ttaacggtcg   27600
tggggcgccc tctggtaagg ttgggaagcc ctgcaaagta aactggatgg accccgcggg   27660
agaccattcc aacccttcgg gacgtttcat ttgacctacc ctttcttgcc gccaaggatc   27720
tgatggcgca ggggatcaag atcctgcttc gaaagaacgg cggttcctag actaccgcgt   27780
ccctagttc  taggacgaag atccccgtgg cccgttgctc gcgtttgctg gcggtgtccc   27840
cggaagaaat tagggggcacc gggcaacgag cgcaaacgac cgccacaggg gccttcttta   27900
atatttgcat gtctttagtt ctatgatgac acaaaccccg cccagcgtct tataaacgta   27960
cagaaatcaa gatactactg tgtttgggc  gggtcgcaga tgtcattggc gaattcgaac   28020
acgcagatgc agtcggggcg gcgcggtccc acagtaaccg cttaagcttg tgcgtctacg   28080
tcagccccgc cgcgccaggg aggtccactt cgcatattaa ggtgacgcgt gtggcctcga   28140
acaccgagcg tccaggtgaa gcgtataatt ccactgcgca caccggagct tgtggctcgc   28200
```

```
accctgcagc gacccgctta acagcgtcaa cagcgtgccg cagatctgat tgggacgtcg   28260
ctgggcgaat tgtcgcagtt gtcgcacggc gtctagacta caagagacag gatgaggatc   28320
gtttcgcatg attgaacaag atggattgca gttctctgtc ctactcctag caaagcgtac   28380
taacttgttc tacctaacgt cgcaggttct ccggccgctt gggtggagag gctattcggc   28440
tatgactggg gcgtccaaga ggccggcgaa cccacctctc cgataagccg atactgaccc   28500
cacaacagac aatcggctgc tctgatgccg ccgtgttccg gctgtcagcg gtgttgtctg   28560
ttagccgacg agactacggc ggcacaaggc cgacagtcgc caggggcgcc cggttctttt   28620
tgtcaagacc gacctgtccg gtgccctgaa gtccccgcgg gccaagaaaa acagttctgg   28680
ctggacaggc cacgggactt tgaactgcag gacgaggcag cgcggctatc gtggctggcc   28740
acgacgggcg acttgacgtc ctgctccgtc gcgccgatag caccgaccgg tgctgcccgc   28800
ttccttgcgc agctgtgctc gacgttgtca ctgaagcggg aagggactgg aaggaacgcg   28860
tcgacacgag ctgcaacagt gacttcgccc ttccctgacc ctgctattgg gcgaagtgcc   28920
ggggcaggat ctcctgtcat ctcaccttgc gacgataacc cgcttcacgg ccccgtccta   28980
gaggacagta gagtggaacg tcctgccgag aaagtatcca tcatggctga tgcaatgcgg   29040
cggctgcata aggacggctc tttcataggt agtaccgact acgttacgcc gccgacgtat   29100
cgcttgatcc ggctacctgc ccattcgacc accaagcgaa acatcgcatc gcgaactagg   29160
ccgatggacg ggtaagctgg tggttcgctt tgtagcgtag gagcgagcac gtactcggat   29220
ggaagccggt cttgtcgatc aggatgatct ctcgctcgtg catgagccta ccttcggcca   29280
gaacagctag tcctactaga ggacgaagag catcaggggc tcgcgccagc cgaactgttc   29340
gccaggctca cctgcttctc gtagtccccg agcgcggtcg gcttgacaag cggtccgagt   29400
aggcgcgcat gcccgacggc gaggatctcg tcgtgaccca tggcgatgcc tccgcgcgta   29460
cgggctgccg ctcctagagc agcactgggt accgctacgg tgcttgccga atatcatggt   29520
ggaaaatggc cgcttttctg gattcatcga acgaacggct tatagtacca cctttttaccg  29580 gcgaaaagac ctaagtagct ctgtggccgg ctgggtgtgg cggaccgcta tcaggacata   29640
gcgttggcta gacaccggcc gacccacacc gcctggcgat agtcctgtat cgcaaccgat   29700
cccgtgatat tgctgaagag cttggcggcg aatgggctga ccgcttcctc gggcactata   29760
acgacttctc gaaccgccgc ttacccgact ggcgaaggag gtgctttacg gtatcgccgc   29820
tcccgattcg cagcgcatcg ccttctatcg cacgaaatgc catagcggcg agggctaagc   29880
gtcgcgtagc ggaagatagc ccttcttgac gagttcttct gagcgggact ctggggttcg   29940
aaatgaccga ggaagaactg ctcaagaaga ctcgccctga daccccaagc tttactggct   30000
ccaagcgacg cccaacctgc catcacgaga tttcgattcc accgccgcct ggttcgctgc   30060
gggttggacg gtagtgctct aaagctaagg tggcggcgga tctatgaaag gttgggcttc   30120
ggaatcgttt tccgggacgc cggctggatg agatactttc caacccgaag ccttagcaaa   30180
aggccctgcg gccgacctac atcctccagc gcggggatct catgctggag ttcttcgccc   30240
accccgggag taggaggtcg cgcccctaga gtacgacctc aagaagcggg tggggccctc   30300 atggggagg ctaactgaaa cacgaaggaa gacaataccg gaaggaaccc tacccctcc     30360 gattgacttt gtgccttcct ctgttatggc cttccttggg gcgctatgaa cggcaataaa   30420
aagacagaat aaaacgcacg gtgttgggtc cgcgatactt gccgttattt ttctgtctta   30480
ttttgcgtgc cacaacccag gtttgttcat aaacgcgggg ttcggtccca gggctggcac   30540
tctgtcgata caaacaagta tttgcgcccc aagccagggt cccgaccgtg agacagctat   30600
```

-continued

```
cccaccgag acccccattgg ggccaatacg cccgcgtttc ttcctttttcc ggggtggctc    30660 tggggtaacc ccggttatgc gggcgcaaag aaggaaaagg ccaccccacc ccccaagttc    30720
gggtgaaggc ccagggctcg cagccaacgt ggtggggtgg ggggttcaag cccacttccg    30780
ggtcccgagc gtcggttgca cggggcggca agccctgcca tagccacggg ccccgtgggt    30840
tagggacggc gccccgccgt tcgggacggt atcggtgccc ggggcaccca atccctgccg    30900
ggatcgcggc ccctagcgc cggg                                            30924
```

<210> SEQ ID NO 2
<211> LENGTH: 288
<212> TYPE: PRT
<213> ORGANISM: Homo sapiens
<220> FEATURE:
<223> OTHER INFORMATION: B7.1 (CD80) protein sequence

<400> SEQUENCE: 2

```
Met Gly His Thr Arg Arg Gln Gly Thr Ser Pro Ser Lys Cys Pro Tyr
  1               5                  10                  15

Leu Asn Phe Phe Gln Leu Leu Val Leu Ala Gly Leu Ser His Phe Cys
             20                  25                  30

Ser Gly Val Ile His Val Thr Lys Glu Val Lys Glu Val Ala Thr Leu
         35                  40                  45

Ser Cys Gly His Asn Val Ser Val Glu Glu Leu Ala Gln Thr Arg Ile
     50                  55                  60

Tyr Trp Gln Lys Glu Lys Lys Met Val Leu Thr Met Met Ser Gly Asp
 65                  70                  75                  80

Met Asn Ile Trp Pro Glu Tyr Lys Asn Arg Thr Ile Phe Asp Ile Thr
                 85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285
```

<210> SEQ ID NO 3

<211> LENGTH: 365
<212> TYPE: PRT
<213> ORGANISM: Homo sapiens
<220> FEATURE:
<223> OTHER INFORMATION: HLA A1 protein sequence

<400> SEQUENCE: 3

```
Met Ala Val Met Ala Pro Arg Thr Leu Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
    50                  55                  60

Ala Ser Gln Lys Met Glu Pro Arg Ala Pro Trp Ile Glu Gln Glu Gly
65                  70                  75                  80

Pro Glu Tyr Trp Asp Gln Glu Thr Arg Asn Met Lys Ala His Ser Gln
                85                  90                  95

Thr Asp Arg Ala Asn Leu Gly Thr Leu Arg Gly Tyr Tyr Asn Gln Ser
            100                 105                 110

Glu Asp Gly Ser His Thr Ile Gln Ile Met Tyr Gly Cys Asp Val Gly
            115                 120                 125

Pro Asp Gly Arg Phe Leu Arg Gly Tyr Arg Gln Asp Ala Tyr Asp Gly
    130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Lys Arg Lys Trp Glu Ala Ala His Ala
                165                 170                 175

Ala Glu Gln Arg Arg Val Tyr Leu Asp Gly Arg Cys Val Asp Gly Leu
            180                 185                 190

Arg Arg Tyr Leu Glu Asn Gly Lys Glu Thr Leu Gln Arg Thr Asp Pro
            195                 200                 205

Pro Lys Thr His Met Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Leu Ser Ser Gln Pro
    290                 295                 300

Thr Ile Pro Ile Val Gly Ile Ile Ala Gly Leu Val Leu Leu Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Thr Gln Ala Ala Ser Ser Asp Ser
            340                 345                 350

Ala Gln Gly Ser Asp Val Ser Leu Thr Ala Cys Lys Val
            355                 360                 365
```

<210> SEQ ID NO 4

<211> LENGTH: 605
<212> TYPE: PRT
<213> ORGANISM: Bovine papillomavirus
<220> FEATURE:
<223> OTHER INFORMATION: E1 protein sequence

<400> SEQUENCE: 4

Met Ala Asn Asp Lys Gly Ser Asn Trp Asp Ser Gly Leu Gly Cys Ser
1               5                   10                  15

Tyr Leu Leu Thr Glu Ala Glu Cys Glu Ser Asp Lys Glu Asn Glu Glu
            20                  25                  30

Pro Gly Ala Gly Val Glu Leu Ser Val Glu Ser Asp Arg Tyr Asp Ser
        35                  40                  45

Gln Asp Glu Asp Phe Val Asp Asn Ala Ser Val Phe Gln Gly Asn His
    50                  55                  60

Leu Glu Val Phe Gln Ala Leu Glu Lys Lys Ala Gly Glu Glu Gln Ile
65                  70                  75                  80

Leu Asn Leu Lys Arg Lys Val Leu Gly Ser Ser Gln Asn Ser Ser Gly
                85                  90                  95

Ser Glu Ala Ser Glu Thr Pro Val Lys Arg Arg Lys Ser Gly Ala Lys
            100                 105                 110

Arg Arg Leu Phe Ala Glu Asn Glu Ala Asn Arg Val Leu Thr Pro Leu
        115                 120                 125

Gln Val Gln Gly Glu Gly Glu Gly Arg Gln Glu Leu Asn Glu Glu Gln
    130                 135                 140

Ala Ile Ser His Leu His Leu Gln Leu Val Lys Ser Lys Asn Ala Thr
145                 150                 155                 160

Val Phe Lys Leu Gly Leu Phe Lys Ser Leu Phe Leu Cys Ser Phe His
                165                 170                 175

Asp Ile Thr Arg Leu Phe Lys Asn Asp Lys Thr Thr Asn Gln Gln Trp
            180                 185                 190

Val Leu Ala Val Phe Gly Leu Ala Glu Val Phe Phe Glu Ala Ser Phe
        195                 200                 205

Glu Leu Leu Lys Lys Gln Cys Ser Phe Leu Gln Met Gln Lys Arg Ser
    210                 215                 220

His Glu Gly Gly Thr Cys Ala Val Tyr Leu Ile Cys Phe Asn Thr Ala
225                 230                 235                 240

Lys Ser Arg Glu Thr Val Arg Asn Leu Met Ala Asn Met Leu Asn Val
                245                 250                 255

Arg Glu Glu Cys Leu Met Leu Gln Pro Pro Lys Ile Arg Gly Leu Ser
            260                 265                 270

Ala Ala Leu Phe Trp Phe Lys Ser Ser Leu Ser Pro Ala Thr Leu Lys
        275                 280                 285

His Gly Ala Leu Pro Glu Trp Ile Arg Ala Gln Thr Thr Leu Asn Glu
    290                 295                 300

Ser Leu Gln Thr Glu Lys Phe Asp Phe Gly Thr Met Val Gln Trp Ala
305                 310                 315                 320

Tyr Asp His Lys Tyr Ala Glu Glu Ser Lys Ile Ala Tyr Glu Tyr Ala
                325                 330                 335

Leu Ala Ala Gly Ser Asp Ser Asn Ala Arg Ala Phe Leu Ala Thr Asn
            340                 345                 350

Ser Gln Ala Lys His Val Lys Asp Cys Ala Thr Met Val Arg His Tyr
        355                 360                 365

Leu Arg Ala Glu Thr Gln Ala Leu Ser Met Pro Ala Tyr Ile Lys Ala
    370                 375                 380

Arg Cys Lys Leu Ala Thr Gly Glu Gly Ser Trp Lys Ser Ile Leu Thr
385                 390                 395                 400

Phe Phe Asn Tyr Gln Asn Ile Glu Leu Ile Thr Phe Ile Asn Ala Leu
                405                 410                 415

Lys Leu Trp Leu Lys Gly Ile Pro Lys Lys Asn Cys Leu Ala Phe Ile
            420                 425                 430

Gly Pro Pro Asn Thr Gly Lys Ser Met Leu Cys Asn Ser Leu Ile His
        435                 440                 445

Phe Leu Gly Gly Ser Val Leu Ser Phe Ala Asn His Lys Ser His Phe
    450                 455                 460

Trp Leu Ala Ser Leu Ala Asp Thr Arg Ala Ala Leu Val Asp Asp Ala
465                 470                 475                 480

Thr His Ala Cys Trp Arg Tyr Phe Asp Thr Tyr Leu Arg Asn Ala Leu
                485                 490                 495

Asp Gly Tyr Pro Val Ser Ile Asp Arg Lys His Lys Ala Ala Val Gln
            500                 505                 510

Ile Lys Ala Pro Pro Leu Leu Val Thr Ser Asn Ile Asp Val Gln Ala
        515                 520                 525

Glu Asp Arg Tyr Leu Tyr Leu His Ser Arg Val Gln Thr Phe Arg Phe
    530                 535                 540

Glu Gln Pro Cys Thr Asp Glu Ser Gly Glu Gln Pro Phe Asn Ile Thr
545                 550                 555                 560

Asp Ala Asp Trp Lys Ser Phe Phe Val Arg Leu Trp Gly Arg Leu Asp
                565                 570                 575

Leu Ile Asp Glu Glu Asp Ser Glu Asp Gly Asp Ser Met Arg
            580                 585                 590

Thr Phe Thr Cys Ser Ala Arg Asn Thr Asn Ala Val Asp
        595                 600                 605

<210> SEQ ID NO 5
<211> LENGTH: 187
<212> TYPE: PRT
<213> ORGANISM: Bovine papillomavirus
<220> FEATURE:
<223> OTHER INFORMATION: E2 protein sequence

<400> SEQUENCE: 5

Met Glu Thr Ala Cys Glu Arg Leu His Ala Ala Gln Glu Thr Gln Met
1               5                   10                  15

Gln Leu Ile Glu Lys Ser Ser Asp Lys Leu Gln Asp His Ile Leu Tyr
            20                  25                  30

Trp Thr Ala Val Arg Thr Glu Asn Thr Leu Leu Tyr Ala Ala Arg Lys
        35                  40                  45

Lys Gly Val Thr Val Leu Gly His Cys Arg Val Pro His Ser Val Val
    50                  55                  60

Cys Gln Glu Arg Ala Lys Gln Ala Ile Glu Met Gln Leu Ser Leu Gln
65                  70                  75                  80

Glu Leu Ser Lys Thr Glu Phe Gly Asp Glu Pro Trp Ser Leu Leu Asp
                85                  90                  95

Thr Ser Trp Asp Arg Tyr Met Ser Glu Pro Lys Arg Cys Phe Lys Lys
            100                 105                 110

Gly Ala Arg Val Val Glu Val Glu Phe Asp Gly Asn Ala Ser Asn Thr
        115                 120                 125

Asn Trp Tyr Thr Val Tyr Ser Asn Leu Tyr Met Arg Thr Glu Asp Gly
    130                 135                 140

-continued

Trp Gln Leu Ala Lys Ala Gly Leu Thr Glu Leu Gly Ser Thr Thr Ala
145                 150                 155                 160

Pro Trp Pro Val Leu Asp Ala Phe Thr Ile Leu Ala Leu Val Thr Arg
            165                 170                 175

Gln Pro Asp Leu Val Gln Gln Gly Ile Thr Leu
            180                 185

<210> SEQ ID NO 6
<211> LENGTH: 286
<212> TYPE: PRT
<213> ORGANISM: Escherichia coli
<220> FEATURE:
<223> OTHER INFORMATION: Beta-lactamase protein sequence

<400> SEQUENCE: 6

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 7
<211> LENGTH: 264
<212> TYPE: PRT
<213> ORGANISM: Escherichia coli

```
<220> FEATURE:
<223> OTHER INFORMATION: G418 resistance gene protein sequence

<400> SEQUENCE: 7

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
        50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
        130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
                180                 185                 190

Leu Pro Asn Ile Met Val Glu Asn Gly Arg Phe Ser Gly Phe Ile Asp
            195                 200                 205

Cys Gly Arg Leu Gly Val Ala Asp Arg Tyr Gln Asp Ile Ala Leu Ala
        210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
                260
```

TUMOR VACCINE

RELATED APPLICATIONS

This application is a continuation of U.S. application Ser. No. 12/580,554 filed Oct. 16, 2009 which claims the benefit of priority to U.S. Provisional Application No. 61/106,355, filed on Oct. 17, 2008, and is a continuation-in-part application of U.S. Non-Provisional application Ser. No. 10/950,157, filed Sep. 24, 2004, which claims benefit of priority to U.S. Provisional Application No. 60/506,656, filed Sep. 26, 2003, each of which is incorporated by reference herein in its entirety.

STATEMENT REGARDING GOVERNMENT SUPPORT

This invention was made with government support under Grant Number CA39201-14 awarded by the National Institutes of Health. The government has certain rights in this invention.

FIELD OF THE INVENTION

The invention relates to the fields of medicine, immunology, and oncology. More specifically, the invention relates to methods and compositions for inducing an immune response against a tumor in an animal subject.

BACKGROUND OF THE INVENTION

Lung cancer is the most common cause of death due to cancer in the United States. For 2002, the American Cancer Society predicted that almost 170,000 new cases of lung cancer would be diagnosed and that 155,000 people would die from the disease. Patients with locally advanced or metastatic non-small cell lung cancer (NSCLC) make up 70% of the newly diagnosed cases.

Current recommendations for patients with inoperable disease include platinum-based chemotherapy plus radiation therapy in locally advanced disease, or chemotherapy alone in patients with metastases. Typical response rates are between 15% to 30%, with median survivals of less than one year. Meta-analysis of 52 phase III clinical trials randomizing metastatic NSCLC patients between best supportive care and chemotherapy concluded that chemotherapy increases the chance of 1 year survival by 10% and the median survival by 6 weeks. A recent report from the Big Lung Trial group (BLT) reported similar results. The aggressiveness of NSCLC is thought to relate to its ability to evade the immune system perhaps by suppressing immune response priming by means of CD4 regulatory cells and/or by producing immunosuppressive cytokines such as TGF-$\beta$.

Thus, there exists the need to develop effective therapies to treat a tumor, including cancers such as lung cancer. The present invention satisfies this need and provides related advantages as well.

SUMMARY OF THE INVENTION

The invention provides a tumor cell, for example, a lung cancer cell or other tumor cells, genetically modified to express a nucleic acid encoding CD80 (B7.1) and a nucleic acid encoding an HLA antigen. The invention also provides a method of stimulating an immune response to a tumor, including a cancer tumor such as a lung cancer tumor, by administering an allogeneic lung cancer tumor cell genetically modified to express a nucleic acid encoding CD80 (B7.1) and a nucleic acid encoding an HLA antigen. The invention additionally provides a method of inhibiting a tumor, including a cancer such as lung cancer, by administering an allogeneic tumor cell, for example a cancer tumor cell such as a lung cancer tumor cell, genetically modified to express a nucleic acid encoding CD80 (B7.1) and a nucleic acid encoding an HLA antigen. According to some embodiments of the invention, the vaccine is administered more than once.

BRIEF DESCRIPTION OF THE DRAWINGS

FIG. 5A (top two panels) shows CD8 prior to immunization or at 6, 12 and 18 weeks after challenge with untransfected (AD wild type) vaccine cells or K562 control.

DETAILED DESCRIPTION

Figure 1A:
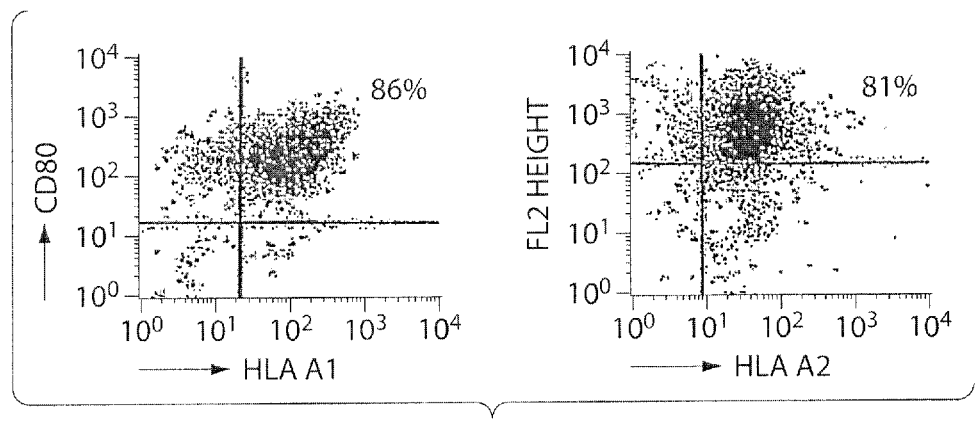
FIGS. 1A and B shows flow cytometry analysis. Panel A: Quality control of vaccine cells. Representative samples of vaccine cells coexpressing B7.1 (CD80) and HLA A1 (left panel) or HLA A2 (right panel) analyzed by flow cytometry. The percentage of double positive cells is indicated. CD80 and the HLA A allele must be coexpressed on 70% or more of the cells to qualify for immunization. Panel B. Patient CD8 cells purified for ELI-spot assays. Flow cytometry of a representative sample of patient CD8 (right panel) cells purified by negative selection and used for ELIspot analysis; the purity of cells is given in %. Left panel shows isotype control.

The invention relates to the discovery that administering allogeneic tumor cells expressing or caused to express CD80 (B7.1) and HLA antigens to cancer patients resulted in an anti-tumor immune response in the patients. More particularly, CD8-mediated immune responses were elicited in stage IIIB/IV NSCLC patients immunized several times with allogeneic NSCLC cells transfected with CD80 (B7.1) and HLA-A1 or A2. Immunization significantly increased the frequencies of interferon-Y-secreting CD8 T cells in all but one of the patients tested as discussed in more detail, below, in a clinical analysis of one set of patients, five of fourteen patients responded to immunization with stable disease or partial tumor regression. Further characterization was performed with additional patients.

Carcinoma of the lung is the leading cause of cancer death and the second most commonly occurring cancer in both men and women in the United States (Jemal, et al., CA Cancer J. Clin. 53: 5-43 (2003). Non-small-cell lung cancers (NSCLC) are considered to be minimally or nonimmunogenic, and may contain CD4 regulatory cells that suppress generation of cytotoxic lymphocytes (CTL) (Woo, et al., J. Immunol. 168: 4272-4276 (2002)). Although NSCLC has not been considered a good candidate for immunotherapy, the studies disclosed herein are based on the hypothesis that NSCLC is indeed suitable for successful vaccine therapy because the tumor cells have not been exposed to immune attack and have not yet developed resistance mechanisms.

Immunotherapy trials for lung cancer have previously yielded no consistent benefit in humans (Ratto, et al., Cancer 78: 244-251 (1996); Lissoni, et al., Tumori80: 464-467 (1994); Ratto, et al., J. Immunother 23: 161-167 (2000)). Vaccine trials with B7.1 (CD80) transfected allogeneic or autologous cells have not been reported in patients with NSCLC prior to the studies disclosed herein, although similar vaccines have shown good activity in other human studies (Antonia, et al., J. Urol. 167: 1995-2000 (2002); Horig, et al., Cancer Immunol. Immunother. 49: 504-514 (2000); Hull, et al., Clin. Cancer. Res. 6: 4101-4109 (2000); von Mehren, et al., Clin. Cancer Res. 6: 2219-2228 (2000)). The objectives of the studies disclosed herein were to assess the safety, immunogenicity, and clinical response to an allogeneic whole cell tumor vaccine transfected with CD80 and HLA A1 or A2 administered to patients with advanced metastatic NSCLC. Disclosed herein are results on vaccine safety, clinical response, and overall survival.

As disclosed herein, to determine whether CD8 mediated immune responses could be elicited in stage IIIB/IV NSCLC patients, initially fourteen subjects were immunized several times with allogeneic NSCLC cells transfected with CD80 (B7.1) and HLA-A1 or A2. Additional patients were added. Patients enrolled were matched or unmatched at the HLA A1 or A2 locus and their immune response compared. Immunization significantly increased the frequencies of interferon-γ secreting CD8 T cells in all but one patient in response to ex vivo challenge with NSCLC cells. The CD8 response of matched and unmatched patients was not statistically different. NSCLC reactive CD8 cells did not react to IL562. Clinically, five of fourteen patients responded to immunization with stable disease or partial tumor regression. The study demonstrates that CD8IFN-γ responses against non-immunogenic or immunosuppressive tumors can be evoked by cellular vaccines even at advanced stages of disease. The positive clinical outcome suggests that non immunogenic tumors may be highly susceptible to immune effector cells generated by immunization.

Thus, it has been discovered that the administration to a tumor patient of modified tumor cells expressing CD80 and an HLA antigen results in desirable therapeutic effects. Hence, in one embodiment, the invention provides a tumor lung cancer cell into which has been introduced a first nucleic acid encoding CD80 and a second nucleic acid encoding HLA antigen. These modified tumor cells can be administered more than once. The modified tumor cells can be administered 2, 3, 4, 5, 6, 7, 8, 9, 10, 11, 12, 13, 14, 15, 16, 17, 18, 19 or 20 times. Preferably, the vaccine is administered between 2 and 9 times.

As used in this specification, the singular forms "a," "an" and "the" specifically also encompass the plural forms of the terms to which they refer, unless the content clearly dictates otherwise. As used herein, unless specifically indicated otherwise, the word "or" is used in the "inclusive" sense of "and/or" and not the "exclusive" sense of "either/or." In the specification and the appended claims, the singular forms include plural referents unless the context clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. As used in this specification, whether in a transitional phrase or in the body of the claim, the terms "comprise (s)" and "comprising" are to be interpreted as having an open-ended meaning That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "tumor" is used to denote neoplastic growth which may be benign (e.g., a tumor which does not form metastases and destroy adjacent normal tissue) or malignant/cancer (e.g., a tumor that invades surrounding tissues, and is usually capable of producing metastases, may recur after attempted removal, and is likely to cause death of the host unless adequately treated) (see Steadman's Medical Dictionary, 26th Ed, Williams & Wilkins, Baltimore, Md. (1995)).

The invention also provides a method of stabilizing or reversing a tumor load in a patient by administering to the patient an allogeneic tumor cell into which has been introduced a first nucleic acid encoding CD80 and a second nucleic acid encoding an HLA antigen.

In another embodiment, the invention provides a tumor cell, which can be a tumor cancer cell such as a lung cancer cell, genetically modified to express a nucleic acid encoding CD80 (B7.1) and a nucleic acid encoding an HLA antigen.

Exemplary HLA antigens include, but are not limited to, HLA A1, HLA A2, HLA A3, HLA A27, and the like. In a particular embodiment, the HLA antigen can be HLA A1 or HLA A2 (see Examples). One of skill in the art will appreciate that there are a number of different nucleic acid sequences encoding HLA antigens which may be used according to the invention without departing from the same (see below). Any suitable materials and/or methods known to those of skill can be utilized in carrying out the present invention. However, preferred materials and methods are described. Materials, reagents and the like to which reference is made in the following description and examples are obtainable from commercial sources, unless otherwise noted.

Technical and scientific terms used herein have the meaning commonly understood by one of skill in the art to which the present invention pertains, unless otherwise defined.

Reference is made herein to various methodologies and materials known to those of skill in the art. Standard reference works setting forth the general principles of recombinant DNA technology include for example, Ausubel et al., Current Protocols in Molecular Biology (Supplement 56), John Wiley & Sons, New York (2001); Sambrook and Russel, Molecular Cloning: A Laboratory Manual, 3rd ed., Cold Spring Harbor Press, Cold Spring Harbor (2001); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of pharmacology include Goodman and Gilman's The Pharmacological Basis of Therapeutics, 10th Ed., McGraw Hill Companies Inc., New York (2001). The compositions according to the invention are optionally formulated in a pharmaceutically acceptable vehicle with any of the well known pharmaceutically acceptable carriers, including diluents and excipients (see Remington's Pharmaceutical Sciences, 18th Ed., Gennaro, Mack Publishing Co., Easton, Pa. 1990 and Remington: The Science and Practice of Pharmacy, Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic. Formulations of compositions according to the invention may contain more than one type of compound of the invention), as well any other pharmacologically active ingredient useful for the treatment of the symptom/condition being treated.

In some embodiments, the cancer cell can be a lung tissue cancer cell (also referred to as "lung cancer cell") such as an adenocarcinoma cell type, for example, the lung cancer cell can be the AD 100 cell line, as exemplified hereinafter.

The invention additionally provides a method of stimulating an immune response to a tumor, for example, a cancer such as a lung cancer, in a patient by administering an allogeneic tumor cell genetically modified to express a nucleic acid encoding CD80 (B7.1) and a nucleic acid encoding an HLA antigen. The tumor cell can be a cancer cell, for example, a lung cancer tumor cell.

The methods of the present invention are intended for use with any subject that may experience the benefits of the methods of the invention. Thus, in accordance with the invention, "subjects", "patients" as well as "individuals" (used interchangeably) include humans as well as non-human subjects, particularly domesticated animals.

In one embodiment, a method of the invention can include matching the HLA antigen to the individual administered the tumor lung cancer cell. Methods of determining HLA haplotypes are well known to those skilled in the art, for example, using well known serological assays using antibodies to HLA alleles or the mixed lymphocyte reaction. In a particular embodiment, a method of the invention can be performed with the HLA antigen HLA A1, HLA A2, HLA A3 or HLA A27. The methods of the invention cause various tumor cells (e.g., lung cancer cells) including, for example, an adenocarcinoma such as the AD100 cell line exemplified hereinafter.

In still another embodiment, the invention provides a method of inhibiting a tumor by administering an allogeneic tumor cell genetically modified to express a nucleic acid encoding CD80 (B7.1) and a nucleic acid encoding an HLA antigen. The tumor can be, for example, a cancer tumor cell such as a lung cancer tumor cell. In certain embodiments, the tumor inhibited is lung cancer by the administration of an allogeneic cancer cell modified to express CD80 (B7.1) and an HLA antigen.

As used herein, an "allogeneic cell" refers to a cell that is not derived from the individual to which the cell is to be administered, that is, has a different genetic constitution than the individual. An allogeneic cell is generally obtained from the same species as the individual to which the cell is to be administered. For example, the allogeneic cell can be a human cell, as disclosed herein, for administering to a human patient such as a cancer patient. As used herein, an "allogeneic tumor cell" refers to a tumor cell that is not derived from the individual to which the allogeneic cell is to be administered.

Generally, the allogeneic tumor cell expresses one or more tumor antigens that can stimulate an immune response against a tumor in an individual to which the cell is to be administered. As used herein, an "allogeneic cancer cell," for example, a lung cancer cell, refers to a cancer cell that is not derived from the individual to which the allogeneic cell is to be administered. Generally, the allogeneic cancer cell expresses one or more tumor antigens that can stimulate an immune response against a cancer in an individual to which the cell is to be administered, for example, a lung cancer.

As used herein, a "genetically modified cell" refers to a cell that has been genetically modified to express an exogenous nucleic acid, for example, by transfection or transduction. A cell can be genetically modified to express, for example, a nucleic acid encoding CD80 (B7.1) and/or a nucleic acid encoding an HLA antigen, as disclosed herein. When a cell is to be genetically modified to express more than one polypeptide, for example, CD80 (B7.1) and an HLA antigen, it is understood that the polypeptides can be encoded on separate nucleic acids (see Example 1) or on the same nucleic acid, if desired. Methods of genetically modifying a cell are well known to those skilled in the art.

The invention provides methods and compositions for stimulating an immune response in a cancer patient. The compositions and methods are particularly useful for stimulating an immune response against non-immunogenic tumors. As used herein, a non-immunogenic tumor is a tumor that does not elicit a spontaneous immune response detectable, for example, by appreciable stimulation of CD8 T cells that produce interferon-γ (IFNγ) in tumor infiltrating lymphocytes (TILs).

Traditionally, melanoma and other immunogenic tumors have been preferred for treatment by immunotherapy. In the present invention, non-immunogenic tumors are considered good targets for active immunotherapy because the tumor cells have not been immuno-selected for evasion of the CTL response. Exemplary non-immunogenic tumors include, but are not limited to, lung, pancreatic, and the like.

A particularly useful nonimmunogenic tumor type is non small cell lung cancer (NSCLC), as exemplified herein. NSCLC tumors are good targets for active immunotherapy because they are non-immunogenic and do not spontaneously generate CTL responses. Therefore, NSCLC tumor cells have not developed evasive mechanisms towards cytotoxic T and natural killer (NK) cells, and NSCLC tumors are susceptible to cytotoxic attack. As disclosed herein, a composition of the invention was used to successfully slow tumor growth in NSCLC patients (see Examples II and III).

NSCLC tumors can also be genetically engineered to express and secrete gp96 and enhance the effectiveness of a vaccine because it combines adjuvant activity with polyvalent peptide specificity. Polyvalence prevents immunoselection and evasion. Tumor secreted gp96 activates dendritic cells (DC), natural killer cells (NK) and cytotoxic T lymphocytes (CTL), activating innate and adaptive immunity. Tumor cells can be killed by NK-specific mechanisms, by promiscuous killing of CD8 CTL through NKG2D, and by MHC restricted CD8 CTL activity. The activation of DC and NK by tumor secreted gp96 may also counteract the generation of immuno-suppressive CD4 regulatory cells found in NSCLC tumors. Tumor secreted gp96 stimulates, antigen cross presentation via the CD91 receptor on DC and macrophages. NSCLC are known to share tumor antigens also found in melanoma and may be endowed with additional shared antigens. Therefore allogeneic, gp96 secreting tumor cells used as vaccine are expected to generate immunity to the patient's autologous tumor. Similarly, a composition of the invention containing an allogeneic tumor cell expressing CD80 and an HLA antigen can generate immunity to the patient's autologous tumor.

Lung tumors prevent priming of CTL by regulatory cells, by TGF-P secretion and by down regulation of MHC class I. Therefore, immunogenic vaccines are needed to generate a CTL response. Lung tumors are susceptible to CTL killing because they have not been selected for CTL evasion. Lung tumor TIL contain large numbers of CD4 regulatory cells suppressing priming. In contrast, melanoma TIL contain antigen specific CD8 CTL whose killing activity has been blocked, indicating that priming has taken place already. As disclosed herein, lung cancer patients were successfully treated with a vaccine containing an allogeneic tumor cell genetically modified to express CD80 (B7.1) and an HLA antigen (Examples II and III). Thus, immunotherapy (vaccine therapy) of NSCLC is useful for treating this otherwise deadly disease.

As disclosed herein, an adenocarcinoma is an exemplary lung cancer that can be used in compositions and methods of the invention to express CD80 (B7.1) and an HLA antigen. Other types of lung cancer are well known, and cells derived from other types of lung cancers can be similarly used in compositions and methods of the invention. Exemplary lung cancers include, for example, non-small cell lung cancer, which can be adenocarcinoma, squamous cell carcinoma, or large cell carcinoma, small cell lung cancer, and carcinoids. One skilled in the art can readily obtain tissue samples from various types of lung cancers and generate a cell line useful for treating a lung cancer, using methods similar to those disclosed herein. Similarly, other types of nonimmunogenic tumors can be used to generate allogeneic tumor cells that can be genetically modified to express CD80 (B7.1) and an HLA antigen and used to treat a similar type of tumor or a tumor expressing similar types of tumor antigens.

An exemplary allogeneic tumor cell is the AD 100 cell line, which is a human lung adenocarcinoma cell line, as disclosed herein. Other lung cancer cell lines are well known to those skilled in the art and can be similarly used to generate an allogeneic cell genetically modified with CD80 (B7.1) and an HLA antigen. For example, numerous cell lines, including lung cancer cell lines are well known and available from the American Type Culture Collection (ATCC; Manassas Va.). Exemplary NSCLC cell lines include, but are not limited to, NCI-H2126[H2126] (ATCC CCL-256); NCI-H23 [H23] (ATCC CRL-5800); NCI-H1299[H1299] (ATCC CRL-5803); NCI-H358 [H358] (ATCC CRL-5807); NCI-H810 [H810] (ATCC CRL-5816); NCI-H522 [H522] (ATCC CRL-5810); NCI-H1155 [H1155] (ATCC CRL-5818); NCI-H647 [H647] (ATCC CRL-5834); NCI-H650 [H650] (ATCC CRL-5835); NCI-H838[H838] (ATCC CRL-5844); NCI-H920 [H920] (ATCC CRL-5850); NCI-H969 [H969] (ATCC CRL-5852); NCI-H1385 [H1385] (ATCC CRL-5867); NCI-H1435[H1435] (ATCC CRL-5870); NCI-H1437[H1437] (ATCC CRL-5872); NCI-H1563[H1563] (ATCC CRL-5875); NCI-H1568[H1568] (ATCC CRL-5876); NCI-H1581[H1581] (ATCC CRL-5878); NCI-H1623[H1623] (ATCC CRL-5881); NCI-H1651 [H1651] (ATCC CRL-5884); NCI-H1693[H1693] (ATCC CRL-5887); NCI-H1703[H1703] (ATCC CRL-5889); NCI-H1734[H1734] (ATCC CRL-5891); NCI-H1755[H1755] (ATCC CRL-5892); NCI-H1770 [H1770] (ATCC CRL-5893); NCI-H1793[H1793] (ATCC CRL-5896); NCI-H1838[H1838] (ATCC CRL-5899); NCI-H1869[H1869] (ATCC CRL-5900); NCI-H1915 [H1915] (ATCC CRL-5904); NCI-H1944[H1944] (ATCC CRL-5907); NCI-H1975[H1975] (ATCC CRL-5908); NCI-H1993 [H1993] (ATCC CRL-5909); NCI-H2023[H2023] (ATCC CRL-5912); NCI-H2030 [H2030] (ATCC CRL-5914); NCI-H2073 [H2073] (ATCC CRL-5918); NCI-H2085 [H2085] (ATCC CRL-5921); NCI-H2087 [H2087] (ATCC CRL-5922); NCI-H2106 [H2106] (ATCC CRL-5923); NCI-H2110 [H2110] (ATCC CRL-5924); NCI-H2135 [H2135] (ATCC CRL-5926); NCI-H2172[H2172] (ATCC CRL-5930); NCI-H2228 [H2228] (ATCC CRL-5935); NCI-H2291 [H2291] (ATCC CRL-5939); NCI-H2342 [H2342] (ATCC CRL-5941); NCI-H2347 [H2347] (ATCC CRL-5942); NCI-H2405 [H2405] (ATCC CRL-5944); NCI-H2444 [H2444] (ATCC CRL-5945); and NCI-H2122 [H2122] (ATCC CRL-5985). These and other tumor cell lines, particularly those of nonimmunogenic tumors, can similarly be used in compositions and methods of the invention.

As disclosed herein, these and other tumor cell lines can be genetically modified to express exogenous molecules that enhance an immune response to tumor antigens. Such molecules include, but are not limited to, CD80 (B7.1), human HLA antigens, for example, HLA A1, A2, A3, A27, and the like. One skilled in the art can readily obtain appropriate sequences encoding such molecules using well known methods. One skilled in the art will readily understand that variants of such molecules are available or can be readily obtained using well known methods. Based on known complete or partial sequences, one skilled in the art can use well known molecular biology methods to obtain nucleic acid sequences suitable to genetically modify a tumor cell, as disclosed herein. It is understood that these exemplary sequences as well as natural variations of such sequences are considered within the scope of the invention.

Exemplary nucleic acid sequences encoding molecules that enhance an immune response are available, for example, from GenBank, including complete and partial cDNA sequences as well as genomic sequences, and such sequences can be used to obtain nucleic suitable nucleic acid sequences encoding desired immune enhancing molecules. A representative selection of such sequences available from GenBank include, but are not limited to, GenBank accession numbers NT_005612; NM_012092; NM_175862; NM_006889; NM_005191; BC_042665; NM_012092; NM_175862; NM_006889; NM_152854; NM_005214; NM_005514; NM_002116; Z70315; NM_002127; AH013634; L34703; L34734; AF389378; U30904; AH006709; AH006661; AH006660; X55710; U04244; U35431; M24043; U03859; NM_005514; NM_002116; Z30341; NM_012292; NM_002127; NM_002117; AH007560; AH000042; AB048347; AB032594; AJ293264; AJ293263; AB030575 AB030574; AB030573; AF221125; AF221124; AH009136; X60764; AB032597; L17005; Y13267; AH003586; Z46633; Z27120; Z33453; Z23071; X02457; X57954; K02883; U21053; U04243; U18930; L36318; L36591; L38504; L33922; M20179; M20139; M24042; M15497; M31944; U04787; U01848; M27537; U11267; U03907; U03863; U03862; U03861; NM002116; L34724; L34723; L34721; L34737; L34701; Z97370; L15370; AH003070; M20179; M16273; M16272; M15497; M19756; M19757; NT008413, and the like.

The compositions and methods of the invention are useful for stimulating an immune response against a tumor. Such immune response is useful in treating or alleviating a sign or symptom associated with the tumor. Such an immune response can ameliorate a sign or symptom associated with a lung cancer. As used herein, by "treating" is meant reducing, preventing, and/or reversing the symptoms in the individual to which a compound of the invention has been administered, as compared to the symptoms of an individual not being treated according to the invention. A practitioner will appreciate that the compositions and methods described herein are to be used in concomitance with continuous clinical evaluations by a skilled practitioner (physician or veterinarian) to determine subsequent therapy. Hence, following treatment the practitioners will evaluate any improvement in the treatment of the pulmonary inflammation according to standard methodologies. Such evaluation will aid and inform in evaluating whether to increase, reduce or continue a particular treatment dose, mode of administration, etc.

The methods of the invention can thus be used to treat a tumor, including, for example, a cancer such as a lung cancer. The methods of the invention can be used, for example, to inhibit the growth of a tumor by preventing further tumor growth, by slowing tumor growth, or by causing tumor regression. Thus, the methods of the invention can be used, for example, to treat a cancer such as a lung cancer. It will be understood that the subject to which a compound of the invention is administered need not suffer from a specific traumatic state. Indeed, the compounds of the invention may be administered prophylactically, prior to any development of symptoms (e. g., a patient in remission from cancer). The term "therapeutic," "therapeutically," and permutations of these terms are used to encompass therapeutic, palliative as well as prophylactic uses. Hence, as used herein, by "treating or alleviating the symptoms" is meant reducing, preventing, and/or reversing the symptoms of the individual to which a therapeutically effective amount of a composition of the invention has been administered, as compared to the symptoms of an individual receiving no such administration.

The term "therapeutically effective amount" is used to denote treatments at dosages effective to achieve the therapeutic result sought. Furthermore, one of skill will appreciate that the therapeutically effective amount of the composition of the invention may be lowered or increased by fine tuning and/or by administering more than one composition of the invention (e. g., by the concomitant administration of two different genetically modified tumor cells), or by administering a composition of the invention with another compound to enhance the therapeutic effect (e. g., synergistically). The invention therefore provides a method to tailor the administration/treatment to the particular exigencies specific to a given mammal. As illustrated in the following examples, therapeutically effective amounts may be easily determined for example empirically by starting at relatively low amounts and by step-wise increments with concurrent evaluation of beneficial effect. The methods of the invention can thus be used, alone or in combination with other well known tumor therapies, to treat a patient having a tumor. One skilled in the art will readily understand advantageous uses of the invention, for example, in prolonging the life expectancy of a lung cancer patient and/or improving the quality of life of a lung cancer patient.

Current recommendations for NSCLC patients with locally-advanced inoperable disease (stage IIIB) include platinum-based chemotherapy plus radiation therapy, and chemotherapy alone for patients with metastases (stage IV) (Clinical practice guidelines for the treatment of unresectable non-small-cell lung cancer; adopted on May 16, 1997 by the American Society of Clinical Oncology, J. Clin. Oncol. 15: 2996-3018, 1997). Results of these approaches are nevertheless poor, and the increase in survival is limited. The largest meta-analysis published to date concluded that chemotherapy increases the chance of 1-year survival by 10% and median survival by 6 weeks (Chemotherapy in non-small cell lung cancer: A meta-analysis using updated data on individual patients from 52 randomizsed clinical trials. Non-Small Cell Lung Cancer Collaborative Group. BMJ 311: 899, 1995). A recent report from the Big Lung Trial group (BLT) reported similar results (Stephens et al., Proc. Am. Soc. Clin. Oncol. 21: 2002 (abstract 1661)). In phase III clinical trials, patients with metastatic disease have a median survival of less than 1 year (Schiller, et al., N. Engl. J. Med. 346: 92-98 (2002)).

Two phase III trials showed that after failure of first-line chemotherapy, only 6% of patients receiving standard second-line chemotherapy could expect to respond, with median survival being approximately 6 months (Shepherd, et al., J. Clin. Oncol. 18: 2095-2103 (2000); Fossella, et al., J. Clin. Oncol. 18: 2354-2362 (2000)). In the experiments described herein, the group of patients had a very poor prognosis as a result of their relapsed or metastatic disease status, and most patients had been unsuccessfully treated with surgery, radiation, and/or palliative chemotherapy, resulting in a projected survival of less than 6 months.

A vaccination approach such as that disclosed herein can be an effective means of inducing immune response in patients with nonimmunogenic tumors. There is evidence that NSCLC tumors contain tumor antigens (Yamazaki, et al., Cancer Res. 59: 4642-4650 (1999); Weynants, et al., Am. J. Respir. Crit. Care Med. 159: 55-62 (1999); Bixby, et al., Int. J. Cancer 78: 685-694 (1998); Yamada, et al., Cancer Res. 63: 2829-2835 (2003)). However, it has been thought that lung tumors are poor candidates for immunotherapy because they are poorly immunogenic and are potentially immunosuppressive (Woo, et al., J. Immunol. 168: 4272-4276 (2002); Woo et al., Cancer Res. 61: 4766-4772 (2001); Neuner, et al., Int. J. Cancer. 101: 287-292 (2002); Neuner, et al., Lung Cancer 34 (supplement 2): S79-82 (2001);

Dohadwala, et al., J. Biel Chem. 276: 20809-20812 (2001)), thereby energizing or tolerizing T-cells (Schwartz, J. Exp. Med. 184: 1-8 (1996); Lombardi, et al., Science 264: 1587-1589 (1994)). Lung tumors, therefore, have not been subjected to immune attack, and hence have not been able to evolve evasive mechanisms to resist immune effector cells. Lung tumors, unlike immunogenic tumors that harbor tumor-infiltrating lymphocytes, thus may succumb to killer CTLs, especially in light of the involvement of CD8 CTLs in tumor rejection in a number of model systems (Podack, J. Leukoc. Biel. 57: 548-552(1995)).

As disclosed herein, an allogeneic whole cell vaccine was chosen because whole cell. vaccines have given the best clinical results so far. For example, statistically significant survival benefit occurred when a whole cell melanoma vaccine was administered (Morton, et al., Ann. Surg. 236: 438-449 (2002)). In contrast, vaccine directed at a single epitope may have limited utility due to tumor escape mutants (Velders, et al., Semin. Oncol. 25: 697-706 (1998)). The additional advantage of a whole cell vaccine approach is that it does not require a priori delineation of specific lung tumor antigens. If vaccination is successful and CTLs are generated, as was found in the experiments disclosed herein, the responsible antigenic sites can be identified later. Allogeneic cell-based vaccines offer a good alternative to autologous vaccines under the assumption that lung tumor antigens are shared in lung tumors of different patients, and the antigens can be cross-presented by the patients' antigen-presenting cells. Although there is only limited evidence for shared antigens in lung tumors (Yamazaki, et al., Cancer Res. 59: 4642-4650 (1999); Yamada, et al., Cancer Res. 63: 2829-2835 (2003)), this has been shown in other tumors (Fong, et al., Annu. Rev. Immunol. 18: 245-273 (2000); Boon, et al., Annu. Rev. Immunol. 12:337-365 (1994)).

Figure 5A:
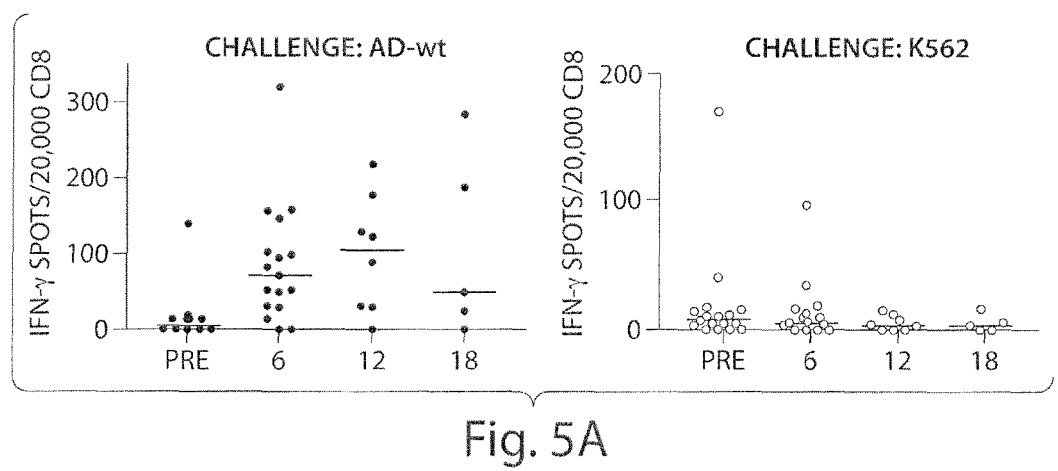
FIGS. 5A and B show analysis of CD8 immune response.
Figure 5B:
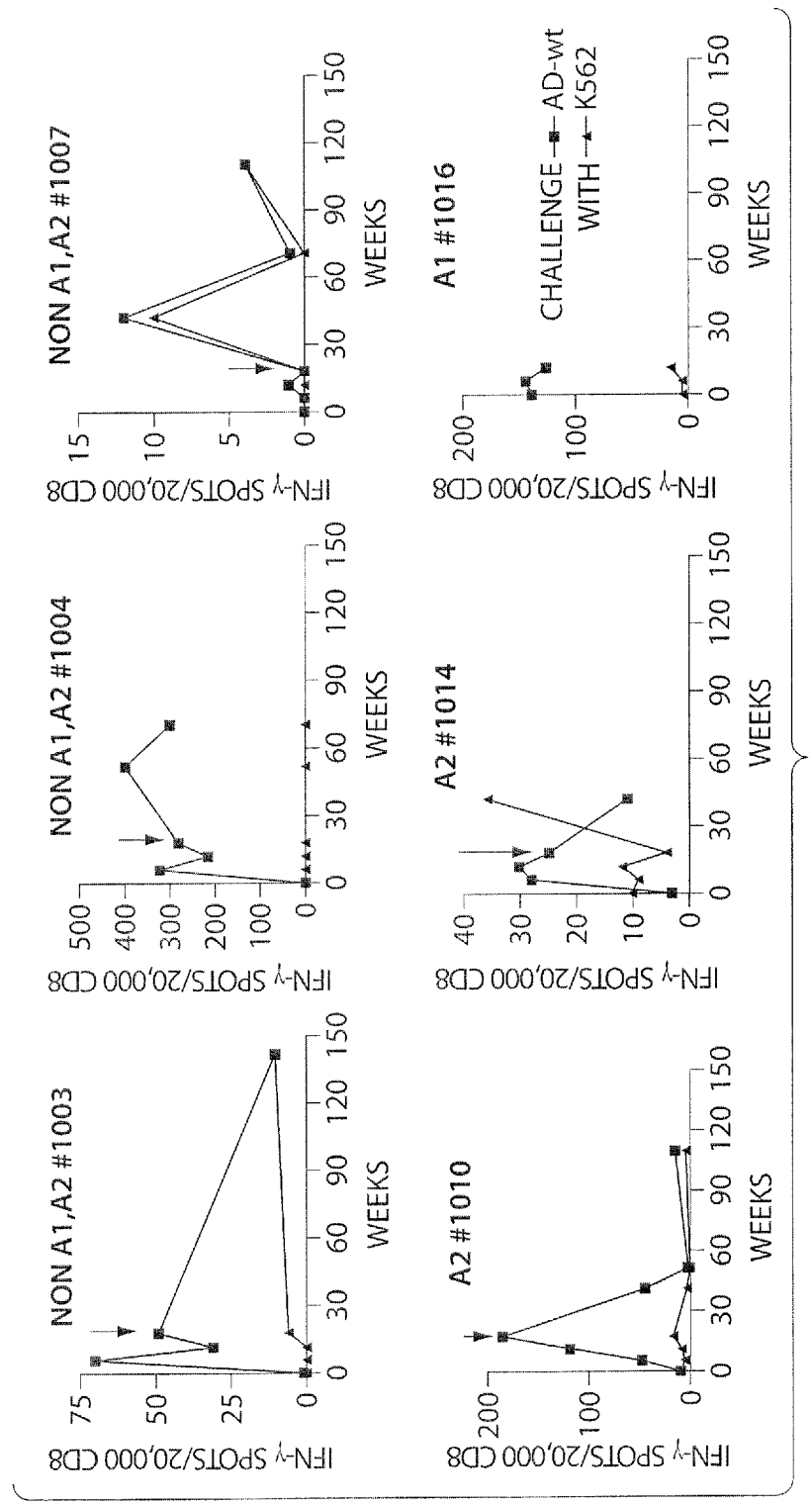
FIG. 5B (lower six panels) shows CD8 response after termination of vaccination (arrow) in patients with clinical response.

To obtain direct evidence that the CD8 cells generated in response to allogeneic vaccination recognize autologous tumor cells, tumor specimens should be obtained at the time of surgery. Tumor specimens were not available in the trial of patients disclosed herein with advanced disease (see Examples I1 and 111). However, the prolonged maintenance of a high frequency of patient CD8 cells reacting to AD100 in vitro, and their increase in some patients (No. 1004 and No. 1007; FIG. 5) even after cessation of external vaccination, is consistent with the immune stimulation of patient CD8 cells by the autologous tumor and their cross-reaction with the allogeneic vaccine.

In the experiments disclosed herein, although only one patient had a partial response, five other patients had stable disease. Enhanced immune reactivity was demonstrated by a CD8-mediated tumor-specific immune response. The fact that six (32%) of 19 patients with very poor prognosis exhibited disease stabilization of a rapidly lethal condition, with median survival of the whole cohort reaching 18 months despite far-advanced disease, is encouraging. The results disclosed herein indicate that tumor progression is slowed by vaccination, and that this effect occurs regardless of whether or not patients are allogeneic to the HLA A1 or A2 locus of the vaccine. The findings also indicate that indirect antigen presentation can be effective in promoting antitumor activity and that allogeneic MHC molecules enhance the effect.

In the results disclosed herein, the vaccine was well tolerated and the patients' quality of life was very good, thus improving patient outcome. Because this is an immunologic product, it was assumed that some immune-mediated side effects would be anticipated. Probable examples of such phenomena of expected tolerable side effects were, for example, the local erythema at the vaccination site in five patients, and the episode of arthritic pain experienced by one patient (see Example 3).

A composition of the invention containing a tumor cell genetically modified to express CD80 and an HLA antigen can be combined with a physiologically acceptable carrier useful in a vaccine by including any of the well known components useful for immunization. The components of the physiological carrier are intended to facilitate or enhance an immune response to an antigen administered in a vaccine. The formulations can contain buffers to maintain a preferred pH range, salts or other components that present the antigen to an individual in a composition that stimulates an immune response to the antigen. The physiologically acceptable carrier can also contain one or more adjuvants that enhance the immune response to the antigen. Formulations can be administered subcutaneously, intramuscularly, intradermally, or in any manner acceptable for immunization.

An adjuvant refers to a substance which, when added to an immunogenic agent of the invention such as tumor cell genetically modified to express CD80 and an HLA antigen, nonspecifically enhances or potentiates an immune response to the agent in the recipient host upon exposure to the mixture. Adjuvants can include, for example, oil-in-water emulsions, water-in oil emulsions, alum (aluminum salts), liposomes and microparticles, such as, polysytrene, starch, polyphosphazene and polylactide/polyglycosides.

Adjuvants can also include, for example, squalene mixtures (SAF-I), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. Nature 344: 873-875 (1990). For veterinary use and for production of antibodies in animals, mitogenic components of Freund's adjuvant (both complete and incomplete) can be used. In humans, Incomplete Freund's Adjuvant (IFA) is a useful adjuvant. Various appropriate adjuvants are well known in the art (see, for example, Warren and Chedid, CRC Critical Reviews in Immunology 8: 83(1988); Allison and Byars, in Vaccines: New Approaches to Immunological Problems, Ellis, ed., Butterworth-Heinemann, Boston (1992)). Additional adjuvants include, for example, bacille Calmett-Guerin (BCG), DETOX (containing cell wall skeleton of Mycobacterium phlei (CWS) and monophosphoryl lipid A from *Salmonella minnesota* (MPL)), and the like (see, for example, Hoover et al., J. Clin. Oncol., 11: 390 (1993); Woodlock et al., J. Immunotherapy 22: 251-259 (1999)).

Figure 6:
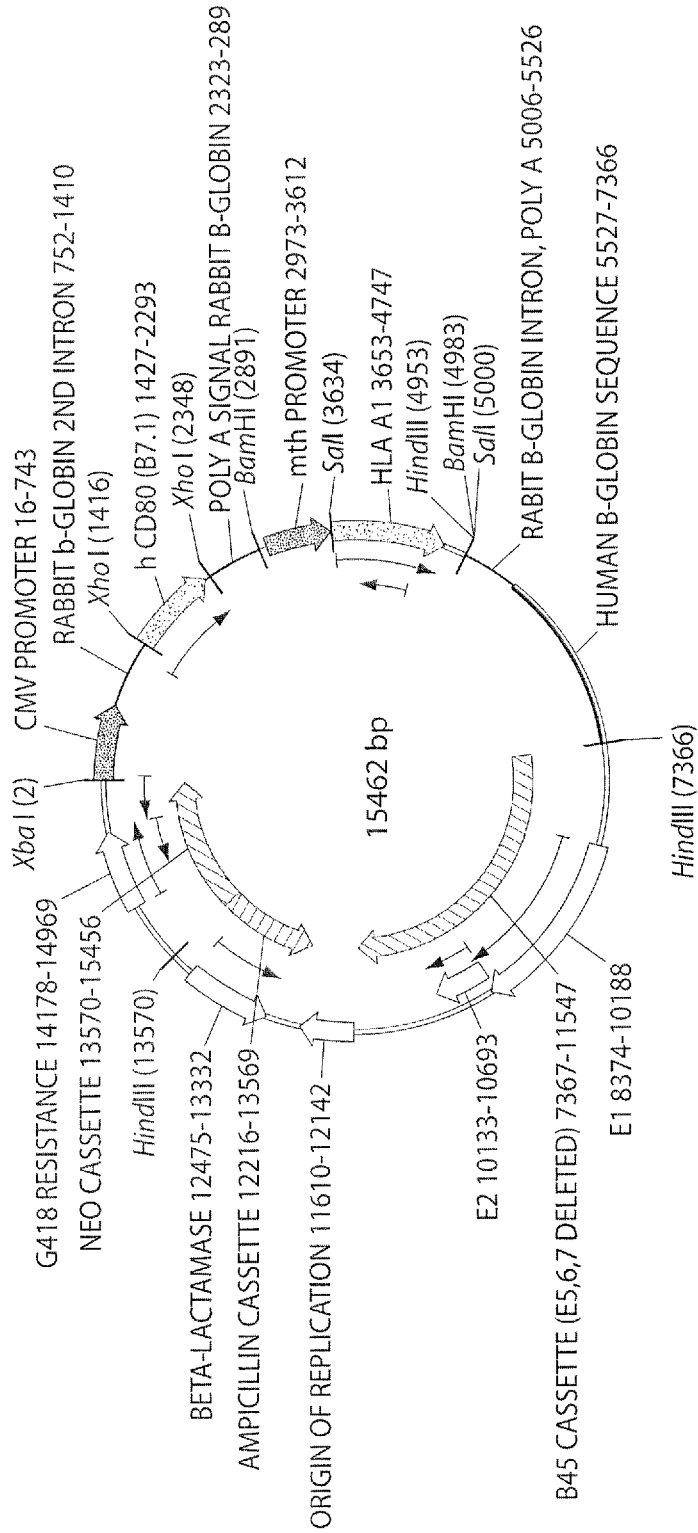
FIG. 6 illustrates the sequence and annotation of one embodiment of a BPV-1-B7.1-HLA A1 vector.

FIG. 6 illustrates the sequence and annotation of one embodiment of a BPV-1-B7.1-HLA A1 vector derived from a bovine papillomavirus type 1 (BPV-1) vector. The vector was further engineered to contain two expression cassettes for expression genes under the CMV and the Metallothioneine promoter, respectively. The sequence of this vector is shown at the end of the specification.

The compositions and methods of the invention disclosed herein are useful for treating a patient having a tumor. Although particular embodiments are exemplified with lung cancers, it is understood that a similar approach can also be used to treat other types of tumors, including cancers, using suitable allogeneic cells.

It is understood that modifications which do not substantially affect the activity of the various embodiments of this invention are also provided within the definition of the invention provided herein. Accordingly, the following examples are intended to illustrate but not limit the present invention. While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

Example 1: Allogeneic Vaccination with a B7.1/HLA-A Gene-Modified Adenocarcinoma Cell Line in Patients with Advanced Non-Small-Cell Lung Cancer This example describes the protocol used for allogeneic vaccination with a B7.1 HLA-A gene-modified adenocarcinoma cell line in patients with advanced non-small-cell lung cancer (NSCLC). This example describes the experimental protocol used.

The following experiments were designed (a) to measure whether CD80 and HLA A transfected, allogeneic lung tumor cells used for immunotherapy can elicit tumor specific CD8-CTL activation and expansion, assessed by ELIspot for IFN-γ; (b) to evaluate the safety and toxicity of administering allogeneic tumor cell vaccines transfected with B7.1 and HLA A1 or A2 in patients with Non-Small Cell Lung Carcinoma (NSCLC); and (c) to evaluate the antitumor effect of this B7.1 vaccine in clinical outcomes for patients with NSCLC.

Selection of Patients. Initially, fifteen patients with newly diagnosed or relapsed metastatic non-small cell lung cancer (NSCLC) were treated. The analysis of these 15 patients is described in Example 2. An additional four patients were added, for a total of 19 patients, and the further results with the 19 patients are described in Example 3. The patients had already failed chemotherapy, radiotherapy, surgery or a combination of all. Eligibility criteria were as follows: age >18 years, Eastern Cooperative Oncology Group (ECOG) performance status 0-2, measurable disease, signed informed consent, and histologically confirmed NSCLC (stage IIIB with malignant pleural effusion, stage IV, or recurrent). Patients with brain metastasis were included if these were already treated. Patients were not eligible for study if they were receiving chemotherapy, radiation therapy or a biologic modifying agent or during the preceding 4 weeks. All patients were treated in the outpatient clinic at Sylvester Comprehensive Cancer Center/University of Miami. A complete history and physical exam was performed, including weight and vital signs, with performance status assessed by ECOG criteria. The following tests were performed prior to enrollment: complete blood count; platelet count; chemistries (uric acid, calcium, phosphorus, transaminases including serum glutamic-oxaloacetic transaminase (SGOT) and serum glutamic-pyruvic transaminase (SGPT), alkaline phosphatase, lactate dehydrogenase (LDH), total and direct bilirubin, blood urea nitrogen (BUN), creatinine, albumin, total protein, electrolytes, and glucose); and electrocardiogram (EKG). HLA typing was obtained. Patients were followed twice monthly while being vaccinated, with tumor response assessed by computed tomography (CT) scans. Tumor measurements were obtained from the results of radiographic studies, including CT scans of relevant sites.

Vaccine Cell Line and Genetic Modification. A human lung adenocarcinoma cell line was established in 1994 by Dr. N. Savaraj (University of Miami, Department of Medicine) from a biopsy of a lung cancer patient, designated as AD100. The patient was a 74 year old white male who presented in 1993 with initial symptoms of pelvic pain from bone erosion of the iliac crest due to metastatic pulmonary adenocarcinoma. Cancer cells for culture were obtained by bone marrow aspiration from the area of pelvic bone destruction. The patient was treated with radiation therapy to the pelvis, but expired one month after diagnosis. The cell line derived from this patient has been kept in culture in standard medium (described below) and is free of contamination by mycoplasma, virus or other adventitious agents. The cell line is homogeneous, adherent to plastic, and grows with a rate of division of approximately 26 h.

Genetic Modification. AD 100 was transfected with plasmid cDNA, pBMG-Neo-B7.1 and pBMG-His-HLA A2 or with B45-Neo-CM-A1-B7.1 (Yamazaki et al., CancerRes., 59: 4642, 1999) Transfected cells were selected with G418 and histidinol. Verification of correct sequences was based on restriction analysis and the expression of the relevant gene products, namely G418 or histidinol resistance for the vector sequence, HLA A1, A2, and B7.1 expression for the transfected cDNA. The cells were irradiated to prevent their replication, for example, with 12,000 Rads in a cobalt (Co) irradiator, and stored frozen in 10% DMSO in aliquots of $5 \times 10^7$ cells until use. Upon replating in tissue culture the cells appeared viable for about 14 days but were unable to form colonies, indicating their inability to replicate. They were therefore considered safe for use as vaccine cells. The minimum requirement for their use as vaccine was the co expression of HLA A1 or A2 plus B7.1 on at least 70% of the cells, as shown in FIG. 1A for representative batches of vaccine cells. The untransfected AD100 line was negative by FACS for staining with anti HLA A1 or A2 or B7.1. FIG. 1A shows the quality control by flow cytometric analysis of CD80 and HLA A1 or A2 transfected AD 100 vaccine cells used for immunization.

Immunizations. Intracutaneous injections were given at multiple body sites to reduce the extent of local skin reactions. Patients who were HLA A1 or A2 received the corresponding HLA-matched vaccine, whereas patients who were neither HLA A1 nor HLA A2 received HLA A1-transfected vaccine (that is, HLA-unmatched vaccine). On a given vaccination day, the patient received the total dose of $5 \times 10^7$ irradiated cells (12,000 rad) divided into two to five aliquots for administration as two to five intradermal injections of each aliquot in an extremity, spaced at least 5 cm at needle entry from the nearest neighboring injection. A total of nine immunizations ($4.5 \times 10^8$ cells) were given over the course of therapy, one every two weeks, provided that no tumor progression occurred under therapy (Table 1). On subsequent vaccinations, the injection sites were rotated to different limbs in a clockwise manner. One course of vaccination comprised three biweekly injections. Patients with evidence of stable disease or responding NSCLC by imaging evaluation (CT Scans) and none to moderate toxicity (grade <2) were treated with an additional course at the same dose. The second course of injections started two weeks after the third vaccination that completed the first course. In the absence of tumor progression by CT scans and with no severe or life-threatening toxicity (grade >3), a third course at the same dose of therapy was given, starting two weeks after the third vaccination of the second course of therapy. Clinical" toxicity, and immunologic evaluations by blood tests prior to and after each course were performed was done. Patients were followed clinically weekly during the study, including monitoring blood counts and basic chemistries (Table 1).

Table 1 shows the treatment and evaluation schedule of NSCLC (IIIB/IV) patients. Patients were immunized nine times in biweekly intervals, as discussed above. Immunological assays were done prior to and after each of three immunizations.

TABLE 1

Immunizations and Immunological Evaluations

| | Study Entry | Course 1 | | | | Course 2 | | | Course 3 | | | |
|---|---|---|---|---|---|---|---|---|---|---|---|---|
| Week's on Study | 1 | 2 | 4 | 6 | 7 | 8 | 10 | 12 | 13 | 14 | 16 | 18 | 19 |
| Pre-Entry Evaluation | x | | | | | | | | | | | | |
| Immunization # | | 1 | 2 | 3 | | | 4 | 5 | 6 | | 7 | 8 | 9 |
| Clinical Evaluation | x | x | x | x | x | x | x | x | x | x | x | x | x |
| Toxicity Evaluation | | x | x | x | x | x | x | x | x | x | x | x | x |
| Immunological Evaluation # | 1 | | 2 | | | | | 3 | | | | | 4 |

Figure 1B:
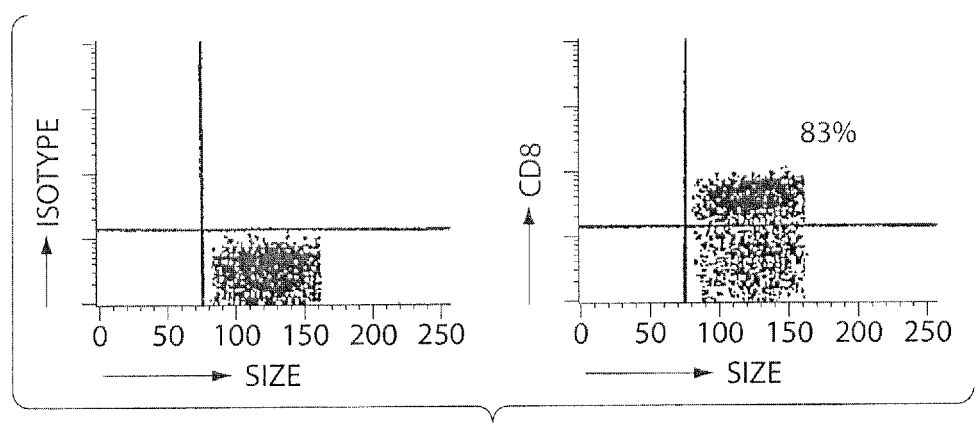

Immunological Testing. Immunological tests were performed included skin tests delayed-type hypersenstivity (DTH) and enzyme-linked immunospot (ELISPOT) assays for interferon-γ IFN-γ. Immune responses mediated by CD4 cells were examined by DTH-reaction following intradermal injection of 105A1, A2 or untransfected AD 100-B7 vaccine cells. Purified CD8 cells were obtained from patients prior to and after each course of three immunizations. CD4 cells were enriched by negative depletion with anti-CD56, anti-CD4 and other antibodies using the Spin-sep prep (Stem Cell Technologies; Vancouver, Canada). Purity was better than 80% (FIG. 1B) the primary contaminating cells being B cells (not shown). CD8 cells were frozen in 10% dimethylsulfoxide (DMSO) and 20% fetal calf serum (FCS) containing medium for analysis until all vaccinations of a study patient were completed. Analysis for pre-immune and post-vaccination ELISPOT frequency was carried out on the same day in the same micro titer plate. Assays were done in quadruplicate, stimulating 2×10$^4$ purified patient CD8 cells with, respectively, 10$^3$ A1 or A2 transfected or untransfected AD100, with K562 or with media only for three days and determining the frequency of IFN-γ producing cells by ELISPOT. Immune assays were performed prior to immunization and after 3, 6, and 9 immunizations.

Statistical Analysis. Patient characteristics are presented as counts with percentages, or as mean values and range. Overall survival, estimated by the Kaplan-Meier product-limit method, is defined as time from enrollment onto study until death from any cause. In the absence of death, follow-up was censored at the date of last patient contact. Univariate and multivariate proportional hazards regression were used to determine whether patients' survival time was related to age (continuous), sex, race (other versus white non-Hispanic), tumor pathology (adenocarcinoma versus other), and HLA-matching of vaccine. Logistic regression was used for the corresponding analyses of clinical response. For hazard ratios and the percentage of patients surviving, 90% confidence intervals (CIs) $L_{90}$-$U_{90}$ are reported. These can be interpreted as providing 95% confidence that the parameter being estimated, such as the hazard ratio, exceeds $L_{90}$.

Example 2: Specific CD8 T Cell Response of Advanced Lung Cancer Patients to Whole Cell Immunization with an Allogeneic Vaccine This example describes the results of a 15 patient group study on whole cell immunization with an allogeneic vaccine.

Patients with advanced NSCLC stage IIIB/IV were HLA typed. HLA A1 positive patients received the AD-A1-B7 vaccine; HLA A2 positive patients received the AD-A2-B7 vaccine; and patients that were neither HLA A1 nor A2 positive received either the AD-A1-B7 or AD-A2-B7 vaccine. The frequency of IFN-γ secreting CD8 cells was determined by ELISPOT after restimulation of purified patient-CD8 cells in vitro with HLA A1 or A2 transfected or untransfected AD100. Controls included stimulation with K562 and incubation of CD8 cells without stimulator cells.

Figure 2A:
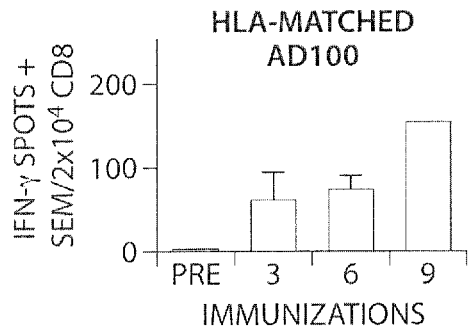
FIG. 2A-2G shows analysis of CD8 immune response: Immunization of advanced lung tumor patients generates strong CD8 response. The frequency of IFN-$\gamma$-spot forming CD8 cells obtained from lung tumor patients is plotted against the time on study in weeks. Immunizations were given every two weeks, zero representing the preimmunization status. 20,000 purified CD8 cells were used for ELI-spot assays. Panel A: Frequency of spot forming CD8 cells from HLA A1 and A2 positive patients challenged with HLA A1 or A2 transfected (matched) AD 100 tumor cells at a ratio of 20:1=CD8:AD100. Panel B: Frequency of spot forming CD8 cells from HLA A1 positive patients challenged With A2-AD 100 or HLA A2-CD8 cells were challenged with A1-AD 100 (mismatched). Panel C: Frequency of spot forming CD8 cells from non HLA A-1 or A2 patients cells challenged with A1 and A2 transfected AD100 (unmatched). Panel D: Frequency of spot forming CD8 cells from all patients challenged with untransfected wild type (w. t.) AD100 or, Panel E, with K562. Panel F: Mean frequency of spot forming CD8 cells from all patients challenged with any of the AD100 w. t. or transfected cells. Panel G: CD8 spot forming response of individual, clinically responding patients. The mean number of spots after restimulation with AD 100 w. t., AD100-A1, AD100-A2, K562 or nothing in quadruplicate wells is plotted against time after study entry. Arrows indicate the time of last immunization. Patient 1004, 1007, 1010 contain follow up data analyzed at the points indicated after completion of nine immunizations (18 weeks). HLA type of each patient is indicated in brackets.
Figure 2B:
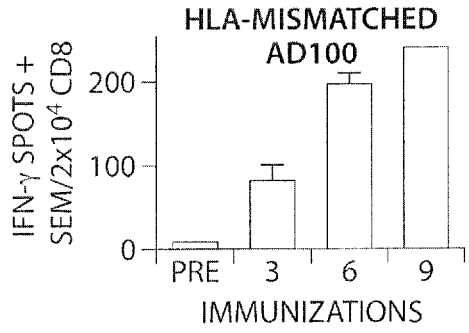

ELISPOT responses of immunized tumor patients are presented as HLA matched responses (FIG. 2A), representing the number of IFN-γ secreting CD8 cells obtained from HLA A1 or A2 patients challenged in vitro for three days with HLA A1 or A2 transfected AD100 cells, respectively. HLA mismatched responses indicate the number of spots formed when CD8 cells from A1 or A2 patients were challenged with A2 or A1 transfected AD 100, respectively (FIG. 2B). The matched response increased 15-fold, from 6±4 (standard error of the mean, SEM) IFN-γ secreting, pre-immune CD8 cells (per 20 thousand) to maximal 90±35 (SEM) IFN-γ secreting cells after six immunizations and remained at this level during the next three immunizations. The mismatched response increased 5.7 fold, from 24±18 to 142±42 maximal. Included in this group of nine patients is the one patient who showed no response (0 spots) before or after three immunizations, at which time the tumor progressed and the patient was taken off trial.

Figure 2C:
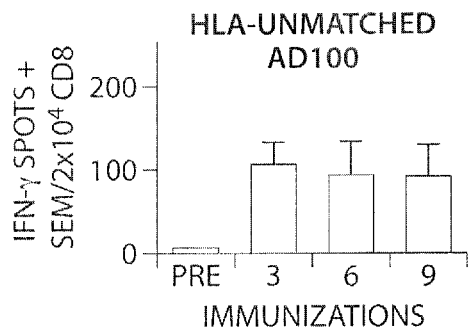
Figure 2D:
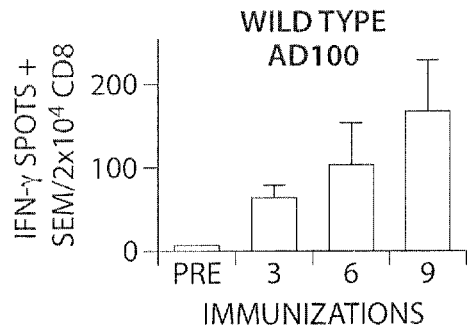

The remaining 5 patients were negative for HLA A1 or A2. These patients CD8 response to challenge with A1 or A2 transfected AD 100 is shown as unmatched response in FIG. 2C. The frequency of IFN-γ secreting CDS cells increased 21-fold from 4.8±1.8 pre-immune to 105±24 after three immunizations and stayed constant throughout the trial. This increase in frequency is similar to that of all patients' CD8 cells when challenged with the untransfected wild type AD100 (FIG. 2D). Finally, the specificity of the response is evident from the absence of an increase of the response to K562 (FIG. 2E) or of unchallenged CD8 cells. The CD8 response to K562 and to AD100 in its w. t. form or after genetic modification is significantly different at each time point after vaccination (FIG. 2F).

The CD8 response listed in Table 2 reports the response to the matched vaccine for A1 or A2 positive patients. For non A1, A2 patients, it is the response to AD100-A2. One of 15 patients could not be analyzed due to renal failure unrelated to the trial prior to completing the first course of immunization. Of the fifteen patients treated, five patients had clinical responses: one partial response (PR), and four patients with stable disease (SD). Four of these patients with clinical responses, (PR+3 SD), are still alive with stabilization of their diseases without further therapy for: 31, 28, 25, and 12 months.

The patient that died, originally had SD for 5 months then progressed and died 15 months later in spite of several courses of palliative chemotherapy. In contrast, nine of the other ten patients that did not respond to the vaccination are deceased except one patient who achieved stable disease after therapy with Iressa™. Table 2 summarizes the data for all patients, including pre-trial treatment, clinical response to immunization and immune response. Patients that had progressive disease while under treatment went off study as indicated in Table 2.

Table 2 shows a summary of clinical responses, immunological CD8 responses, survival and pretreatment of fifteen patients with advanced stage IIIB/IV NSCLC treated with allogeneic B7/HLA A transfected NSCLC vaccine. The abbreviations in Table 2 are: PD—progressive disease; NE—not evaluable for immune response, but included in survival analysis on the right; PR—partial response; SD—sable disease; C—chemotherapy; R—radiation; S—surgery. Survival indicates time of survival since study entry; + indicates patient alive; n. d. no done, patients off study because of progression.

swelling that resolved in three to four days. One patient complained about transient arthralgias that may have been treatment related. One patient died within 30 days of the last immunization due to pulmonary failure; one patient who had previous episodes of pericarditis experienced pericardial effusion during the last course of immunization, requiring a pericardial window. No tumor cells were detected in the fluid; the patient responded to immunization and is still in stable disease. As mentioned above, one patient had renal failure prior to completion of one course of immunization. None of these events were deemed likely to be treatment related by an independent safety monitoring board.

TABLE 2

Summary of Clinical Responses, Immunological CD8 Responses, Survival and Pretreatment of Fifteen NSCLC Patients.

| Patient # HLA | Response | Fold Titer increase | Previous TX | Survival (mos) | Time to Progression (mos) | Ifn-γ producing CD8 cells to AD100-HLA challenge (spots per 20,000) | | |
|---|---|---|---|---|---|---|---|---|---|
| | | | | | | Pre-immune | 1st course | 2nd course | 3rd course |
| 1005 A1 | PD | 190 | C + R | 10 | — | 0 | 190 | n.d. | n.d. |
| 1012 A1 | NE | NE | C | 15 | — | 0.2 | n.d. | n.d. | n.d. |
| 1001 A2 | PD | 25 | C + S | 18 | — | 0 | 25 | n.d. | n.d. |
| 1002 A2 | PD | 1.6 | C + S | 22 | — | 41 | 65 | n.d. | n.d. |
| 1009 A2 | PD | 6.5 | C | 3 | — | 2 | 13 | n.d. | n.d. |
| 1010 A2 | PR | 41 | S | 27+ | 3 | 3.8 | 46 | 88 | 157 |
| 1011 A2 | PD | 19 | C | 11 | — | 3 | 30 | 57 | n.d. |
| 1013 A2 | PD | 34 | C + R + S | 2 | — | 5.2 | 164 | 178 | n.d. |
| 1014 A2 | SD | 19 | C + S | 13+ | 3 | 1.6 | 30 | 30 | 25 |
| 1015 A2 | PD | 0 | C + R | 7 | — | 0 | 0 | nd | nd |
| 1003 non | SD | 134 | S | 31+ | 26+ | 1 | 134 | 113 | 84 |
| 1004 non | SD | 424 | C + R | 23 | 11 | 0 | 424 | 232 | >450 |
| 1006 non | PD | 9.3 | C + S | 30+ | — | 16 | 150 | n.d. | n.d. |
| 1007 non | SD | 14 | C + R + S | 29+ | 23+ | 1.2 | 2.8 | .8 | 0/17 |
| 1008 non | PD | 32 | C | 6 | — | 5.6 | 178 | n.d. | n.d. |

Figure 2E:
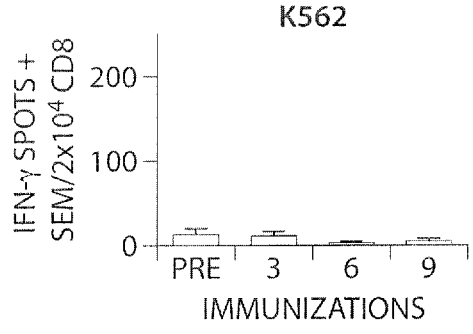
Figure 2F:
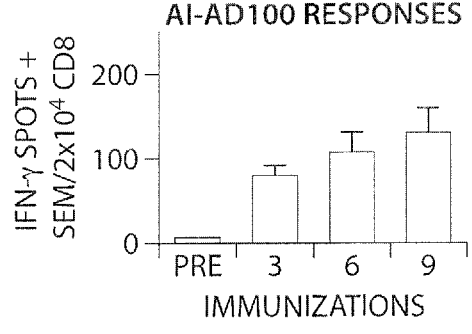
Figure 2G:
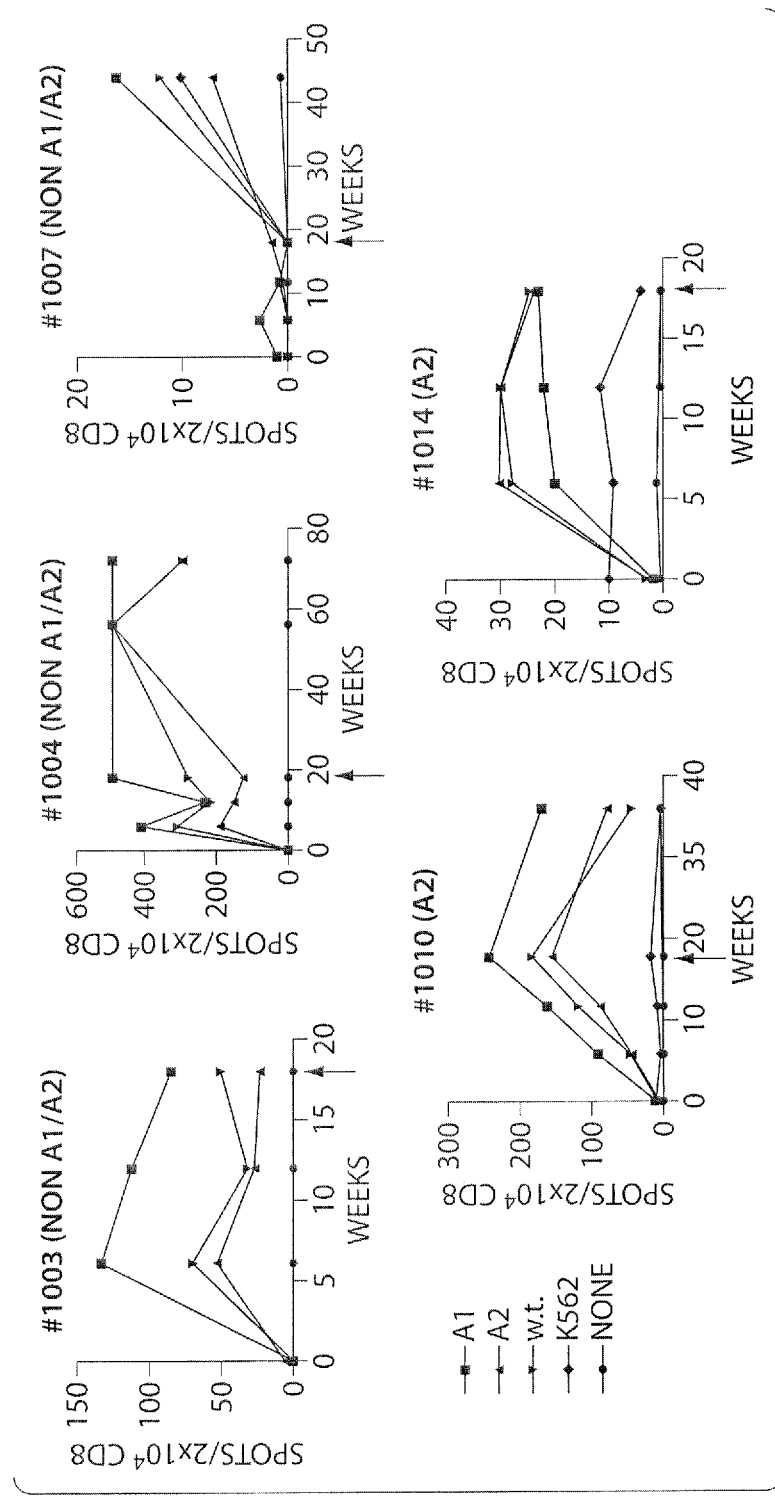

Five patients had a clinical response and the frequency of IFN-spot forming CD8 cells increased upon successive immunization as measured by challenge ex vivo with transfected or untransfected AD100, while the reactivity to K562 remained low and unchanged (FIG. 2E). In three of the clinically responding patients (FIG. 2; 1004, 1007, 1010), blood samples were obtained after completion of the 18 week treatment period at 35 to 75 weeks post trial entry and showed still a considerable titer of CD8 cells responding to AD100 (FIG. 2G). Indeed, in two of two patients (1004, 1007), the titer increased further even after immunization was ended at 18 weeks.

Figure 3:
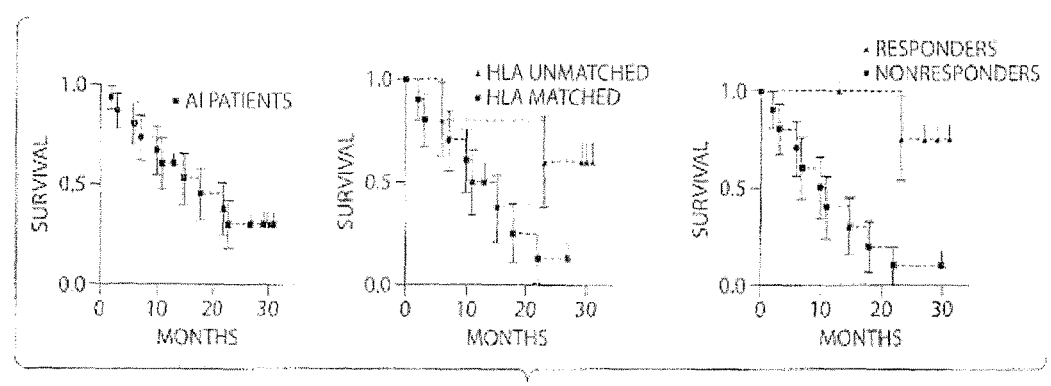
FIG. 3 shows the median survival time of all patients at the time of analysis. The median survival time was 18 months, exceeding the expected median survival time of less than one year for this group of patients.

The median survival time of all patients at the time of analysis was 18 months, exceeding the expected median survival time of less than one year for this group of patients (FIG. 3). 90% confidence intervals are shown in FIG. 3. Analysis of survival by MHC matching and by clinical response revealed that HLA unmatched patients showed a survival advantage that with p=0.07 was not statistically significant while clinical responders had a significant (p=0.008) survival advantage when compared to non responders.

Safety. None of the 15 patients entered into the trial experienced any treatment related serious adverse events, defined as deaths or events requiring hospitalization. Treatment related side effects consisted of local erythema and Example 3: Further Characterization of Advanced Lung Cancer Patients to Whole Cell Immunization with an Allogeneic Vaccine This example describes a continuation of the study described in Example 2, including additional patients and time of study. Experiments were performed essentially as described in Example 2 and Raez et al., J. Clin. Oncol. 22: 2800-2807 (2004).

Patient Characteristics. The characteristics of the 19 study patients are outlined in Table 3. Eastern Cooperative Oncology Group performance status was 0 to 1 in 18 patients (74%). Thirteen patients received vaccine matched for HLA, either A1 (three patients) or A2 (10 patients), whereas the six patients who were non-A1 and non-A2 received unmatched vaccine (that is, HLA-A1 vaccine). While HLA A matched patients may be able to mediate CD8 responses by direct antigen presentation by the vaccine cells, it was reasoned that unmatched patients may, nonetheless, mount a CD8 response via indirect antigen presentation after vaccine cell death and antigen uptake by antigen presenting cells. Before being enrolled on study, all patients had been previously treated: nine (47%) with surgery, six (32%) with radiation therapy, and 17 (89%) with chemotherapy. Among the chemotherapy-treated patients, 10 (53%) had been unsuccessfully treated with more than one chemotherapy regimen.

TABLE 3

Characteristics of the 19 patients enrolled in the study.

| Characteristic | No. of Patients |
|---|---|
| Age, years* | |
| <50 | 2 |
| 50-59 | 6 |
| 60-69 | 5 |
| 70+ | 6 |
| Sex | |
| Female | 12 |
| Male | 7 |
| Race/ethnicity | |
| White non-Hispanic | 13 |
| White Hispanic | 5 |
| Black non-Hispanic | 1 |
| Pathology | |
| Adenocarcinoma | 11 |
| Bronchoalveolar | 3 |
| Squamoous cell | 3 |
| Undifferentiated | 2 |
| Metastasis site | |
| Adrenal | 1 |
| Brain | 3 |
| Liver | 1 |
| Lung | 9 |
| Pleura | 1 |
| Multiple sites† | 4 |
| ECOG performance status | |
| 0 | 4 |
| 1 | 14 |
| 2 | 1 |
| HLA | |
| A1 | 3 |
| A2 | 10 |
| Neither | 6 |

Abbreviation:
ECOG, Eastern Cooperative Oncology Goup.
*Mean = 62 years; range 36 to 82 years.
†One pancreas/lung/adrenal; one brain/lung; one lung/adrenal; one liver/lung/T-spine.

Clinical Outcomes. Eighteen patients received a total of 30 courses of vaccine, 90 vaccinations in total (Table 4). Five patients received three full courses, and two patients had two full courses. With the exception of one patient taken off study because a serious adverse event (SAE) occurred after the first vaccination (zero courses completed), the remaining 11 patients had one full course, after which they were taken off study because of disease progression. Four patients experienced SAEs after vaccination, none of which was judged to be vaccine-related.

TABLE 4

Outcomes in the 19 Patients Enrolled on Study.

| Outcome | No. of Patients |
|---|---|
| Courses of vaccine received | |
| 0 | 1 |
| 1 | 11 |
| 2 | 2 |
| 3 | 5 |
| Clinical response | |
| Complete | 0 |
| Partial | 1 |
| Stable disease | 5 |
| Progressive disease | 13 |
| Serious AEs (grade 3 and 4) | |
| Pericardial effusion | 2 |
| Renal Failure | 1 |
| Respiratory failure | 1 |
| AEs (grade 1 or 2) | |
| Rash | 1 |
| Chest pain* | 1 |
| Joint pain | 1 |
| Status† | |
| Alive | 7 |
| Dead | 12 |

Abbreviation:
AE, adverse event.
*Chest pain/shortness of breath.
†Alive: median follow-up was 36 months (range, 10 to 40 months); time of death ranged from 1 to 23 months after entry on study.

During the first course of vaccination, a 58-year-old woman developed malignant pericardial effusion requiring a pericardial window; the patient was taken off study, discharged to hospice, and died 1 week later. She had previously been treated unsuccessfully with five lines of palliative chemotherapy before enrollment on study. A 76-year-old male patient also developed a pericardial effusion requiring a pericardial window, but review of prior scans revealed developing pericardial effusion before entry on study. This patient, who had received three courses of vaccine before the SAE developed, continues to have stable disease. He is currently alive and well after 31 months without any further therapy.

A 55-year-old male was found to have worsening of chemotherapy-induced renal dysfunction the day of his first vaccination after he had already signed consent 1 week earlier and underwent a preliminary skin test. His renal function continued deteriorating in the following days, and he died 3 months later. The fourth patient who experienced a SAE was a 56-year-old woman with brain metastasis. During her second course of vaccination, she developed respiratory failure, was then taken off study, and died within 30 days from progression of her disease. This patient had previously been unsuccessfully treated with four lines of palliative chemotherapy.

Regarding other side effects, one patient complained of transient pain at the injection site. Four patients developed some erythema at the vaccination site that resolved within a week. One patient experienced moderate arthritic pain in several joints after the first course. We did not find any patients with significant alteration of their laboratory parameters. including: complete blood and platelet counts, creatinine/BUN, calcium, and liver function tests. Table 5 shows time to response, duration of response, and survival time for the six patients who had response on study.

TABLE 5

Time to Response, Duration of Response, and Survival Time for the Six Patients Who Had Response on Study.

| Patient ID | Response | Time to Response (months) | Duration of Response (months) | Survival Time (months)* |
|---|---|---|---|---|
| 1010 | PR | 2.3 | 13 | 36+ |
| 1003 | SD | 1.9 | 39+ | 40+ |
| 1004 | SD | 1.6 | 3.5 | 23 |
| 1007 | SD | 2.1 | 2.5 | 37+ |
| 1014 | SD | 2.3 | 3.5 | 21+ |
| 1016 | SD | 1.9 | 1.6 | 11+ |

Abbreviations:
PR, partial response;
SD, stable disease
*Patients alive as of February, 2004 denoted by plus sign.

One patient had a partial response lasting 13 months, and five showed stable disease ranging from 1.6 to 39+ months (Table 5). The clinical response rate was 32% (six of 19 patients). As of February 2004, these patients had survival times ranging from 23 to 40+ months, and five patients were still alive.

After the patient who had a partial response developed new malignant lesions, verified by positron emission tomography scan, she was put under observation for 2 months because her disease was judged clinically nonaggressive. Several lesions subsequently decreased in size or disappeared. This patient continues to have stable disease without need of palliative chemotherapy 36 months after completing vaccination. Only one of the six patients who had a response on treatment required subsequent palliative chemotherapy. The remaining five patients continue to have stable disease without need of further treatment.

Among the other 13 patients who did not respond to therapy, only two were alive as of February 2004. One of these patients experienced disease stabilization with gefitinib (Iressa™), and the other is undergoing palliative chemotherapy.

Logistic regression analyses of age, sex, race. pathology, and HLA-matching of vaccine showed that none of these factors were statistically significantly related (P>0.10 in all instances) to clinical response (that is, to partial response or stable disease).

Figure 4:
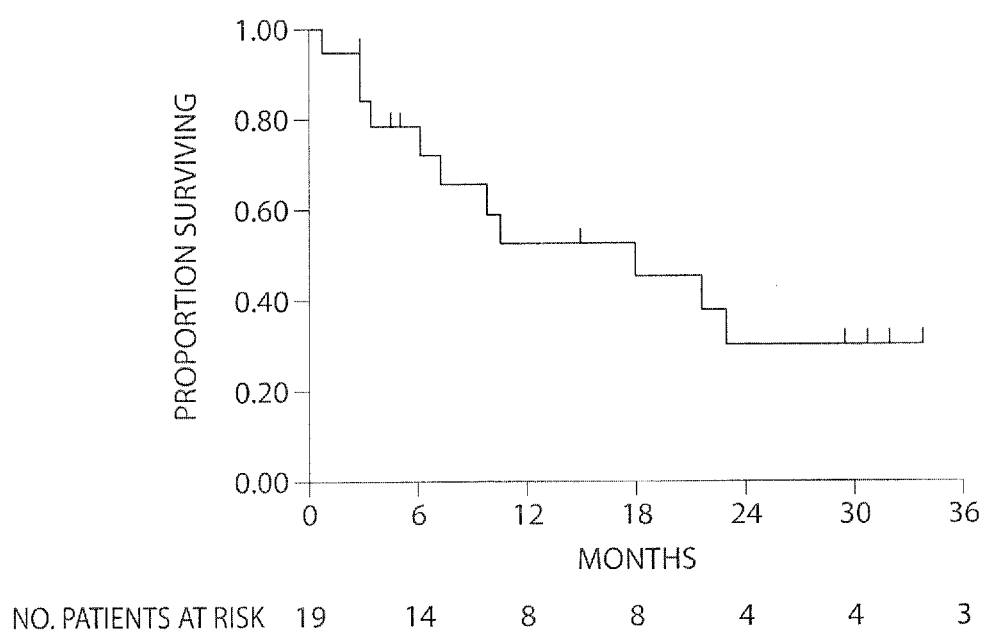
FIG. 4 shows overall survival for the 19 B7 vaccine-treated non-small-cell lung cancer study patients.

FIG. 4 shows the Kaplan-Meier estimate of overall survival for the 19 study patients (vertical tick marks indicate censored follow-up). The estimated median survival time is 18 months (90% CI, 7 to 23 months). Estimates of 1-year, 2-year, and 3-year overall survival are 52%(90% CI, 32% to 71%), 30% (90% CI, 11% to 49%), and 30% (90% CI, 11% to 49%), respectively. As of February 2004, death had occurred in 12 patients from 1 to 23 months after entry on study (Table 2). For the seven patients who are still alive, follow-up from study entry currently ranges from 10 to 40 months, with a median follow-up time of 36 months.

Univariate proportional hazards regression analysis suggested a possibly higher mortality rate in patients receiving HLA-matched vaccine (hazard ratio=4.5; 90% CI, 1.1 to 17.2), and a possibly lower mortality rate in patients with adenocarcinoma (hazard ratio=0.3; 90% CI, 0.1 to 1.0). A multivariate analysis involving five covariates (HLA-matching, age, sex, race, pathology), however, discounted an adverse effect of HLA-matching of vaccine on overall mortality; the corresponding adjusted hazard ratio was 1.9 (P=0.51). The adjusted hazard ratio for adenocarcinoma versus other pathologies was 0.2 (P=0.11), which is within the realm of chance at conventional levels of significance.

Immune Response to Vaccination. This cohort of patients had been heavily pretreated and carried large tumor burdens that are believed to be immunosuppressive. It was important, therefore, to establish whether the tumor vaccination protocol was able to induce a specific immune response in these patients. Since the CD8 CTL response is thought to be critical for tumor rejection, studies were focused on this arm of the immune system. To distinguish between nonspecific natural killer (NK) activity and CD8 CTL activity, a two-fold strategy was employed. First, CD8 cells were purified to eliminate NK cells by including anti-CD56 in the negative selection cocktail of antibodies. Second, the CD8 cells were challenged with K562, an NK target. NK contamination would result in high titers of cells responding to K562 challenge.

All but one patient had a measurable CD8 response after 6 weeks (three vaccinations) that tended to increase after 12 weeks and stabilize by 18 weeks (Table 6). In vitro challenge of patient CD8 cells with wild type A1 or A2 Transfected AD 100 did not reveal significant differences. Two patients (patient Nos. 1012 and 1019) could not be evaluated immunologically because there was no follow-up sample available for analysis due to early disease progression or adverse events. One patient had only a very modest response, while most other patients showed a strong, highly statistically significant response to vaccination (see pre- and postimmunization titers on challenge with vaccine cells, and lack of response to K562 control; FIG. 5, top panels). All but one patient had a measurable CD8 response after 6 weeks (three vaccinations) that tended to increase after 12 weeks and stabilize by IS weeks (Table 6). In vitro challenge of patient CD8 cells with wild type A1 or A2 transfected AD100 did not reveal significant differences. Two patients (patient Nos. 1012 and 1019) could not be evaluated immunologically because there was no follow-up sample available for analysis due to early disease progression or adverse events. One patient had only a very modest response, while most other patients showed a strong, highly statistically significant response to vaccination (see pre- and postimmunization titers on challenge with vaccine cells, and lack of response to K562 control; FIG. 5, top panels).

TABLE 6

CDB Response of Vaccinated Patients
Immune Response of CDB Cells to Vaccination*

| | 0 Weeks | | | | 6 Weeks | | | | 12 Weeks | | | | 18 Weeks | | | |
|---|---|---|---|---|---|---|---|---|---|---|---|---|---|---|---|---|
| HLA/Patient NO. | AD-wt | AD-A1 | AD-A2 | K562 | AD-wt | AD-A1 | AD-A2 | K562 | AD-wt | AD-A1 | AD-A2 | K562 | AD-wt | AD-A1 | AD-A2 | K562 |
| A2/1001 | 4 | 6.2 | 0 | 2.6 | 51 | 49 | 25 | 6 | | | | | | | | |
| A2/1002 | 12 | 19 | 41 | 170 | 30 | 55 | 65 | 96 | | | | | | | | |

TABLE 6-continued

CD8 Response of Vaccinated Patients
Immune Response of CD8 Cells to Vaccination*

| HLA/Patient NO. | 0 Weeks | | | | 6 Weeks | | | | 12 Weeks | | | | 18 Weeks | | | |
|---|---|---|---|---|---|---|---|---|---|---|---|---|---|---|---|---|
| | AD-wt | AD-A1 | AD-A2 | K562 | AD-wt | AD-A1 | AD-A2 | K562 | AD-wt | AD-A1 | AD-A2 | K562 | AD-wt | AD-A1 | AD-A2 | K562 |
| NO/1003 | 1 | 1 | 7 | 0 | 70 | 134 | 53 | 0 | 31 | 113 | 27 | 0 | 49 | 84 | 23 | 6 |
| NO/1004 | 0 | 0 | 0 | 5 | 321 | 424 | 195 | 0 | 216 | 232 | 150 | 0 | 283 | 450 | 130 | 0 |
| A1/1005 | 15 | 0 | 0 | 40 | 92 | 190 | 80 | 34 | | | | | | | | |
| NO/1006 | 13 | 17 | 12 | 11 | 156 | 152 | 132 | 16 | | | | | | | | |
| NO/1007 | 0 | 1 | 0 | 0 | 0 | 3 | 0 | 0 | 1 | 1 | 1 | 0 | 0 | 0 | 2 | 0 |
| NO/1008 | 5 | 6 | 4 | 10 | 97 | 180 | 48 | 3 | | | | | | | | |
| A2/1009 | 3 | 4 | 2 | 17 | 13 | 39 | 13 | 18 | | | | | | | | |
| A2/1010 | 8 | 8 | 4 | 14 | 48 | 87 | 46 | 5 | 120 | 163 | 88 | 8 | 185 | 241 | 157 | 17 |
| A2/1011 | 14 | 20 | 3 | 15 | 80 | 150 | 30 | 12 | 88 | 226 | 57 | 4 | | | | |
| A2/1013 | 18 | 150 | 5 | 0 | 155 | 300 | 164 | 3 | 175 | 154 | 178 | 3 | | | | |
| A2/1014 | 3 | 2 | 2 | 10 | 28 | 20 | 30 | 9 | 30 | 20 | 30 | 12 | 25 | 23 | 25 | 4 |
| A2/1015 | 0 | 0 | 0 | 0 | 0 | 0 | 0 | 0 | | | | | | | | |
| A1/1016 | 138 | 120 | 128 | 4 | 144 | 150 | 163 | 5 | 127 | 120 | 164 | 15 | | | | |
| A2/1017 | 0 | 11 | 0 | 4 | 100 | 200 | 200 | 3 | | | | | | | | |
| NO/1018 | 13 | 44 | 0 | 9 | 51 | 200 | 52 | 9 | | | | | | | | |

NOTE.
CD8 cells challenged at a ratio of 20:1 = CD8: tumor cell.
The mean spot number of quadruplicate values is given.
Abbreviations:
AD-wt, AD100 untransfected;
AD-A1 or AD-A2, AD100 transfected with HLA A1 or A2;
HLA NO, No HLA A1 or A2.
*Values are number of interferon-gamma secreting cells (spots per 20,000 CD8 cells) after in vitro challenge.

There was no statistically significant difference in the CD8 response depending on whether or not the patients were HLA-matched to the vaccine (Table 6). Most patients before vaccination had only low or absent immune response to vaccine cells, and equally low activity to challenge with K562. One patient (No. 1016) had strong prevaccination CD8 activity toward AD100 and only minimal activity toward K562 (FIG. 5, last panel), suggesting preexisting immune activity toward the tumor. Another patient (No. 1002) had high prevaccination K562 reactivity of his CD8 cells and low activity toward AD100. Vaccination increased reactivity toward AD100 and tended to decrease CD8 reactivity toward K562 when it was present.

The immune response of the six clinically-responding patients (FIG. 5B, lower panels) shows that CD8 titers to AD 100 stimulation continue to be elevated up to 150 weeks after cessation of vaccination.

Given the advanced stage of disease in patients enrolled in the studies disclosed herein, the evidence of some clinical benefit was unexpected and encouraging. Moreover, since the B7-vaccine tested here induced CD8 CTL responses, it may be that the CD8 response is causally related to the clinical outcome seen here. Additional studies are performed in the setting of minimal disease. Patients with early stage NSCLC (stage I/II) are vaccinated after surgery to decrease the chance of relapse and potentially prolong survival.

The results described in this example show that tumor progression can be slowed by vaccination and that this effect occurs regardless of whether or not patients are allogeneic to the HLA A1 or A2 locus of the vaccine. These findings also support indirect antigen presentation as being effective in promoting antitumor activity and that allogeneic MHC molecules enhance the effect.

Example 4: Establishment and Expansion of AD100-A1-B7.1 Cells

A human lung adenocarcinoma cell line (designated AD100) was established in 1994 at the University of Miami, derived from a patient with NSCLC. This cell line has been kept in culture in standard medium and is free of contamination by *Mycoplasma*, virus, or other adventitious agents. It is homogeneous, adherent to plastic, and grows at a rate of division of approximately 26 hours.

AD100 cells are transfected with plasmid cDNA, pBMG-Neo-B7.1 and pBMG-His-HLA A2 or with B45-Neo-CM-A1-B7.1. Transfected cells were selected with G418 and Histidinol. Verification of correct sequences was based on restriction analysis and the expression of the relevant gene products, namely G418 or histidinol resistance for the vector sequence, HLA A1, A2, and B7.1 expression for the transfected cDNA. The minimum requirement for their use as vaccine was the coexpression of HLA A1 or A2 plus B7.1 on at least 70% of the cells as shown in FIG. 1a for representative batches of vaccine cells.

AD100-A1-67.1 cells may be previously prepared and frozen in aliquots. The cryovial containing the cells is completely thawed rapidly using a 37° C. water bath and gentle swirls. The cells are then transferred the cells immediately to a previously prepared sterile 15 ml conical centrifuge tube kept on ice. To this 15 ml conical centrifuge tube, 9 ml of Complete Media 1 (IMDM; FBS Certified heat inactivated—final con. 9%; Gentamicin—final conc. 0.04 mg/ml) is slowly added 1 to 2 drops at a time, while gently swirling the tube in order to uniformly mix cells with media. This process should take 10 to 15 minutes. After all the media is added, the cells are centrifuged cells at 300×g (1200 rpm) for 10 minutes, at room temperature, with the brake set to "Low". The supernatant is then gently aspirated away and the cells are resuspend in 10 ml of Complete Media 2 (IMDM; FBS Certified heat inactivated—final con. 9%; Gentamicin—final conc. 0.04 mg/ml; Geneticin G-418—final conc. 1 mg/ml), equilibrated to room temperature.

A cell count and viability test, using Trypan Blue @1:10 dilution is then performed. Cells are then seeded at $2 \times 10^6$ cells per T-175 tissue culture flask containing 35 ml of Complete Media 2. The seeded flasks are then incubated for 3 to 5 days in a 37° C. incubator with 5% $CO_2$.

Feeding Cells for Working Cell Bank

The cells should not be disturb until the third day of culture, when an assessment of whether cells have attached to the flask should be made. On the 3rd day of culture, a percentage of cells that have attached needs to be estimated. If ≥70% of the cells have attached to the flask, the media needs to be changed. Old media should be removed using an aspirating pipette and 50 ml of fresh Complete Media 1 pre-warmed to 37° C. should be added to each flask. The flasks are then returned to 37° C. incubator with 5% $CO_2$ for further culture. If, when observing cells on the third day of culture, ≤70% of cells are deemed to be attached, they need to be left until the fifth day without changing media. After 3-5 days in culture, remove flasks from the 37° C. incubator and determine percentage of confluency. Cells need to be cultured until such time when they are deemed to be 90-95% confluent. The cells must be split when the confluency reaches 90-95% per flask.

Harvesting the Cells with Trypsin EDTA for Working Cell Bank

After the cells reach 90-95% confluency, the cells are harvested by aspirating off the supernatant and by adding 12 ml of Trypsin-EDTA pre-warmed to 37° C. to each flask. The cells are incubated at 37° C. in this solution for approximately 20 minutes. After incubation, the flask is vigorously shaken across its surface area, to ensure that the cells are no longer adhering to the flask. 13 ml of Complete is then added to neutralize Trypsin-EDTA reaction. The supernatant containing the cells that have detached from the flask is then collected and transferred it to a sterile 50 ml or 250 ml conical centrifuge tube. Cell suspensions from all the flasks should be combined and washed at the same time. The cells are then centrifuged at 300×g (1200 rpm) for 10 minutes, at room temperature with the brake set to "Low". The supernatant is then aspirated off and the cells are resuspend in 15-30 ml of pre-warmed (to 37° C.) Complete Media 2.

A cell count and viability test using Trypan Blue 1:10 dilution is them performed. New T-175 tissue culture flasks are then seeded at the density of $2.0 \times 10^6$ cells per flask, using pre-warmed (to 37° C.) Complete Media 2. The total volume of the Complete Media 2 in each T-175 tissue culture flask should be 35 ml.

The above harvesting and expanding process is repeated approximately every 7 days until 201 T-175 flasks can be seeded at one time. When this threshold is met, Complete Medium 2 is used to seed the cells for the final expansion. After the first 3-5 days of culture, when the cells have attached and are ready to be fed, change to Complete Medium 1 is used. When the cells reach 90-95% confluency, the cells are harvested as above. The cells are then washed twice in at least 200 ml of (4° C.) Wash Media (0.9% sodium chloride; 0.5% HAS; and 0.0067% USP sodium bicarbonate). After the second wash, the cell pellet is resuspend in Wash Media to the final volume of 200 ml. A cell count and viability test using 1:70 dilution of Trypan Blue is again performed. The cells are then irradiated at 12,000 rads using a Cobalt irradiator. The cells are now ready for cryopreservation.

Cryopreservation of Expanded AD100-A 1-B7.1 Cells

At least 80-120 cryovials should be labeled with cell identification, batch number, cell concentration, tech's initials, and date. The cells are then centrifuged at 4° C., 300×g (1200 rpm), for 10 minutes, with the brakes on. After which, the supernatant is aspirated off and the pelleted cells are placed on ice. The cells are then resuspend slowly with gentle mixing, to a concentration of $200 \times 10^6$/ml ice cold Wash Media. Ice cold Freezing Media (0.9% sodium chloride; 0.5% HAS; 0.0067% USP sodium bicarbonate; and 20% DMSO) is slowly added at a 1:1 ratio to have a cell concentration of $100 \times 10^6$/ml and DMSO concentration of 10%. The cells are then aliquoted at 0.5 ml ($50 \times 10^6$ cells) previously prepared cryovials on ice and then stored at −80° C. for 18-24 hours. After 24 hours, the frozen cells are transferred to the Liquid Nitrogen storage tank.

Throughout this application various publications have been referenced. The disclosures of these publications in their entireties are hereby incorporated by reference in this application in order to more fully describe the state of the art to which this invention pertains to the same extent as if each was specifically and individually indicated to be incorporated by reference. The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Example 5: 1. Phase 1 Trial Design and Results

Three vaccinations, each of which was spaced 2 weeks apart, comprised one course of treatment. At the end of the first course, patients who had evidence of stable disease or responding NSCLC (by computed tomography scans), and no to moderate toxicity (grade ≤2), were treated with a second course of vaccination. No patient was denied a second or third course of treatment because of toxicity.

In the absence of tumor progression or severe toxicity (grade ≥3), a third course of vaccination was given. No patients experienced drug-related toxicity of grade ≥3, and so all patients who did not progress were eligible for the third course of vaccination.

Therefore, a total of three courses, or nine total vaccinations, were possible in the study. Clinical and toxicity evaluations were done before and after each vaccination, and immunologic assessment was made before and after each course.

A. Survival Status and History of All Patients Tested in Trials.

Figure 7:
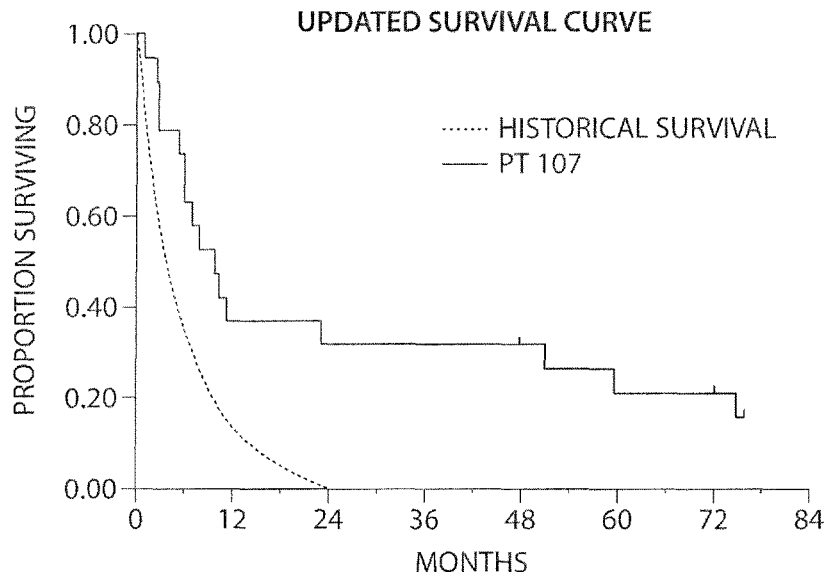
FIG. 7 illustrates the survival curve from initiation of phase I clinical trial to present or to last survivor.

The up-to-date survival curve is presented in FIG. 7. The full patient history and follow up is presented in Table 7.

B. Current Status of Responders.

Of six clinical responders, three have since died, the most recent in February 2007 (patient #14 below, and in Table 1). As of March 2007, there are three continuing survivors. The mean survival of the six clinical responders is currently 59+ months (median=~66+ (60 or 72+) months). The detailed status of the original six clinical responders is shown below (Patient # references to Table 7):

TABLE 7

| Patient # | Status | Survival |
|---|---|---|
| 4 | Dead | 23 mos. |
| 16 | Alive | 48+ mos. |
| 14 | Dead | 60 mos. |
| 10 | Alive | 72+ mos. |

TABLE 7-continued

| Patient # | Status | Survival |
|---|---|---|
| 7 | Dead | 75 mos. |
| 3 | Alive | 76+ mos. |

C. Up-to-Date Survival Curve (from Initiation of Trial to Present or to Last Survivor)

Please see FIG. 7.

D. Percentage of the Patients Responded or Had an Adverse Effect.

As seen in Table 8, 19 patients were enrolled into the trial. It should be noted that one patient was taken off study before receiving any vaccinations, but he is still counted among the 19 patients.

Six of the 19 patients (32%) responded clinically with either partial response (PR) or stable disease (SD).

Three of the 19 patients (16%) experienced adverse events (grade 1 or 2) which were judged to be potentially vaccine-related. These adverse events were comprised of: rash (1 patient), moderate arthritic pain in the joints (1 patient), and chest pain (1 patient). Additionally, four of the 19 patients (21%) developed some transient erythema at the vaccination site. The erythema is not considered to be an adverse event since it resolved within a week.

None of the 19 patients (0%) experienced drug-related serious adverse events (SAEs). All SAEs were judged to be not vaccine-related. Four of the 19 patients (21%) experienced non-drug-related SAEs.

TABLE 8

| Patient | Sex | HLA Type | Pathology | Location of Metastasis | Number of Vaccinations | Clinical Response | Additional Chemotherapy | Survival (weeks) | AE or SAE |
|---|---|---|---|---|---|---|---|---|---|
| 1 | F | A2 | A | B | 3 | PD | None | 26 | Rash |
| 2 | F | A2 | A | L | 3 | PD | Iressa | 43 | None |
| 3 | F | Non | A | P, L, A | 9 | SD | None | 328++ | None |
| 4 | F | Non | A | B | 9 | SD | Gemzar; Carboplatin | 100 | None |
| 5 | M | A1 | B | L | 3 | PD | None | 34 | None |
| 6 | M | Non | A | B, L | 3 | PD | Iressa; Temodar | 221 | None |
| 7 | M | Non | A | L | 8; 9 | SD | Revaccinated with PT 107; Tarceva (1 yr. later) | 324 | Pericardial Effusion* (recurrent) |
| 8 | F | Non | A | L | 3 | PD | Gemzar | 26 | None |
| 9 | M | A2 | U | L | 3 | PD | None | 12 | None |
| 10 | F | A2 | A | L, A | 9 | PR | None | 312++ | Joint pain |
| 11 | M | A2 | S | L | 3 | PD | None | 45 | Chest pain |
| 12 | M | A1 | S | A | 0 | PD | None | 13 | Renal Failure* |
| 13 | F | A2 | A | B | 4 | PD | None | 11 | Respiratory Failure* |
| 14 | F | A2 | S | L | 9 | SD | Iressa; Tarceva | 258† | None |
| 15 | F | A2 | A | L | 3 | PD | Iressa | 30 | None |
| 16 | F | A1 | B | L | 6 | SD | Velcade; Alimta Iressa | 207++ | None |
| 17 | F | A2 | B | Pl | 3 | PD | Gemzar; Navelbine | 23 | None |
| 18 | M | Non | B | Li, L, T | 3 | PD | None | 49 | None |

TABLE 8-continued

| Patient | Sex | HLA Type | Pathology | Location of Metastasis | Number of Vaccinations | Clinical Response | Additional Chemotherapy | Survival (weeks) | AE or SAE |
|---|---|---|---|---|---|---|---|---|---|
| 19 | F | A2 | U | N/Li | 1 | PD | None | 4 | Peridcardial Effusion* (tumor) |

Notes:
Follow up as of Feb. 21, 2007.
++ Still alive as of February 2007.
† Died February 2007.
* Adverse event was determined to be not related to vaccine.
Sex:
F = female
M = male
HLA Type:
A1 = HLA A1
A2 = HLA A2
Non = Non-HLA A1/A2
Pathology:
A = adenocarcinoma
B = bronchial carcinoma
S = squamous cell carcinoma
U - undifferentiated carcinoma
Location of Metastasis:
B = brain
L = lung
A = adrenal gland
P = pancreas
Pl = pleura
Li = liver
T = thoracic spinal column
Clinical Reponse (responders shown in red):
PD = progressive disease
SD = stable disease
PR = partial response E. Patients Response to Different Levels of Vaccine.

Figure 8:
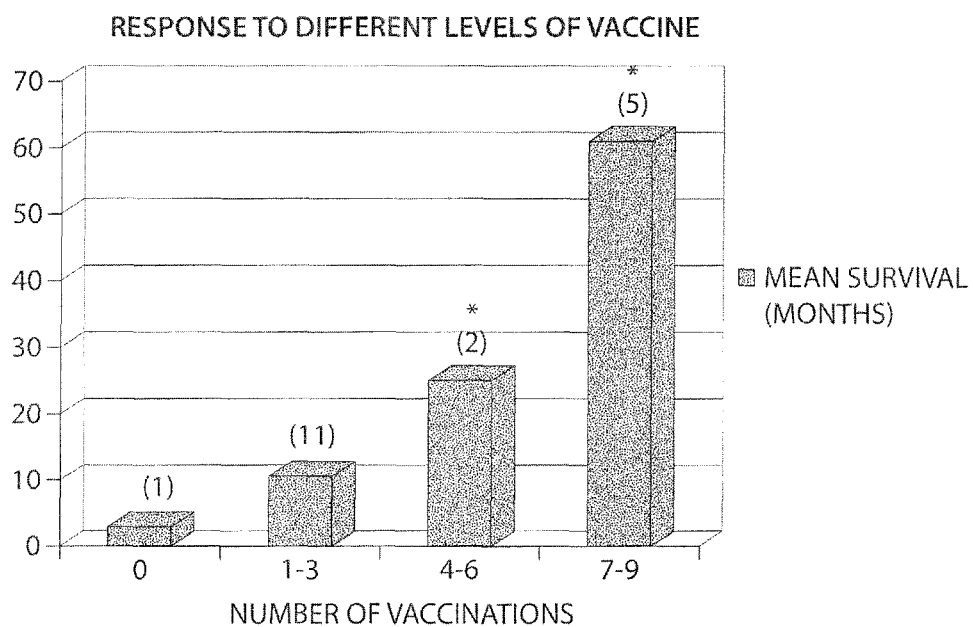
FIG. 8 illustrates patient response to different levels of vaccination. Patients who received a second or third course of vaccination fared better in terms of both clinical response and survival.

Please see the graph in FIG. 8 for further detail. Patients who received a second or third course of vaccination fared much better in terms of both clinical response and survival. All five patients who received 8 or 9 vaccinations were clinical responders. Of the clinical responders, 5 of 6 (83%) received 8 or 9 vaccinations in their initial therapy. Of the non-responders, 12 of 13 (92%) received 0-3 vaccinations.

F. Responder Breakdown Regarding Pathology of NSCLC Cell Type (Adenocarcinoma, Bronchoalveolar, Squamous and Undifferentiated).

Of the 6 clinical responders, the pathology was as follows: 4 had adenocarcinoma, 1 had bronchoalveolar carcinoma, and 1 had squamous cell carcinoma. On a percentage basis, 4 of 11 (36%) patients with adenocarcinoma responded, 1 of 3 (33%) patients with bronchoalveolar carcinoma responded, 1 of 3 (33%) patients with squamous cell carcinoma responded, and 0 of 2 (0%) patients with undifferentiated carcinoma responded. Please see Table 1 for further detail.

G. Comparison of Matched and Non-Matched HLA in Trials and Patients.

A multivariate analysis involving five covariates (HLA-matching, sex, race, pathology) showed no statistical significance of HLA-matching on overall mortality.

Of the 19 patients, 13 were matched (3 at A1, 10 at A2), and 6 were non-matched. Of the 6 clinical responders, 3 were HLA matched, and 3 were non-matched. Among matched patients, 1 of the 3 (33%) A1-matched patients were clinical responders, and 2 of 10 (20%) A2-matched patients were clinical responders. Among non-matched patients, 3 of 6 (50%) were clinical responders.

It should be noted that logistic regression analyses of age, sex, race, pathology, and HLA-matching of vaccine showed that none of these factors were statistically significantly related ($P \geq 0.10$ in all instances) to clinical response.

Univariate proportional hazards regression analysis suggested a possibly higher mortality rate in patients receiving HLA-matched vaccine (hazard ratio=4.5; 90% CI, 1.1 to 17.2), and a possibly lower mortality rate in patients with adenocarcinoma (hazard ratio=0.3; 90% CI, 0.1 to 1.0). A multivariate analysis involving five covariates (HLA-matching, age, sex, race, pathology) however, discounted an adverse effect of HLA-matching of vaccine on overall mortality; the corresponding adjusted hazard ratio was 1.9 (P=0.51). The adjusted hazard ratio for adenocarcinoma versus other pathologies was 0.2 (P=0.11), which is within the realm of chance at conventional levels of significance.

```
BPV-1-B7.1-HLA A1 vector sequence
XbaI SEQ ID NO: 1
      ~~~~~~
    1 TCTAGAGAGC TTGGCCCATT GCATACGTTG TATCCATATC ATAATATGTA
      AGATCTCTCG AACCGGGTAA CGTATGCAAC ATAGGTATAG TATTATACAT 51 CATTTATATT GGCTCATGTC CAACATTACC GCCATGTTGA CATTGATTAT
      GTAAATATAA CCGAGTACAG GTTGTAATGG CGGTACAACT GTAACTAATA
```

-continued

```
 101 TGACTAGTTA TTAATAGTAA TCAATTACGG GGTCATTAGT TCATAGCCCA
     ACTGATCAAT AATTATCATT AGTTAATGCC CCAGTAATCA AGTATCGGGT

151 TATATGGAGT TCCGCGTTAC ATAACTTACG GTAAATGGCC CGCCTGGCTG
     ATATACCTCA AGGCGCAATG TATTGAATGC CATTTACCGG GCGGACCGAC

201 ACCGCCCAAC GACCCCCGCC CATTGACGTC AATAATGACG TATGTTCCCA
     TGGCGGGTTG CTGGGGGCGG GTAACTGCAG TTATTACTGC ATACAAGGGT

251 TAGTAACGCC AATAGGGACT TTCCATTGAC GTCAATGGGT GGAGTATTTA
     ATCATTGCGG TTATCCCTGA AAGGTAACTG CAGTTACCCA CCTCATAAAT

301 CGGTAAACTG CCCACTTGGC AGTACATCAA GTGTATCATA TGCCAAGTAC
     GCCATTTGAC GGGTGAACCG TCATGTAGTT CACATAGTAT ACGGTTCATG

351 GCCCCCTATT GACGTCAATG ACGGTAAATG GCCCGCCTGG CATTATGCCC
     CGGGGGATAA CTGCAGTTAC TGCCATTTAC CGGGCGGACC GTAATACGGG

401 AGTACATGAC CTTATGGGAC TTTCCTACTT GGCAGTACAT CTACGTATTA
     TCATGTACTG GAATACCCTG AAAGGATGAA CCGTCATGTA GATGCATAAT

451 GTCATCGCTA TTACCATGGT GATGCGGTTT TGGCAGTACA TCAATGGGCG
     CAGTAGCGAT AATGGTACCA CTACGCCAAA ACCGTCATGT AGTTACCCGC

501 TGGATAGCGG TTTGACTCAC GGGGATTTCC AAGTCTCCAC CCCATTGACG
     ACCTATCGCC AAACTGAGTG CCCCTAAAGG TTCAGAGGTG GGGTAACTGC

551 TCAATGGGAG TTTGTTTTGG CACCAAAATC AACGGGACTT TCCAAAATGT
     AGTTACCCTC AAACAAAACC GTGGTTTTAG TTGCCCTGAA AGGTTTTACA

601 CGTAACAACT CCGCCCCATT GACGCAAATG GGCGGTAGGC GTGTACGGTG
     GCATTGTTGA GGCGGGGTAA CTGCGTTTAC CCGCCATCCG CACATGCCAC

651 GGAGGTCTAT ATAAGCAGAG CTCGTTTAGT GAACCGTCAG ATCGCCTGGA
     CCTCCAGATA TATTCGTCTC GAGCAAATCA CTTGGCAGTC TAGCGGACCT

701 GACGCCATCC ACGCTGTTTT GACCTCCATA GAAGACACCG GGACCGATCC
     CTGCGGTAGG TGCGACAAAA CTGGAGGTAT CTTCTGTGGC CCTGGCTAGG

751 AGCCTCCGGT CGATCGACCG ATCCTGAGAA CTTCAGGGTG AGTTTGGGGA
     TCGGAGGCCA GCTAGCTGGC TAGGACTCTT GAAGTCCCAC TCAAACCCCT

801 CCCTTGATTG TTCTTTCTTT TTCGCTATTG TAAAATTCAT GTTATATGGA
     GGGAACTAAC AAGAAAGAAA AAGCGATAAC ATTTTAAGTA CAATATACCT

851 GGGGGCAAAG TTTTCAGGGT GTTGTTTAGA ATGGGAAGAT GTCCCTTGTA
     CCCCCGTTTC AAAAGTCCCA CAACAAATCT TACCCTTCTA CAGGGAACAT

901 TCACCATGGA CCCTCATGAT AATTTTGTTT CTTTCACTTT CTACTCTGTT
     AGTGGTACCT GGGAGTACTA TTAAAACAAA GAAAGTGAAA GATGAGACAA

951 GACAACCATT GTCTCCTCTT ATTTTCTTTT CATTTTCTGT AACTTTTTCG
     CTGTTGGTAA CAGAGGAGAA TAAAAGAAAA GTAAAGACA TTGAAAAAGC

1001 TTAAACTTTA GCTTGCATTT GTAACGAATT TTTAAATTCA CTTTTGTTTA
     AATTTGAAAT CGAACGTAAA CATTGCTTAA AAATTTAAGT GAAAACAAAT

1051 TTTGTCAGAT TGTAAGTACT TTCTCTAATC ACTTTTTTTT CAAGGCAATC
     AAACAGTCTA ACATTCATGA AAGAGATTAG TGAAAAAAAA GTTCCGTTAG

1101 AGGGTATATT ATATTGTACT TCAGCACAGT TTTAGAGAAC AATTGTTATA
     TCCCATATAA TATAACATGA AGTCGTGTCA AAATCTCTTG TTAACAATAT

1151 ATTAAATGAT AAGGTAGAAT ATTTCTGCAT ATAAATTCTG GCTGGCGTGG
     TAATTTACTA TTCCATCTTA TAAAGACGTA TATTTAAGAC CGACCGCACC

1201 AAATATTCTT ATTGGTAGAA ACAACTACAC CCTGGTCATC ATCCTGCCTT
     TTTATAAGAA TAACCATCTT GTTGATGTG GGACCAGTAG TAGGACGGAA

1251 TCTCTTTATG GTTACAATGA TATACACTGT TTGAGATGAG GATAAAATAC
     AGAGAAATAC CAATGTTACT ATATGTGACA AACTCTACTC CTATTTTATG

1301 TCTGAGTCCA AACCGGGCCC CTCTGCTAAC CATGTTCATG CCTTCTTCTC
     AGACTCAGGT TTGGCCCGGG GAGACGATTG GTACAAGTAC GGAAGAAGAG

1351 TTTCCTACAG CTCCTGGGCA ACGTGCTGGT TGTTGTGCTG TCTCATCATT
     AAAGGATGTC GAGGACCCGT TGCACGACCA ACAACACGAC AGAGTAGTAA
                    XhoI        Start B7.1 (CD80)
          SEQ ID NO: 2      MetGly HisThrArg ArgGlnGly
                    ~~~~~~       ~~~~~~~~~~~~~~~~~~~~~~~~~
```

-continued

```
1401 TTGGCAAAGA ATTCCTCGAG GAAGCCATGG GCCACACACG GAGGCAGGGA
     AACCGTTTCT TAAGGAGCTC CTTCGGTACC CGGTGTGTGC CTCCGTCCCT
     ThrSerProSer LysCysPro TyrLeuAsn PhePheGlnLeu LeuValLeu
     ~~~~~~~~~~~~~~~~~~~~~~~~~~~~~~~~~~~~~~~~~~~~~~~~~~~~

1451 ACATCACCAT CCAAGTGTCC ATACCTCAAT TTCTTTCAGC TCTTGGTGCTG
     TGTAGTGGTA GGTTCACAGG TATGGAGTTA AAGAAAGTCG AGAACCACGA
     AlaGlyLeu SerHisPheCys SerGlyVal IleHisVal ThrLysGluVal
     ~~~~~~~~~~~~~~~~~~~~~~~~~~~~~~~~~~~~~~~~~~~~~~~~~~~

1501 GCTGGTCTT TCTCACTTCT GTTCAGGTGT TATCCACGTG ACCAAGGAAG
     CCGACCAGAA AGAGTGAAGA CAAGTCCACA ATAGGTGCAC TGGTTCCTTC
     •VLysGluVal AlaThrLeu SerCysGlyHis AsnValSer ValGluGlu
     ~~~~~~~~~~~~~~~~~~~~~~~~~~~~~~~~~~~~~~~~~~~~~~~~~~~

1551 TGAAAGAAGT GGCAACGCTG TCCTGTGGTC ACAATGTTTC TGTTGAAGAG
     ACTTTCTTCA CCGTTGCGAC AGGACACCAG TGTTACAAAG ACAACTTCTC
     LeuAlaGlnThr ArgIleTyr TrpGlnLys GluLysLysMet ValLeuThr •
     ~~~~~~~~~~~~~~~~~~~~~~~~~~~~~~~~~~~~~~~~~~~~~~~~~~~

1601 CTGGCACAAA CTCGCATCTA CTGGCAAAAG GAGAAGAAAA TGGTGCTGAC
     GACCGTGTTT GAGCGTAGAT GACCGTTTTC CTCTTCTTTT ACCACGACTG
     •MetMetSer GlyAspMetAsn IleTrpPro GluTyrLys AsnArgThrIle •
     ~~~~~~~~~~~~~~~~~~~~~~~~~~~~~~~~~~~~~~~~~~~~~~~~~~~

1651 TATGATGTCT GGGGACATGA ATATATGGCC CGAGTACAAG AACCGGACCA
     ATACTACAGA CCCCTGTACT TATATACCGG GCTCATGTTC TTGGCCTGGT
     •IPheAspIle ThrAsnAsn LeuSerIleVal IleLeuAla LeuArgPro
     ~~~~~~~~~~~~~~~~~~~~~~~~~~~~~~~~~~~~~~~~~~~~~~~~~~~

1701 TCTTTGATAT CACTAATAAC CTCTCCATTG TGATCCTGGC TCTGCGCCCA
     AGAAACTATA GTGATTATTG GAGAGGTAAC ACTAGGACCG AGACGCGGGT
     SerAspGluGly ThrTyrGlu CysValVal LeuLysTyrGlu LysAspAla •
     ~~~~~~~~~~~~~~~~~~~~~~~~~~~~~~~~~~~~~~~~~~~~~~~~~~~

1751 TCTGACGAGG GCACATACGA GTGTGTTGTT CTGAAGTATG AAAAAGACGC
     AGACTGCTCC CGTGTATGCT CACACAACAA GACTTCATAC TTTTTCTGCG
     •PheLysArg GluHisLeuAla GluValThr LeuSerVal LysAlaAspPhe •
     ~~~~~~~~~~~~~~~~~~~~~~~~~~~~~~~~~~~~~~~~~~~~~~~~~~~

1801 TTTCAAGCGG GAACACCTGG CTGAAGTGAC GTTATCAGTC AAAGCTGACT
     AAAGTTCGCC CTTGTGGACC GACTTCACTG CAATAGTCAG TTTCGACTGA
     •PProThrPro SerIleSer AspPheGluIle ProThrSer AsnIleArg
     ~~~~~~~~~~~~~~~~~~~~~~~~~~~~~~~~~~~~~~~~~~~~~~~~~~~

1851 TCCCTACACC TAGTATATCT GACTTTGAAA TTCCAACTTC TAATATTAGA
     AGGGATGTGG ATCATATAGA CTGAAACTTT AAGGTTGAAG ATTATAATCT
     ArgIleIleCys SerThrSer GlyGlyPhe ProGluProHis LeuSerTrp •
     ~~~~~~~~~~~~~~~~~~~~~~~~~~~~~~~~~~~~~~~~~~~~~~~~~~~

1901 AGGATAATTT GCTCAACCTC TGGAGGTTTT CCAGAGCCTC ACCTCTCCTG
     TCCTATTAAA CGAGTTGGAG ACCTCCAAAA GGTCTCGGAG TGGAGAGGAC
     •LeuGluAsn GlyGluGluLeu AsnAlaIle AsnThrThr ValSerGlnAsp •
     ~~~~~~~~~~~~~~~~~~~~~~~~~~~~~~~~~~~~~~~~~~~~~~~~~~~

1951 GTTGGAAAAT GGAGAAGAAT TAAATGCCAT CAACACAACA GTTTCCCAAG
     CAACCTTTTA CCTCTTCTTA ATTTACGGTA GTTGTGTTGT CAAAGGGTTC
     •AProGluThr GluLeuTyr AlaValSerSer LysLeuAsp PheAsnMet
     ~~~~~~~~~~~~~~~~~~~~~~~~~~~~~~~~~~~~~~~~~~~~~~~~~~~

2001 ATCCTGAAAC TGAGCTCTAT GCTGTTAGCA GCAAACTGGA CTTCAATATG
     TAGGACTTTG ACTCGAGATA CGACAATCGT CGTTTGACCT GAAGTTATAC
     ThrThrAsnHis SerPheMet CysLeuIle LysTyrGlyHis LeuArgVal •
     ~~~~~~~~~~~~~~~~~~~~~~~~~~~~~~~~~~~~~~~~~~~~~~~~~~~

2051 ACAACCAACC ACAGCTTCAT GTGTCTCATC AAGTATGGAC ATTTAAGAGT
     TGTTGGTTGG TGTCGAAGTA CACAGAGTAG TTCATACCTG TAAATTCTCA
     •AsnGlnThr PheAsnTrpAsn ThrThrLys GlnGluHis PheProAspAsn •
     ~~~~~~~~~~~~~~~~~~~~~~~~~~~~~~~~~~~~~~~~~~~~~~~~~~~

2101 GAATCAGACC TTCAACTGGA ATACAACCAA GCAAGAGCAT TTTCCTGATA
     CTTAGTCTGG AAGTTGACCT TATGTTGGTT CGTTCTCGTA AAAGGACTAT
     •ALeuLeuPro SerTrpAla IleThrLeuIle SerValAsn GlyIlePhe
     ~~~~~~~~~~~~~~~~~~~~~~~~~~~~~~~~~~~~~~~~~~~~~~~~~~~

2151 ACCTGCTCCC ATCCTGGGCC ATTACCTTAA TCTCAGTAAA TGGAATTTTT
     TGGACGAGGG TAGGACCCGG TAATGGAATT AGAGTCATTT ACCTTAAAAA
     ValIleCysCys LeuThrTyr CysPheAla ProArgCysArg GluArgArg •
     ~~~~~~~~~~~~~~~~~~~~~~~~~~~~~~~~~~~~~~~~~~~~~~~~~~~

2201 GTGATATGCT GCCTGACCTA CTGCTTTGCC CCAAGATGCA GAGAGAGAAG
```

-continued

```
          CACTATACGA CGGACTGGAT GACGAAACGG GGTTCTACGT CTCTCTCTTC
          •ArgAsnGlu ArgLeuArgArg GluSerVal ArgProVal ***
          ~~~~~~~~~~~~~~~~~~~~~~~~~~~~~~~~~~~~~~~~~~~~Stop 2251  GAGGAATGAG AGATTGAGAA GGGAAAGTGT ACGCCCTGTA TAACAGACTA
          CTCCTTACTC TCTAACTCTT CCCTTTCACA TGCGGGACAT ATTGTCTGAT
                                                            XhoI
                                                            ~~~~

2301  GTCAAATTAA GCCGAATTCT GCAGATATCC ATCACACTGG CGGCCGCTCG
          CAGTTTAATT CGGCTTAAGA CGTCTATAGG TAGTGTGACC GCCGGCGAGC
          XhoI
          ~~

2351  AGGAATTCAC TCCTCAGGTG CAGGCTGCCT ATCAGAAGGT GGTGGCTGGT
          TCCTTAAGTG AGGAGTCCAC GTCCGACGGA TAGTCTTCCA CCACCGACCA

2401  GTGGCCAATG CCCTGGCTCA CAAATACCAC TGAGATCTTT TTCCCTCTGC
          CACCGGTTAC GGGACCGAGT GTTTATGGTG ACTCTAGAAA AAGGGAGACG

2451  CAAAAATTAT GGGGACATCA TGAAGCCCCT TGAGCATCTG ACTTCTGGCT
          GTTTTTAATA CCCCTGTAGT ACTTCGGGGA ACTCGTAGAC TGAAGACCGA

2501  AATAAAGGAA ATTTATTTTC ATTGCAATAG TGTGTTGGAA TTTTTTGTGT
          TTATTTCCTT TAAATAAAAG TAACGTTATC ACACAACCTT AAAAAACACA

2551  CTCTCACTCG GAAGGACATA TGGGAGGGCA AATCATTTAA AACATCAGAA
          GAGAGTGAGC CTTCCTGTAT ACCCTCCCGT TTAGTAAATT TTGTAGTCTT

2601  TGAGTATTTG GTTTAGAGTT TGGCAACATA TGCCCATATG CTGGCTGCCA
          ACTCATAAAC CAAATCTCAA ACCGTTGTAT ACGGGTATAC GACCGACGGT

2651  TGAACAAAGG TTGGCTATAA AGAGGTCATC AGTATATGAA ACAGCCCCCT
          ACTTGTTTCC AACCGATATT TCTCCAGTAG TCATATACTT TGTCGGGGGA

2701  GCTGTCCATT CCTTATTCCA TAGAAAAGCC TTGACTTGAG GTTAGATTTT
          CGACAGGTAA GGAATAAGGT ATCTTTTCGG AACTGAACTC CAATCTAAAA

2751  TTTTATATTT TGTTTTGTGT TATTTTTTTC TTTAACATCC CTAAAATTTT
          AAAATATAAA ACAAAACACA ATAAAAAAAG AAATTGTAGG GATTTTAAAA

2801  CCTTACATGT TTTACTAGCC AGATTTTTCC TCCTCTCCTG ACTACTCCCA
          GGAATGTACA AAATGATCGG TCTAAAAGG AGGAGAGGAC TGATGAGGGT
                                                        BamHI
                                                        ~~~~~~~

2851  GTCATAGCTG TCCCTCTTCT CTTATGGAGA TCCCTCGACG GATCCCTAGA
          CAGTATCGAC AGGGAGAAGA GAATACCTCT AGGGAGCTGC CTAGGGATCT

2901  GTCGAGGCGA TGCGGCGCAG CACCATGGCC TGAAATAACC TCTGAAAGAG
          CAGCTCCGCT ACGCCGCGTC GTGGTACCGG ACTTATTGG AGACTTTCTC

2951  GAACTTGGTT AGGTACCTTG GTTTTTAATA CCAGCCTGGA GTAGAGCAGA
          CTTGAACCAA TCCATGGAAC CAAAAATTTT GGTCGGACCT CATCTCGTCT

3001  TGGGTTAAGG TGAGTGACCC CTCAGCCCTG GACATTCTTA GATGAGCCCC
          ACCCAATTCC ACTCACTGGG GAGTCGGGAC CTGTAAGAAT CTACTCGGGG

3051  CTCAGGAGTA GAGAATAATG TTGAGATGAG TTCTGTTGGC TAAAATAATC
          GAGTCCTCAT CTCTTATTAC AACTCTACTC AAGACAACCG ATTTTATTAG

3101  AAGGCTAGTC TTTATAAAAC TGTCTCCTCT TCTCCTAGCT TCGATCCAGA
          TTCCGATCAG AAATATTTTG ACAGAGGAGA AGAGGATCGA AGCTAGGTCT

3151  GAGAGACCTG GCGGAGCTG GTCGCTGCTC AGGAACTCCA GGAAAGGAGA
          CTCTCTGGAC CCGCCTCGAC CAGCGACGAG TCCTTGAGGT CCTTTCCTCT

3201  AGCTGAGGTT ACCACGCTGC GAATGGGTTT ACGGAGATAG CTGGCTTTCC
          TCGACTCCAA TGGTGCGACG CTTACCCAAA TGCCTCTATC GACCGAAAGG

3251  GGGGTGAGTT CTCGTAAACT CCAGAGCAGC GATAGGCCGT AATATCGGGG
          CCCCACTCAA GAGCATTTGA GGTCTCGTCG CTATCCGGCA TTATAGCCCC

3301  AAAGCACTAT AGGGACATGA TGTTCCACAC GTCACATGGG TCGTCCTATC
          TTTCGTGATA TCCCTGTACT ACAAGGTGTG CAGTGTACCC AGCAGGATAG

3351  CGAGCCAGTC GTGCCAAAGG GGCGGTCCCG CTGTGCACAC TGGCGCTCCA
          GCTCGGTCAG CACGGTTTCC CCGCCAGGGC GACACGTGTG ACCGCGAGGT

3401  GGGAGCTCTG CACTCCGCCC GAAAAGTGCG CTCGGCTCTG CCAGGACGCG
          CCCTCGAGAC GTGAGGCGGG CTTTTCACGC GAGCCGAGAC GGTCCTGCGC
```

-continued

```
3451 GGGCGCGTGA CTATGCGTGG GCTGGAGCAA CCGCCTGCTG GGTGCAAACC
     CCCGCGCACT GATACGCACC CGACCTCGTT GGCGGACGAC CCACGTTTGG

3501 CTTTGCGCCC GGACTCGTCC AACGACTATA AAGAGGGCAG GCTGTCCTCT
     GAAACGCGGG CCTGAGCAGG TTGCTGATAT TTCTCCCGTC CGACAGGAGA

3551 AAGCGTCACC ACGACTTCAA CGTCCTGAGT ACCTTCTCCT CACTTACTCC
     TTCGCAGTGG TGCTGAAGTT GCAGGACTCA TGGAAGAGGA GTGAATGAGG
                                                  SalI
                                                  ~~~~~

3601 GTAGCTCCAG CTTCACCACC AAGCTCCTCG ACGTCGACCC CAGACGCCGA
     CATCGAGGTC GAAGTGGTGG TTCGAGGAGC TGCAGCTGGG GTCTGCGGCT
Start SEQ ID NO: 3
     ~~~~~~~~~~~~~~~~~~~~~~~~~~~~~~~~~~~~~~~~~~~~~~~~~~~~

HLA A1   MetAlaVal MetAlaPro ArgThrLeuLeu LeuLeuLeu SerGlyAla
3651 GGATGGCCGT CATGGCGCCC CGAACCCTCC TCCTGCTACT CTCGGGGGCC
     CCTACCGGCA GTACCGCGGG GCTTGGGAGG AGGACGATGA GAGCCCCCGG
     ~~~~~~~~~~~~~~~~~~~~~~~~~~~~~~~~~~~~~~~~~~~~~~~~~~~~

LeuAlaLeuThr GluThrTrp AlaGlySer HisSerMetArg TyrPhePhe •
3701 CTGGCCCTGA CCCAGACCTG GGCGGGCTCC CACTCCATGA GGTATTTCTT
     GACCGGGACT GGGTCTGGAC CCGCCCGAGG GTGAGGTACT CCATAAAGAA
     ~~~~~~~~~~~~~~~~~~~~~~~~~~~~~~~~~~~~~~~~~~~~~~~~~~~~

•ThrSerVal SerArgProGly ArgGlyGlu ProArgPhe IleAlaValGly •
3751 CACATCCGTG TCCCGGCCCG GCCGCGGGGA GCCCCGCTTC ATCGCCGTGG
     GTGTAGGCAC AGGGCCGGGC CGGCGCCCCT CGGGGCGAAG TAGCGGCACC
     ~~~~~~~~~~~~~~~~~~~~~~~~~~~~~~~~~~~~~~~~~~~~~~~~~~~~

•GTyrValAsp AspThrGln PheValArgPhe AspSerAsp AlaAlaSer
3801 GCTACGTGGA CGACACGCAG TTCGTGCGGT TCGACAGCGA CGCCGCGAGC
     CGATGCACCT GCTGTGCGTC AAGCACGCCA AGCTGTCGCT GCGGCGCTCG
     ~~~~~~~~~~~~~~~~~~~~~~~~~~~~~~~~~~~~~~~~~~~~~~~~~~~~

GlnLysMetGlu ProArgAla ProTrpIle GluGlnGluGly ProGluTyr •
3851 CAGAAGATGG AGCCGCGGGC GCCGTGGATA GAGCAGGAGG GGCCGGAGTA
     GTCTTCTACC TCGGCGCCCG CGGCACCTAT CTCGTCCTCC CCGGCCTCAT
     ~~~~~~~~~~~~~~~~~~~~~~~~~~~~~~~~~~~~~~~~~~~~~~~~~~~~

•TrpAspGln GluThrArgAsn MetLysAla HisSerGln ThrAspArgAla •
3901 TTGGGACCAG GAGACACGGA ATATGAAGGC CCACTCACAG ACTGACCGAG
     AACCCTGGTC CTCTGTGCCT TATACTTCCG GGTGAGTGTC TGACTGGCTC
     ~~~~~~~~~~~~~~~~~~~~~~~~~~~~~~~~~~~~~~~~~~~~~~~~~~~~

•AAsnLeuGly ThrLeuArg GlyTyrTyrAsn GlnSerGlu AspGlySer
3951 CGAACCTGGG GACCCTGCGC GGCTACTACA ACCAGAGCGA GGACGGTTCT
     GCTTGGACCC CTGGGACGCG CCGATGATGT TGGTCTCGCT CCTGCCAAGA
     ~~~~~~~~~~~~~~~~~~~~~~~~~~~~~~~~~~~~~~~~~~~~~~~~~~~~

HisThrIleGln IleMetTyr GlyCysAsp ValGlyProAsp GlyArgPhe •
4001 CACACCATCC AGATAATGTA TGGCTGCGAC GTGGGGCCGG ACGGGCGCTT
     GTGTGGTAGG TCTATTACAT ACCGACGCTG CACCCCGGCC TGCCCGCGAA
     ~~~~~~~~~~~~~~~~~~~~~~~~~~~~~~~~~~~~~~~~~~~~~~~~~~~~

•LeuArgGly TyrArgGlnAsp AlaTyrAsp GlyLysAsp TyrIleAlaLeu •
4051 CCTCCGCGGG TACCGGCAGG ACGCCTACGA CGGCAAGGAT TACATCGCCC
     GGAGGCGCCC ATGGCCGTCC TGCGGATGCT GCCGTTCCTA ATGTAGCGGG
     ~~~~~~~~~~~~~~~~~~~~~~~~~~~~~~~~~~~~~~~~~~~~~~~~~~~~

•LAsnGluAsp LeuArgSer TrpThrAlaAla AspMetAla AlaGlnIle
4101 TGAACGAGGA CCTGCGCTCT TGGACCGCGG CGGACATGGC GGCTCAGATC
     ACTTGCTCCT GGACGCGAGA ACCTGGCGCC GCCTGTACCG CCGAGTCTAG
     ~~~~~~~~~~~~~~~~~~~~~~~~~~~~~~~~~~~~~~~~~~~~~~~~~~~~

ThrLysArgLys TrpGluAla AlaHisAla AlaGluGlnArg ArgValTyr •
4151 ACCAAGCGCA AGTGGGAGGC GGCCCATGCG GCGGAGCAGC GGAGAGTCTA
     TGGTTCGCGT TCACCCTCCG CCGGGTACGC CGCCTCGTCG CCTCTCAGAT
     ~~~~~~~~~~~~~~~~~~~~~~~~~~~~~~~~~~~~~~~~~~~~~~~~~~~~

•LeuAspGly ArgCysValAsp GlyLeuArg ArgTyrLeu GluAsnGlyLys •
4201 CCTGGATGGC CGGTGCGTGG ACGGGCTCCG CAGATACCTG GAGAACGGGA
     GGACCTACCG GCCACGCACC TGCCCGAGGC GTCTATGGAC CTCTTGCCCT
     ~~~~~~~~~~~~~~~~~~~~~~~~~~~~~~~~~~~~~~~~~~~~~~~~~~~~

•LGluThrLeu GlnArgThr AspProProLys ThrHisMet ThrHisHis
4251 AGGAGACGCT GCAGCGCACG GACCCCCCA AGACACATAT GACCCACCAC
     TCCTCTGCGA CGTCGCGTGC CTGGGGGGT TCTGTGTATA CTGGGTGGTG
     ~~~~~~~~~~~~~~~~~~~~~~~~~~~~~~~~~~~~~~~~~~~~~~~~~~~~
```

```
            ProIleSerAsp HisGluAla ThrLeuArg CysTrpAlaLeu GlyPheTyr •
       4301 CCCATCTCTG ACCATGAGGC CACCCTGAGG TGCTGGGCCC TGGGCTTCTA
            GGGTAGAGAC TGGTACTCCG GTGGGACTCC ACGACCCGGG ACCCGAAGAT
            ~~~~~~~~~~~~~~~~~~~~~~~~~~~~~~~~~~~~~~~~~~~~~~~~~~~~

•ProAlaGlu IleThrLeuThr TrpGlnArg AspGlyGlu AspGlnThrGln •
       4351 CCCTGCGGAG ATCACACTGA CCTGGCAGCG GGATGGGGAG GACCAGACCC
            GGGACGCCTC TAGTGTGACT GGACCGTCGC CCTACCCCTC CTGGTCTGGG
            ~~~~~~~~~~~~~~~~~~~~~~~~~~~~~~~~~~~~~~~~~~~~~~~~~~~

•GAspThrGlu LeuValGlu ThrArgProAla GlyAspGly ThrPheGln
       4401 AGGACACGGA GCTCGTGGAG ACCAGGCCTG CAGGGGATGG AACCTTCCAG
            TCCTGTGCCT CGAGCACCTC TGGTCCGGAC GTCCCCTACC TTGGAAGGTC
            ~~~~~~~~~~~~~~~~~~~~~~~~~~~~~~~~~~~~~~~~~~~~~~~~~~

LysTrpAlaAla ValValVal ProSerGly GluGluGlnArg TyrThrCys •
       4451 AAGTGGGCGG CTGTGGTGGT GCCTTCTGGA GAGGAGCAGA GATACACCTG
            TTCACCCGCC GACACCACCA CGGAAGACCT CTCCTCGTCT CTATGTGGAC
            •HisValGln HisGluGlyLeu ProLysPro LeuThrLeu ArgTrpGluLeu •
            ~~~~~~~~~~~~~~~~~~~~~~~~~~~~~~~~~~~~~~~~~~~~~~~~~~~

4501 CCATGTGCAG CATGAGGGTC TGCCCAAGCC CCTCACCCTG AGATGGGAGC
            GGTACACGTC GTACTCCCAG ACGGGTTCGG GGAGTGGGAC TCTACCCTCG
            •LSerSerGln ProThrIle ProIleValGly IleIleAla GlyLeuVal
            ~~~~~~~~~~~~~~~~~~~~~~~~~~~~~~~~~~~~~~~~~~~~~~~~~~~

4551 TGTCTTCCCA GCCCACCATC CCCATCGTGG GCATCATTGC TGGCCTGGTT
            ACAGAAGGGT CGGGTGGTAG GGGTAGCACC CGTAGTAACG ACCGGACCAA
            LeuLeuGlyAla ValIleThr GlyAlaVal ValAlaAlaVal MetTrpArg •
            ~~~~~~~~~~~~~~~~~~~~~~~~~~~~~~~~~~~~~~~~~~~~~~~~~~~

4601 CTCCTTGGAG CTGTGATCAC TGGAGCTGTG GTCGCTGCCG TGATGTGGAG
            GAGGAACCTC GACACTAGTG ACCTCGACAC CAGCGACGGC ACTACACCTC
            •ArgLysSer SerAspArgLys GlyGlySer TyrThrGln AlaAlaSerSer •
            ~~~~~~~~~~~~~~~~~~~~~~~~~~~~~~~~~~~~~~~~~~~~~~~~~~~

4651 GAGGAAGAGC TCAGATAGAA AAGGAGGGAG TTACACTCAG GCTGCAAGCA
            CTCCTTCTCG AGTCTATCTT TTCCTCCCTC AATGTGAGTC CGACGTTCGT
            •SAspSerAla GlnGlySer AspValSerLeu ThrAlaCys LysVal***
            ~~~~~~~~~~~~~~~~~~~~~~~~~~~~~~~~~~~~~~~~~~~~~~~~~Stop 4701 GTGACAGTGC CCAGGGCTCT GATGTGTCCC TCACAGCTTG TAAAGTGTGA
            CACTGTCACG GGTCCCGAGA CTACACAGGG AGTGTCGAAC ATTTCACACT 4751 GACAGCTGCC TTGTGTGGGA CTGAGAGGCA AGAGTTGTTC CTGCCCTTCC
            CTGTCGACGG AACACACCCT GACTCTCCGT TCTCAACAAG GACGGGAAGG 4801 CTTTGTGACT TGAAGAACCC TGACTTTGTT TCTGCAAAGG CACCTGCATG
            GAAACACTGA ACTTCTTGGG ACTGAAACAA AGACGTTTCC GTGGACGTAC 4851 TGTCTGTGTT CGTGTAGGCA TAATGTGAGG AGGTGGGGAG AGCACCCCAC
            ACAGACACAA GCACATCCGT ATTACACTCC TCCACCCCTC TCGTGGGGTG 4901 CCCCTGTCCA CCATGACCCT CTTCCCACGC TGACCTGTGC TCCCTCCCCA
            GGGGACAGGT GGTACTGGGA GAAGGGTGCG ACTGGACACG AGGGAGGGGT
              HindIII                  BamHI            SalI
              ~~~~~~                   ~~~~~~           ~~

4951 AAAGCTTGAT ATCCAATTCC TGCAGCCCGG GGGATCCACT TTTTCTAGGT
            TTTCGAACTA TAGGTTAAGG ACGTCGGGCC CCCTAGGTGA AAAAGATCCA
            SalI
            ~~~~

5001 CGACCGATCC TGAGAACTTC AGGGTGAGTT TGGGGACCCT TGATTGTTCT
            GCTGGCTAGG ACTCTTGAAG TCCCACTCAA ACCCCTGGGA ACTAACAAGA

5051 TTCTTTTTCG CTATTGTAAA ATTCATGTTA TATGGAGGGG GCAAAGTTTT
            AAGAAAAAGC GATAACATTT TAAGTACAAT ATACCTCCCC CGTTTCAAAA

5101 CAGGGTGTTG TTTAGAATGG GAAGATGTCC CTTGTATCAC CATGGACCCT
            GTCCCACAAC AAATCTTACC CTTCTACAGG GAACATAGTG GTACCTGGGA

5151 CATGATAATT TTGTTTCTTT CACTTCTAC TCTGTTGACA ACCATTGTCT
            GTACTATTAA AACAAAGAAA GTGAAAGATG AGACAACTGT TGGTAACAGA

5201 CCTCTTATTT TCTTTTCATT TTCTGTAACT TTTTCGTTAA ACTTTAGCTT
            GGAGAATAAA AGAAAAGTAA AAGACATTGA AAAAGCAATT TGAAATCGAA

5251 GCATTTGTAA CGAATTTTTA AATTCACTTT TGTTTATTTG TCAGATTGTA
            CGTAAACATT GCTTAAAAAT TTAAGTGAAA ACAAATAAAC AGTCTAACAT
```

-continued

```
5301  AGTACTTTCT CTAATCACTT TTTTTTCAAG GCAATCAGGG TATATTATAT
      TCATGAAAGA GATTAGTGAA AAAAAAGTTC CGTTAGTCCC ATATAATATA

5351  TGTACTTCAG CACAGTTTTA GAGAACAATT GTTATAATTA AATGATAAGG
      ACATGAAGTC GTGTCAAAAT CTCTTGTTAA CAATATTAAT TTACTATTCC

5401  TAGAATATTT CTGCATATAA ATTCTGGCTG GCGTGGAAAT ATTCTTATTG
      ATCTTATAAA GACGTATATT TAAGACCGAC CGCACCTTTA TAAGAATAAC

5451  GTAGAAACAA CTACACCCTG GTCATCATCC TGCCTTTCTC TTTATGGTTA
      CATCTTTGTT GATGTGGGAC CAGTAGTAGG ACGGAAAGAG AAATACCAAT

5501  CAATGATATA CACTGTTTGA GATGAGGATA AAATACTCTG AGTCCAAACC
      GTTACTATAT GTGACAAACT CTACTCCTAT TTTATGAGAC TCAGGTTTGG

5551  GGGCCCCTCT GCTAACCATG TTCATGCCTT CTTCTCTTTC CTACAGCTCC
      CCCGGGGAGA CGATTGGTAC AAGTACGGAA GAAGAGAAAG GATGTCGAGG

5601  TGGGCAACGT GCTGGTTGTT GTGCTGTCTC ATCATTTTGG CAAAGAATTC
      ACCCGTTGCA CGACCAACAA CACGACAGAG TAGTAAAACC GTTTCTTAAG

5651  CTCGACCAGT GCAGGCTGCC TATCAGAAAG TGGTGGCTGG TGTGGCTAAT
      GAGCTGGTCA CGTCCGACGG ATAGTCTTTC ACCACCGACC ACACCGATTA

5701  GCCCTGGCCC ACAAGTATCA CTAAGCTCGC TTTCTTGCTG TCCAATTTCT
      CGGGACCGGG TGTTCATAGT GATTCGAGCG AAAGAACGAC AGGTTAAAGA

5751  ATTAAAGGTT CCTTTGTTCC CTAAGTCCAA CTACTAAACT GGGGGATATT
      TAATTTCCAA GGAAACAAGG GATTCAGGTT GATGATTTGA CCCCCTATAA

5801  ATGAAGGGCC TTGAGCATCT GGATTCTGCC TAATAAAAAA CATTTATTTT
      TACTTCCCGG AACTCGTAGA CCTAAGACGG ATTATTTTTT GTAAATAAAA

5851  CATTGCAATG ATGTATTTAA ATTATTTCTG AATATTTTAC TAAAAGGGA
      GTAACGTTAC TACATAAATT TAATAAAGAC TTATAAAATG ATTTTTCCCT

5901  ATGTGGGAGG TCAGTGCATT TAAAACATAA AGAAATGAAG AGCTAGTTCA
      TACACCCTCC AGTCACGTAA ATTTTGTATT TCTTTACTTC TCGATCAAGT

5951  AACCTTGGGA AAATACACTA TATCTTAAAC TCCATGAAAG AAGGTGAGGC
      TTGGAACCCT TTTATGTGAT ATAGAATTTG AGGTACTTTC TTCCACTCCG

6001  TGCAAACAGC TAATGCACAT TGGCAACAGC CCCTGATGCC TATGCCTTAT
      ACGTTTGTCG ATTACGTGTA ACCGTTGTCG GGGACTACGG ATACGGAATA

6051  TCATCCCTCA GAAAAGGATT CAAGTAGAGG CTTGATTTGG AGGTTAAAGT
      AGTAGGGAGT CTTTTCCTAA GTTCATCTCC GAACTAAACC TCCAATTTCA

6101  TTTGCTATGC TGTATTTTAC ATTACTTATT GTTTAGCTG TCCTCATGAA
      AAACGATACG ACATAAAATG TAATGAATAA CAAATCGAC AGGAGTACTT

6151  TGTCTTTTCA CTACCCATTT GCTTATCCTG CATCTCTCAG CCTTGACTCC
      ACAGAAAAGT GATGGGTAAA CGAATAGGAC GTAGAGAGTC GGAACTGAGG

6201  ACTCAGTTCT CTTGCTTAGA GATACCACCT TTCCCCTGAA GTGTTCCTTC
      TGAGTCAAGA GAACGAATCT CTATGGTGGA AAGGGGACTT CACAAGGAAG

6251  CATGTTTTAC GGCGAGATGG TTTCTCCTCG CCTGGCCACT CAGCCTTAGT
      GTACAAAATG CCGCTCTACC AAAGAGGAGC GGACCGGTGA GTCGGAATCA

6301  TGTCTCTGTT GTCTTATAGA GGTCTACTTG AAGAAGGAAA AACAGGGGGC
      ACAGAGACAA CAGAATATCT CCAGATGAAC TTCTTCCTTT TTGTCCCCCG

6351  ATGGTTTGAC TGTCCTGTGA GCCCTTCTTC CCTGCCTCCC CCACTCACAG
      TACCAAACTG ACAGGACACT CGGGAAGAAG GGACGGAGGG GGTGAGTGTC

6401  TGACCCGGAA TCTGCAGTGC TAGTCTCCCG GAACTATCAC TCTTTCACAG
      ACTGGGCCTT AGACGTCACG ATCAGAGGGC CTTGATAGTG AGAAAGTGTC

6451  TCTGCTTTGG AAGGACTGGG CTTAGTATGA AAGTTAGGA CTGAGAAGAA
      AGACGAAACC TTCCTGACCC GAATCATACT TTTCAATCCT GACTCTTCTT

6501  TTTGAAAGGG GGCTTTTTGT AGCTTGATAT TCACTACTGT CTTATTACCC
      AAACTTTCCC CCGAAAAACA TCGAACTATA AGTGATGACA GAATAATGGG

6551  TATCATAGGC CCACCCCAAA TGGAAGTCCC ATTCTTCCTC AGGATGTTTA
      ATAGTATCCG GGTGGGGTTT ACCTTCAGGG TAAGAAGGAG TCCTACAAAT

6601  AGATTAGCAT TCAGGAAGAG ATCAGAGGTC TGCTGGCTCC CTTATCATGT
      TCTAATCGTA AGTCCTTCTC TAGTCTCCAG ACGACCGAGG GAATAGTACA
```

```
6651  CCCTTATGGT GCTTCTGGCT CTGCAGTTAT TAGCATAGTG TTACCATCAA
      GGGAATACCA CGAAGACCGA GACGTCAATA ATCGTATCAC AATGGTAGTT

6701  CCACCTTAAC TTCATTTTTC TTATTCAATA CCTAGGTAGG TAGATGCTAG
      GGTGGAATTG AAGTAAAAAG AATAAGTTAT GGATCCATCC ATCTACGATC

6751  ATTCTGGAAA TAAAATATGA GTCTCAAGTG GTCCTTGTCC TCTCTCCCAG
      TAAGACCTTT ATTTTATACT CAGAGTTCAC CAGGAACAGG AGAGAGGGTC

6801  TCAAATTCTG AATCTAGTTG GCAAGATTCT GAAATCAAGG CATATAATCA
      AGTTTAAGAC TTAGATCAAC CGTTCTAAGA CTTTAGTTCC GTATATTAGT

6851  GTAATAAGTG ATGATAGAAG GGTATATAGA AGAATTTTAT TATATGAGAG
      CATTATTCAC TACTATCTTC CCATATATCT TCTTAAAATA ATATACTCTC

6901  GGTGAAATCC CAGCAATTTG GGAGGCTGAG GCAGGAGAAT CGCTTGATCC
      CCACTTTAGG GTCGTTAAAC CCTCCGACTC CGTCCTCTTA GCGAACTAGG

6951  TGGGAGGCAG AGGTTGCAGT GAGCCAAGAT TGTGCCACTG CATTCCAGCC
      ACCCTCCGTC TCCAACGTCA CTCGGTTCTA ACACGGTGAC GTAAGGTCGG

7001  CAGGTGACAG CATGAGACTC CGTCACAAAA AAAAAAGAAA AAAAAGGGGG
      GTCCACTGTC GTACTCTGAG GCAGTGTTTT TTTTTTCTTT TTTTTCCCCC

7051  GGGGGGGCGG TGGAGCCAAG ATGACCGAAT AGGAACAGCT CCAGTACTAT
      CCCCCCCGCC ACCTCGGTTC TACTGGCTTA TCCTTGTCGA GGTCATGATA

7101  AGCTCCCATC GTGAGTGACG CAGAAGACGG GTGATTTCTG CATTTCCAAC
      TCGAGGGTAG CACTCACTGC GTCTTCTGCC CACTAAAGAC GTAAAGGTTG

7151  TGAGGTACCA GGTTCATCTC ACAGGGAAGT GCCAGGCAGT GGGTGCAGGA
      ACTCCATGGT CCAAGTAGAG TGTCCCTTCA CGGTCCGTCA CCCACGTCCT

7201  CAGTAGGTGC AGTGCACTGT GCATGAGCCG AAGCAGGGAC GAGGCATCAC
      GTCATCCACG TCACGTGACA CGTACTCGGC TTCGTCCCTG CTCCGTAGTG

7251  CTCACCCGGG AAGCACAAGG GGTCAGGGAA TTCCCTTTCC TAGTCAAAGA
      GAGTGGGCCC TTCGTGTTCC CCAGTCCCTT AAGGGAAAGG ATCAGTTTCT

7301  AAAGGGTGAC AGATGGCACC TGGAAAATCG GGTCACTCCC GCCCTAATAC
      TTTCCCACTG TCTACCGTGG ACCTTTTAGC CCAGTGAGGG CGGGATTATG
                           HindIII
                           ~~~~~~~
7351  TGCGCTCTTC CAACAAGCTT GTCTTTGGAA AATAGATCAA TTTCCCTTGG
      ACGCGAGAAG GTTGTTCGAA CAGAAACCTT TTATCTAGTT AAAGGGAACC 7401  GAAGAAGATT TTTAGCACAG CAAGGGGCAG GATGTTCAAC TGTGAGAAAA
      CTTCTTCTAA AAATCGTGTC GTTCCCCGTC CTACAAGTTG ACACTCTTTT 7451  CGAAGAATTA GCCAAAAAAC TTCCAGTAAG CCTGCAAAAA AAAAAAAAAA
      GCTTCTTAAT CGGTTTTTTG AAGGTCATTC GGACGTTTTT TTTTTTTTTT 7501  ATAAAAGCTA AGTTTCTATA AATGTTCTGT AAATGTAAAA CAGAAGGTAA
      TATTTTCGAT TCAAAGATAT TTACAAGACA TTTACATTTT GTCTTCCATT 7551  GTCAACTGCA CCTAATAAAA ATCACTTAAT AGCAATGTGC TGTGTCAGTT
      CAGTTGACGT GGATTATTTT TAGTGAATTA TCGTTACACG ACACAGTCAA 7601  GTTTATTGGA ACCACACCCG GTACACATCC TGTCCAGCAT TTGCAGTGCG
      CAAATAACCT TGGTGTGGGC CATGTGTAGG ACAGGTCGTA AACGTCACGC 7651  TGCATTGAAT TATTGTGCTG GCTAGACTTC ATGGCGCCTG GCACCGAATC
      ACGTAACTTA ATAACACGAC CGATCTGAAG TACCGCGGAC CGTGGCTTAG 7701  CTGCCTTCTC AGCGAAAATG AATAATTGCT TTGTTGGCAA GAAACTAAGC
      GACGGAAGAG TCGCTTTTAC TTATTAACGA AACAACCGTT CTTTGATTCG 7751  ATCAATGGGA CGCGTGCAAA GCACCGGCGG CGGTAGATGC GGGGTAAGTA
      TAGTTACCCT GCGCACGTTT CGTGGCCGCC GCCATCTACG CCCCATTCAT 7801  CTGAATTTTA ATTCGACCTA TCCCGGTAAA GCGAAAGCGA CACGCTTTTT
      GACTTAAAAT TAAGCTGGAT AGGGCCATTT CGCTTTCGCT GTGCGAAAAA 7851  TTTCACACAT AGCGGGACCG AACACGTTAT AAGTATCGAT TAGGTCTATT
      AAAGTGTGTA TCGCCCTGGC TTGTGCAATA TTCATAGCTA ATCCAGATAA 7901  TTTGTCTCTC TGTCGGAACC AGAACTGGTA AAAGTTTCCA TTGCGTCTGG
      AAACAGAGAG ACAGCCTTGG TCTTGACCAT TTTCAAAGGT AACGCAGACC
```

-continued
```
7951 GCTTGTCTAT CATTGCGTCT CTATGGTTTT TGGAGGATTA GACGGGGCCA
     CGAACAGATA GTAACGCAGA GATACCAAAA ACCTCCTAAT CTGCCCCGGT 8001 CCAGTAATGG TGCATAGCGG ATGTCTGTAC CGCCATCGGT GCACCGATAT
     GGTCATTACC ACGTATCGCC TACAGACATG GCGGTAGCCA CGTGGCTATA 8051 AGGTTTGGGG CTCCCCAAGG GACTGCTGGG ATGACAGCTT CATATTATAT
     TCCAAACCCC GAGGGGTTCC CTGACGACCC TACTGTCGAA GTATAATATA 8101 TGAATGGGCG CATAATCAGC TTAATTGGTG AGGACAAGCT ACAAGTTGTA
     ACTTACCCGC GTATTAGTCG AATTAACCAC TCCTGTTCGA TGTTCAACAT 8151 ACCTGATCTC CACAAAGTAC GTTGCCGGTC GGGGTCAAAC CGTCTTCGGT
     TGGACTAGAG GTGTTTCATG CAACGGCCAG CCCCAGTTTG GCAGAAGCCA 8201 GCTCGAAACC GCCTTAAACT ACAGACAGGT CCCAGCCAAG TAGGCGGATC
     CGAGCTTTGG CGGAATTTGA TGTCTGTCCA GGGTCGGTTC ATCCGCCTAG 8251 AAAACCTCAA AAGGCGGGA GCCAATCAAA ATGCAGCATT ATATTTTAAG
     TTTTGGAGTT TTTCCGCCCT CGGTTAGTTT TACGTCGTAA TATAAAATTC 8301 CTCACCGAAA CCGGTAAGTA AAGACTATGT ATTTTTTCCC AGTGAATAAT
     GAGTGGCTTT GGCCATTCAT TTCTGATACA TAAAAAGGG TCACTTATTA
       Start E1 SEQ ID NO: 4    MetAlaAsn AspLysGly SerAsnTrp
                               ~~~~~~~~~~~~~~~~~~~~~~~~~~~~~

8351 TGTTGTTAAC TATAAAAAGC GTCATGGCAA ACGATAAAGG TAGCAATTGG
     ACAACAATTG ATATTTTTCG CAGTACCGTT TGCTATTTCC ATCGTTAACC
     AspSerGlyLeu GlyCysSer TyrLeuLeu ThrGluAlaGlu CysGluSer •
     ~~~~~~~~~~~~~~~~~~~~~~~~~~~~~~~~~~~~~~~~~~~~~~~~~~~~~~~

8401 GATTCGGGCT TGGGATGCTC ATATCTGCTG ACTGAGGCAG AATGTGAAAG
     CTAAGCCCGA ACCCTACGAG TATAGACGAC TGACTCCGTC TTACACTTTC
     •AspLysGlu AsnGluGluPro GlyAlaGly ValGluLeu SerValGluSer •
     ~~~~~~~~~~~~~~~~~~~~~~~~~~~~~~~~~~~~~~~~~~~~~~~~~~~~~~~~

8451 TGACAAAGAG AATGAGGAAC CCGGGGCAGG TGTAGAACTG TCTGTGGAAT
     ACTGTTTCTC TTACTCCTTG GGCCCCGTCC ACATCTTGAC AGACACCTTA
     •SAspArgTyr AspSerGln AspGluAspPhe ValAspAsn AlaSerVal
     ~~~~~~~~~~~~~~~~~~~~~~~~~~~~~~~~~~~~~~~~~~~~~~~~~~~~~

8501 CTGATCGGTA TGATAGCCAG GATGAGGATT TTGTTGACAA TGCATCAGTC
     GACTAGCCAT ACTATCGGTC CTACTCCTAA AACAACTGTT ACGTAGTCAG
     PheGlnGlyAsn HisLeuGlu ValPheGln AlaLeuGluLys LysAlaGly •
     ~~~~~~~~~~~~~~~~~~~~~~~~~~~~~~~~~~~~~~~~~~~~~~~~~~~~~~~

8551 TTTCAGGGAA ATCACCTGGA GGTCTTCCAG GCATTAGAGA AAAAGGCGGG
     AAAGTCCCTT TAGTGGACCT CCAGAAGGTC CGTAATCTCT TTTTCCGCCC
     •GluGluGln IleLeuAsnLeu LysArgLys ValLeuGly SerSerGlnAsn •
     ~~~~~~~~~~~~~~~~~~~~~~~~~~~~~~~~~~~~~~~~~~~~~~~~~~~~~~~~~

8601 TGAGGAGCAG ATTTTAAATT TGAAAAGAAA AGTATTGGGG AGTTCGCAAA
     ACTCCTCGTC TAAAATTTAA ACTTTTCTTT TCATAACCCC TCAAGCGTTT
     •ASerSerGly SerGluAla SerGluThrPro ValLysArg ArgLysSer
     ~~~~~~~~~~~~~~~~~~~~~~~~~~~~~~~~~~~~~~~~~~~~~~~~~~~~

8651 ACAGCAGCGG TTCCGAAGCA TCTGAAACTC CAGTTAAAAG ACGGAAATCA
     TGTCGTCGCC AAGGCTTCGT AGACTTTGAG GTCAATTTTC TGCCTTTAGT
     GlyAlaLysArg ArgLeuPhe AlaGluAsn GluAlaAsnArg ValLeuThr •
     ~~~~~~~~~~~~~~~~~~~~~~~~~~~~~~~~~~~~~~~~~~~~~~~~~~~~~~~

8701 GGAGCAAAGC GAAGATTATT GCTGAAAAT GAAGCTAACC GTGTTCTTAC
     CCTCGTTTCG CTTCTAATAA CGACTTTTA CTTCGATTGG CACAAGAATG
     •ProLeuGln ValGlnGlyGlu GlyGluGly ArgGlnGlu LeuAsnGluGlu •
     ~~~~~~~~~~~~~~~~~~~~~~~~~~~~~~~~~~~~~~~~~~~~~~~~~~~~~~~~

8751 GCCCCTCCAG GTACAGGGGG AGGGGGAGGG GAGGCAAGAA CTTAATGAGG
     CGGGGAGGTC CATGTCCCCC TCCCCCTCCC CTCCGTTCTT GAATTACTCC
     •GGlnAlaIle SerHisLeu HisLeuGlnLeu ValLysSer LysAsnAla
     ~~~~~~~~~~~~~~~~~~~~~~~~~~~~~~~~~~~~~~~~~~~~~~~~~~~~~

8801 AGCAGGCAAT TAGTCATCTA CATCTGCAGC TTGTTAAATC TAAAAATGCT
     TCGTCCGTTA ATCAGTAGAT GTAGACGTCG AACAATTTAG ATTTTTACGA
     ThrValPheLys LeuGlyLeu PheLysSer LeuPheLeuCys SerPheHis •
     ~~~~~~~~~~~~~~~~~~~~~~~~~~~~~~~~~~~~~~~~~~~~~~~~~~~~~~~

8851 ACAGTTTTTA AGCTGGGGCT CTTTAAATCT TGTTCCTTT GTAGCTTCCA
     TGTCAAAAAT TCGACCCCGA GAAATTTAGA AACAAGGAAA CATCGAAGGT
     •AspIleThr ArgLeuPheLys AsnAspLys ThrThrAsn GlnGlnTrpVal •
     ~~~~~~~~~~~~~~~~~~~~~~~~~~~~~~~~~~~~~~~~~~~~~~~~~~~~~~~~
```

-continued

```
8901 TGATATTACG AGGTTGTTTA AGAATGATAA GACCACTAAT CAGCAATGGG
     ACTATAATGC TCCAACAAAT TCTTACTATT CTGGTGATTA GTCGTTACCC
     •VLeuAlaVal PheGlyLeu AlaGluValPhe PheGluAla SerPheGlu

8951 TGCTGGCTGT GTTTGGCCTT GCAGAGGTGT TTTTTGAGGC GAGTTTCGAA
     ACGACCGACA CAAACCGGAA CGTCTCCACA AAAAACTCCG CTCAAAGCTT
     LeuLeuLysLys GlnCysSer PheLeuGln MetGlnLysArg SerHisGlu •

9001 CTCCTAAAGA AGCAGTGTAG TTTTCTGCAG ATGCAAAAAA GATCTCATGA
     GAGGATTTCT TCGTCACATC AAAAGACGTC TACGTTTTTT CTAGAGTACT
     •GlyGlyThr CysAlaValTyr LeuIleCys PheAsnThr AlaLysSerArg •

9051 AGGAGGAACT TGTGCAGTTT ACTTAATCTG CTTTAACACA GCTAAAAGCA
     TCCTCCTTGA ACACGTCAAA TGAATTAGAC GAAATTGTGT CGATTTTCGT
     •AGluThrVal ArgAsnLeu MetAlaAsnMet LeuAsnVal ArgGluGlu

9101 GAGAAACAGT CCGGAATCTG ATGGCAAACA TGCTAAATGT AAGAGAAGAG
     CTCTTTGTCA GGCCTTAGAC TACCGTTTGT ACGATTTACA TTCTCTTCTC
     CysLeuMetLeu GlnProPro LysIleArg GlyLeuSerAla AlaLeuPhe •

9151 TGTTTGATGC TGCAGCCACC TAAAATTCGA GGACTCAGCG CAGCTCTATT
     ACAAACTACG ACGTCGGTGG ATTTTAAGCT CCTGAGTCGC GTCGAGATAA
     •TrpPheLys SerSerLeuSer ProAlaThr LeuLysHis GlyAlaLeuPro •

9201 CTGGTTTAAA AGTAGTTTGT CACCCGCTAC ACTTAAACAT GGTGCTTTAC
     GACCAAATTT TCATCAAACA GTGGGCGATG TGAATTTGTA CCACGAAATG
     •PGluTrpIle ArgAlaGln ThrThrLeuAsn GluSerLeu GlnThrGlu

9251 CTGAGTGGAT ACGGGCGCAA ACTACTCTGA ACGAGAGCTT GCAGACCGAG
     GACTCACCTA TGCCCGCGTT TGATGAGACT TGCTCTCGAA CGTCTGGCTC
     LysPheAspPhe GlyThrMet ValGlnTrp AlaTyrAspHis LysTyrAla •

9301 AAATTCGACT TCGGAACTAT GGTGCAATGG GCCTATGATC ACAAATATGC
     TTTAAGCTGA AGCCTTGATA CCACGTTACC CGGATACTAG TGTTTATACG
     •GluGluSer LysIleAlaTyr GluTyrAla LeuAlaAla GlySerAspSer •

9351 TGAGGAGTCT AAAATAGCCT ATGAATATGC TTTGGCTGCA GGATCTGATA
     ACTCCTCAGA TTTTATCGGA TACTTATACG AAACCGACGT CCTAGACTAT
     •SAsnAlaArg AlaPheLeu AlaThrAsnSer GlnAlaLys HisValLys

9401 GCAATGCACG GGCTTTTTTA GCAACTAACA GCCAAGCTAA GCATGTGAAG
     CGTTACGTGC CCGAAAAAAT CGTTGATTGT CGGTTCGATT CGTACACTTC
     AspCysAlaThr MetValArg HisTyrLeu ArgAlaGluThr GlnAlaLeu •

9451 GACTGTGCAA CTATGGTAAG ACACTATCTA AGAGCTGAAA CACAAGCATT
     CTGACACGTT GATACCATTC TGTGATAGAT TCTCGACTTT GTGTTCGTAA
     •SerMetPro AlaTyrIleLys AlaArgCys LysLeuAla ThrGlyGluGly •

9501 AAGCATGCCT GCATATATTA AAGCTAGGTG CAAGCTGGCA ACTGGGGAAG
     TTCGTACGGA CGTATATAAT TTCGATCCAC GTTCGACCGT TGACCCCTTC
     •GSerTrpLys SerIleLeu ThrPhePheAsn TyrGlnAsn IleGluLeu

9551 GAAGCTGGAA GTCTATCCTA ACTTTTTTA ACTATCAGAA TATTGAATTA
     CTTCGACCTT CAGATAGGAT TGAAAAAAAT TGATAGTCTT ATAACTTAAT
     IleThrPheIle AsnAlaLeu LysLeuTrp LeuLysGlyIle ProLysLys •

9601 ATTACCTTTA TTAATGCTTT AAAGCTCTGG CTAAAAGGAA TTCCAAAAAA
     TAATGGAAAT AATTACGAAA TTTCGAGACC GATTTTCCTT AAGGTTTTTT
     •AsnCysLeu AlaPheIleGly ProProAsn ThrGlyLys SerMetLeuCys •

9651 AAACTGTTTA GCATTTATTG GCCCTCCAAA CACAGGCAAG TCTATGCTCT
     TTTGACAAAT CGTAAATAAC CGGGAGGTTT GTGTCCGTTC AGATACGAGA
     •CAsnSerLeu IleHisPhe LeuGlyGlySer ValLeuSer PheAlaAsn

9701 GCAACTCATT AATTCATTTT TTGGGTGGTA GTGTTTTATC TTTTGCCAAC
```

-continued

```
       CGTTGAGTAA TTAAGTAAAA AACCCACCAT CACAAAATAG AAAACGGTTG
       HisLysSerHis PheTrpLeu AlaSerLeu AlaAspThrArg AlaAlaLeu •
       ~~~~~~~~~~~~~~~~~~~~~~~~~~~~~~~~~~~~~~~~~~~~~~~~

9751  CATAAAAGTC ACTTTTGGCT TGCTTCCCTA GCAGATACTA GAGCTGCTTT
       GTATTTTCAG TGAAACCGA ACGAAGGGAT CGTCTATGAT CTCGACGAAA
       •ValAspAsp AlaThrHisAla CysTrpArg TyrPheAsp ThrTyrLeuArg •
       ~~~~~~~~~~~~~~~~~~~~~~~~~~~~~~~~~~~~~~~~~~~~~~~~

9801  AGTAGATGAT GCTACTCATG CTTGCTGGAG GTACTTTGAC ACATACCTCA
       TCATCTACTA CGATGAGTAC GAACGACCTC CATGAAACTG TGTATGGAGT
       •AAsnAlaLeu AspGlyTyr ProValSerIle AspArgLys HisLysAla
       ~~~~~~~~~~~~~~~~~~~~~~~~~~~~~~~~~~~~~~~~~~~~~~~~

9851  GAAATGCATT GGATGGCTAC CCTGTCAGTA TTGATAGAAA ACACAAAGCA
       CTTTACGTAA CCTACCGATG GGACAGTCAT AACTATCTTT TGTGTTTCGT
       AlaValGlnIle LysAlaPro ProLeuLeu ValThrSerAsn IleAspVal •
       ~~~~~~~~~~~~~~~~~~~~~~~~~~~~~~~~~~~~~~~~~~~~~~~~

9901  GCGGTTCAAA TTAAAGCTCC ACCCCTCCTG GTAACCAGTA ATATTGATGT
       CGCCAAGTTT AATTTCGAGG TGGGGAGGAC CATTGGTCAT TATAACTACA
       •GlnAlaGlu AspArgTyrLeu TyrLeuHis SerArgVal GlnThrPheArg •
       ~~~~~~~~~~~~~~~~~~~~~~~~~~~~~~~~~~~~~~~~~~~~~~~~

9951  GCAGGCAGAG GACAGATATT TGTACTTGCA TAGTCGGGTG CAAACCTTTC
       CGTCCGTCTC CTGTCTATAA ACATGAACGT ATCAGCCCAC GTTTGGAAAG
       •APheGluGln ProCysThr AspGluSerGly GluGlnPro PheAsnIle
       ~~~~~~~~~~~~~~~~~~~~~~~~~~~~~~~~~~~~~~~~~~~~~~~~

10001  GCTTTGAGCA GCCATGCACA GATGAATCGG GTGAGCAACC TTTTAATATT
       CGAAACTCGT CGGTACGTGT CTACTTAGCC CACTCGTTGG AAAATTATAA
       ThrAspAlaAsp TrpLysSer PhePheVal ArgLeuTrpGly ArgLeuAsp •
       ~~~~~~~~~~~~~~~~~~~~~~~~~~~~~~~~~~~~~~~~~~~~~~~~

10051  ACTGATGCAG ATTGGAAATC TTTTTTTGTA AGGTTATGGG GGCGTTTAGA
       TGACTACGTC TAACCTTTAG AAAAAAACAT TCCAATACCC CCGCAAATCT
                       SEQ ID NO: 5 Start E2 MetGluThr AlaCysGlu
                                     ~~~~~~~~~~~~~~~~~~~~
       •LeuIleAsp GluGluGluAsp SerGluGlu AspGlyAsp SerMetArgThr •
       ~~~~~~~~~~~~~~~~~~~~~~~~~~~~~~~~~~~~~~~~~~~~~~~~

10101  CCTGATTGAC GAGGAGGAGG ATAGTGAAGA GGATGGAGAC AGCATGCGAA
       GGACTAACTG CTCCTCCTCC TATCACTTCT CCTACCTCTG TCGTACGCTT
       ArgLeuHisAla AlaGlnGlu ThrGlnMet GlnLeuIleGlu LysSerSer •
       ~~~~~~~~~~~~~~~~~~~~~~~~~~~~~~~~~~~~~~~~~~~~~~~~
       •TPheThrCys SerAlaArg AsnThrAsnAla ValAsp Stop E1
       ~~~~~~~~~~~~~~~~~~~~~~~~~~~~~~~~~~~~~~~~~

10151  CGTTTACATG CAGCGCAAGA AACACAAATG CAGTTGATTG AGAAAAGTAG
       GCAAATGTAC GTCGCGTTCT TTGTGTTTAC GTCAACTAAC TCTTTTCATC
       •AspLysLeu GlnAspHisIle LeuTyrTrp ThrAlaVal ArgThrGluAsn •
       ~~~~~~~~~~~~~~~~~~~~~~~~~~~~~~~~~~~~~~~~~~~~~~~~

10201  TGATAAGTTG CAAGATCATA TACTGTACTG GACTGCTGTT AGAACTGAGA
       ACTATTCAAC GTTCTAGTAT ATGACATGAC CTGACGACAA TCTTGACTCT
       •AThrLeuLeu TyrAlaAla ArgLysLysGly ValThrVal LeuGlyHis
       ~~~~~~~~~~~~~~~~~~~~~~~~~~~~~~~~~~~~~~~~~~~~~~~~

10251  ACACACTGCT TTATGCTGCA AGGAAAAAAG GGGTGACTGT CCTAGGACAC
       TGTGTGACGA AATACGACGT TCCTTTTTTC CCCACTGACA GGATCCTGTG
       CysArgValPro HisSerVal ValCysGln GluArgAlaLys GlnAlaIle •
       ~~~~~~~~~~~~~~~~~~~~~~~~~~~~~~~~~~~~~~~~~~~~~~~~

10301  TGCAGAGTAC CACACTCTGT AGTTTGTCAA GAGAGAGCCA AGCAGGCCAT
       ACGTCTCATG GTGTGAGACA TCAAACAGTT CTCTCTCGGT TCGTCCGGTA
       •GluMetGln LeuSerLeuGln GluLeuSer LysThrGlu PheGlyAspGlu •
       ~~~~~~~~~~~~~~~~~~~~~~~~~~~~~~~~~~~~~~~~~~~~~~~~

10351  TGAAATGCAG TTGTCTTTGC AGGAGTTAAG CAAAACTGAG TTTGGGGATG
       ACTTTACGTC AACAGAAACG TCCTCAATTC GTTTTGACTC AAACCCCTAC
       •GProTrpSer LeuLeuAsp ThrSerTrpAsp ArgTyrMet SerGluPro
       ~~~~~~~~~~~~~~~~~~~~~~~~~~~~~~~~~~~~~~~~~~~~~~~~

10401  AACCATGGTC TTTGCTTGAC ACAAGCTGGG ACCGATATAT GTCAGAACCT
       TTGGTACCAG AAACGAACTG TGTTCGACCC TGGCTATATA CAGTCTTGGA
       LysArgCysPhe LysLysGly AlaArgVal ValGluValGlu PheAspGly •
       ~~~~~~~~~~~~~~~~~~~~~~~~~~~~~~~~~~~~~~~~~~~~~~~~

10451  AAACGGTGCT TTAAGAAAGG CGCCAGGGTG GTAGAGGTGG AGTTTGATGG
       TTTGCCACGA AATTCTTTCC GCGGTCCCAC CATCTCCACC TCA7ACTACC
       •AsnAlaSer AsnThrAsnTrp TyrThrVal TyrSerAsn LeuTyrMetArg •
```

-continued

```
10501 AAATGCAAGC AATACAAACT GGTACACTGT CTACAGCAAT TTGTACATGC
      TTTACGTTCG TTATGTTTGA CCATGTGACA GATGTCGTTA AACATGTACG
      •AThrGluAsp GlyTrpGln LeuAlaLysAla GlyLeuThr GluLeuGly

10551 GCACAGAGGA CGGCTGGCAG CTTGCGAAGG CTGGGCTGAC GGAACTGGGC
      CGTGTCTCCT GCCGACCGTC GAACGCTTCC GACCCGACTG CCTTGACCCG
      SerThrThrAla ProTrpPro ValLeuAsp AlaPheThrIle LeuAlaLeu •

10601 TCTACTACTG CACCATGGCC GGTGCTGGAC GCATTTACTA TTCTCGCTTT
      AGATGATGAC GTGGTACCGG CCACGACCTG CGTAAATGAT AAGAGCGAAA
      •ValThrArg GlnProAspLeu ValGlnGln GlyIleThr Leu Stop E2

10651 GGTGACGAGG CAGCCAGATT TAGTACAACA GGGCATTACT CTGTAAGAGA
      CCACTGCTCC GTCGGTCTAA ATCATGTTGT CCCGTAATGA GACATTCTCT

10701 TCAGGACAGA GTGTATGCTG GTGTCTCATC CACCTCTTCT GATTTTAGAG
      AGTCCTGTCT CACATACGAC CACAGAGTAG GTGGAGAAGA CTAAAATCTC

10751 ATCGCCCAGA CGGAGTCTGG GTCGCATCCG AAGGACCTGA AGGAGACCCT
      TAGCGGGTCT GCCTCAGACC CAGCGTAGGC TTCCTGGACT TCCTCTGGGA

10801 GCAGGAAAAG AAGCCGACGC AGCCCAGCCT GTCTCTTCTT TGCTCGGCTC
      CGTCCTTTTC TTCGGCTCGG TCGGGTCGGA CAGAGAAGAA ACGAGCCGAG

10851 CCCCGCCTGC GGTCCCATCA GAGCAGGCCT CGGTTGGGTA CGGGACGGTC
      GGGGCGGACG CCAGGGTAGT CTCGTCCGGA GCCAACCCAT GCCCTGCCAG

10901 CTCGCTCGCA CCCCTACAAT TTTCCTGCAG GCTCGGGGGG CTCTATTCTC
      GAGCGAGCGT GGGGATGTTA AAAGGACGTC CGAGCCCCCC GAGATAAGAG

10951 CGCTCTTCCT CCACCCCGTG CAGGGCACGG TACCGGTGGA CTTGGCATCA
      GCGAGAAGGA GGTGGGGCAC GTCCCGTGCC ATGGCCACCT GAACCGTAGT

11001 AGGCAGGAAG AAGAGGAGCA GTCGCCCGAC TCCACAGAGG AAGAACCAGT
      TCCGTCCTTC TTCTCCTCGT CAGCGGGCTG AGGTGTCTCC TTCTTGGTCA

11051 GACTCTCCCA AGGCGCACCA CCAATGATGG ATTCCACCTG TTAAAGGCAG
      CTGAGAGGGT TCCGCGTGGT GGTTACTACC TAAGGTGGAC AATTTCCGTC

11101 GAGGGTCATG CTTTGCTCTA ATTTCAGGAA CTGCTAACCA GGTAAAGTGC
      CTCCCAGTAC GAAACGAGAT TAAAGTCCTT GACGATTGGT CCATTTCACG

11151 TATCGCTTTC GGGTGAAAAA GAACCATAGA CATCGCTACG AGAAGTAGAC
      ATAGCGAAAG CCCACTTTTT CTTGGTATCT GTAGCGATGC TCTTGACGTG

11201 CACCACCTGG TTCACAGTTG CTGACAACGG TGCTGAAAGA CAAGGACAAG
      GTGGTGGACC AAGTGTCAAC GACTGTTGCC ACGACTTTCT GTTCCTGTTC

11251 CACAAATACT GATCACCTTT GGATCGCCAA GTCAAAGGCA AGACTTTCTG
      GTGTTTATGA CTAGTGGAAA CCTAGCGGTT CAGTTTCCGT TCTGAAAGAC

11301 AAACATGTAC CACTACCTCC TGGAATGAAC ATTTCCGGCT TTACAGCCAG
      TTTGTACATG GTGATGGAGG ACCTTACTTG TAAAGGCCGA AATGTCGGTC

11351 CTTGGACTTC TGATCACTGC CATTGCCTTT TCTTCATCTG ACTGGTGTAC
      GAACCTGAAG ACTAGTGACG GTAACGGAAA AGAAGTAGAC TGACCACATG

11401 TATGCCAAAT CTATGCGACC GCATTATAAA GCCGAATTCT GCAGATATCC
      ATACGGTTTA GATACGCTGG CGTAATATTT CGGCTTAAGA CGTCTATAGG

11451 ATCACACTGG CGGCCATATG GCCGCTATGC GGTGTGAAAT ACCGCACAGA
      TAGTGTGACC GCCGGTATAC CGGCGATACG CCACACTTTA TGGCGTGTCT

11501 TGCGTAAGGA GAAAATACCG CATCAGGCGC TCTTCCGCTT CCTCGCTCAC
      ACGCATTCCT CTTTTATGGC GTAGTCCGCG AGAAGGCGAA GGAGCGAGTG

11551 TGACTCGCTG CGCTCGGTCG TTCGGCTGCG GCGAGCGGTA TCAGCTCACT
      ACTGAGCGAC GCGAGCCAGC AAGCCGACGC CGCTCGCCAT AGTCGAGTGA

11601 CAAAGGCGGT AATACGGTTA TCCACAGAAT CAGGGGATAA CGCAGGAAAG
      GTTTCCGCCA TTATGCCAAT AGGTGTCTTA GTCCCCTATT GCGTCCTTTC

11651 AACATGTGAG CAAAAGGCCA GCAAAAGGCC AGGAACCGTA AAAAGGCCGC
      TTGTACACTC GTTTTCCGGT CGTTTTCCGG TCCTTGGCAT TTTTCCGGCG

11701 GTTGCTGGCG TTTTTCCATA GGCTCCGCCC CCCTGACGAG CATCACAAAA
```

```
                -continued
        CAACGACCGC AAAAAGGTAT CCGAGGCGGG GGGACTGCTC GTAGTGTTTT 11751   ATCGACGCTC AAGTCAGAGG TGGCGAAACC CGACAGGACT ATAAAGATAC
        TAGCTGCGAG TTCAGTCTCC ACCGCTTTGG GCTGTCCTGA TATTTCTATG 11801   CAGGCGTTTC CCCCTGGAAG CTCCCTCGTG CGCTCTCCTG TTCCGACCCT
        GTCCGCAAAG GGGGACCTTC GAGGGAGCAC GCGAGAGGAC AAGGCTGGGA 11851   GCCGCTTACC GGATACCTGT CCGCCTTTCT CCCTTCGGGA AGCGTGGCGC
        CGGCGAATGG CCTATGGACA GGCGGAAAGA GGGAAGCCCT TCGCACCGCG 11901   TTTCTCATAG CTCACGCTGT AGGTATCTCA GTTCGGTGTA GGTCGTTCGC
        AAAGAGTATC GAGTGCGACA TCCATAGAGT CAAGCCACAT CCAGCAAGCG 11951   TCCAAGCTGG GCTGTGTGCA CGAACCCCCC GTTCAGCCCG ACCGCTGCGC
        AGGTTCGACC CGACACACGT GCTTGGGGGG CAAGTCGGGC TGGCGACGCG 12001   CTTATCCGGT AACTATCGTC TTGAGTCCAA CCCGGTAAGA CACGACTTAT
        GAATAGGCCA TTGATAGCAG AACTCAGGTT GGGCCATTCT GTGCTGAATA 12051   CGCCACTGGC AGCAGCCACT GGTAACAGGA TTAGCAGAGC GAGGTATGTA
        GCGGTGACCG TCGTCGGTGA CCATTGTCCT AATCGTCTCG CTCCATACAT 12101   GGCGGTGCTA CAGAGTTCTT GAAGTGGTGG CCTAACTACG GCTACACTAG
        CCGCCACGAT GTCTCAAGAA CTTCACCACC GGATTGATGC CGATGTGATC 12151   AAGGACAGTA TTTGGTATCT GCGCTCTGCT GAAGCCAGTT ACCTTCGGAA
        TTCCTGTCAT AAACCATAGA CGCGAGACGA CTTCGGTCAA TGGAAGCCTT 12201   AAAGAGTTGG TAGCTCTTGA TCCGGCAAAC AAACCACCGC TGGTAGCGGT
        TTTCTCAACC ATCGAGAACT AGGCCGTTTG TTTGGTGGCG ACCATCGCCA 12251   GGTTTTTTTG TTTGCAAGCA GCAGATTACG CGCAGAAAAA AAGGATCTCA
        CCAAAAAAAC AAACGTTCGT CGTCTAATGC GCGTCTTTTT TTCCTAGAGT 12301   AGAAGATCCT TTGATCTTTT CTACGGGGTC TGACGCTCAG TGGAACGAAA
        TCTTCTAGGA AACTAGAAAA GATGCCCCAG ACTGCGAGTC ACCTTGCTTT 12351   ACTCACGTTA AGGGATTTTG GTCATGAGAT TATCAAAAAG GATCTTCACC
        TGAGTGCAAT TCCCTAAAAC CAGTACTCTA ATAGTTTTTC CTAGAAGTGG 12401   TAGATCCTTT TAAATTAAAA ATGAAGTTTT AAATCAATCT AAAGTATATA
        ATCTAGGAAA ATTTAATTTT TACTTCAAAA TTTAGTTAGA TTTCATATAT 12451   TGAGTAAACT TGGTCTGACA GTTACCAATG CTTAATCAGT GAGGCACCTA
        ACTCATTTGA ACCAGACTGT CAATGGTTAC GAATTAGTCA CTCCGTGGAT
             Stop SEQ ID NO: 6  TrpHis LysIleLeuSer AlaGlyIle •
                  ***~~~~~~~~~~~~~~~~~~~~~~~~~~~

12501   TCTCAGCGAT CTGTCTATTT CGTTCATCCA TAGTTGCCTG ACTCCCCGTC
        AGAGTCGCTA GACAGATAAA GCAAGTAGGT ATCAACGGAC TGAGGGGCAG
        .GluAlaIle GlnArgAsnArg GluAspMet ThrAlaGln SerGlyThrThr •
        ~~~~~~~~~~~~~~~~~~~~~~~~~~~~~~~~~~~~~~~~~~~~~~~~~~~~

12551   GTGTAGATAA CTACGATACG GGAGGGCTTA CCATCTGGCC CCAGTGCTGC
        CACATCTATT GATGCTATGC CCTCCCGAAT GGTAGACCGG GGTCACGACG
        ..TyrIleVal ValIleArg SerProLysGly AspProGly LeuAlaAla
        ~~~~~~~~~~~~~~~~~~~~~~~~~~~~~~~~~~~~~~~~~~~~~~~~~~~

12601   AATGATACCG CGAGACCCAC GCTCACCGGC TCCAGATTTA TCAGCAATAA
        TTACTATGGC GCTCTGGGTG CGAGTGGCCG AGGTCTAAAT AGTCGTTATT
        IleIleGlyArg SerGlyArg GluGlyAla GlySerLysAsp AlaIlePhe •
        ~~~~~~~~~~~~~~~~~~~~~~~~~~~~~~~~~~~~~~~~~~~~~~~~~~~

12651   ACCAGCCAGC CGGAAGGGCC GAGCGCAGAA GTGGTCCTGC AACTTTATCC
        TGGTCGGTCG GCCTTCCCGG CTCGCGTCTT CACCAGGACG TTGAAATAGG
        .TrpGlyAla ProLeuAlaSer ArgLeuLeu ProGlyAla ValLysAspAla •
        ~~~~~~~~~~~~~~~~~~~~~~~~~~~~~~~~~~~~~~~~~~~~~~~~~~~

12701   GCCTCCATCC AGTCTATTAA TTGTTGCCGG GAAGCTAGAG TAAGTAGTTC
        CGGAGGTAGG TCAGATAATT AACAACGGCC CTTCGATCTC ATTCATCAAG
        ..GluMetTrp AspIleLeu GlnGlnArgSer AlaLeuThr LeuLeuGlu
        ~~~~~~~~~~~~~~~~~~~~~~~~~~~~~~~~~~~~~~~~~~~~~~~~~~~

12751   GCCAGTTAAT AGTTTGCGCA ACGTTGTTGC CATTGCTGCA GGCATCGTGG
        CGGTCAATTA TCAAACGCGT TGCAACAACG GTAACGACGT CCGTAGCACC
        GlyThrLeuLeu LysArgLeu ThrThrAla MetAlaAlaPro MetThrThr •
        ~~~~~~~~~~~~~~~~~~~~~~~~~~~~~~~~~~~~~~~~~~~~~~~~~~~

12801   TGTCACGCTC GTCGTTTGGT ATGGCTTCAT TCAGCTCCGG TTCCCAACGA
        ACAGTGCGAG CAGCAAACCA TACCGAAGTA AGTCGAGGCC AAGGGTTGCT
```

-continued
```
             .AspArgGlu AspAsnProIle AlaGluAsn LeuGluPro GluTrpArgAsp •

12851   TCAAGGCGAG TTACATGATC CCCCATGTTG TGCAAAAAAG CGGTTAGCTC
        AGTTCCGCTC AATGTACTAG GGGGTACAAC ACGTTTTTTC GCCAATCGAG
        ..LeuArgThr ValHisAsp GlyMetAsnHis LeuPheAla ThrLeuGlu

12901   CTTCGGTCCT CCGATCGTTG TCAGAAGTAA GTTGGCCGCA GTGTTATCAC
        GAAGCCAGGA GGCTAGCAAC AGTCTTCATT CAACCGGCGT CACAATAGTG
        LysProGlyGly IleThrThr LeuLeuLeu AsnAlaAlaThr AsnAspSer •

12951   TCATGGTTAT GGCAGCACTG CATAATTCTC TTACTGTCAT GCCATCCGTA
        AGTACCAATA CCGTCGTGAC GTATTAAGAG AATGACAGTA CGGTAGGCAT
        .MetThrIle AlaAlaSerCys LeuGluArg ValThrMet GlyAspThrLeu •

13001   AGATGCTTTT CTGTGACTGG TGAGTACTCA ACCAAGTCAT TCGTAGAAAA
        TCTACGAAAA GACACTGACC ACTCATGAGT TGGTTCAGTA AGCTCTTAT
        ..HisLysGlu ThrValPro SerTyrGluVal LeuAspAsn GlnSerTyr

13051   GTGTATGCGG CGACCGAGTT GCTCTTGCCC GGCGTCAACA CGGGATAATA
        CACATACGCC GCTGGCTCAA CGAGAACGGG CCGCAGTTGT GCCCTATTAT
        HisIleArgArg GlyLeuGln GluGlnGly AlaAspValArg SerLeuVal •

13101   CCGCGCCACA TAGCAGAACT TTAAAAGTGC TCATCATTGG AAAACGTTCT
        GGCGCGGTGT ATCGTCTTGA AATTTTCACG AGTAGTAACC TTTTGCAAGA
        .AlaGlyCys LeuLeuValLys PheThrSer MetMetPro PheArgGluGlu •

13151   TCGGGGCGAA AACTCTCAAG GATCTTACCG CTGTTGAGAT CCAGTTCGAT
        AGCCCCGCTT TTGAGAGTTC CTAGAATGGC GACAACTCTA GGTCAAGCTA
        ..ProArgPhe SerGluLeu IleLysGlySer AsnLeuAsp LeuGluIle

13201   GTAACCCACT CGTGCACCCA ACTGATCTTC AGCATCTTTT ACTTTCACCA
        CATTGGGTGA GCACGTGGGT TGACTAGAAG TCGTAGAAAA TGAAAGTGGT
        TyrGlyValArg AlaGlyLeu GlnAspGlu AlaAspLysVal LysValLeu •

13251   GCGTTTCTGG GTGAGCAAAA ACAGGAAGGC AAAATGCCGC AAAAAAGGGA
        CGCAAAGACC CACTCGTTTT TGTCCTTCCG TTTTACGGCG TTTTTTCCCT
        .ThrGluPro HisAlaPheVal ProLeuCys PheAlaAla PhePheProIle •

13301   ATAAGGGCGA CACGGAAATG TTGAATACTC ATACTCTTCC TTTTTCAATA
        TATTCCCGCT GTGCCTTTAC AACTTATGAG TATGAGAAGG AAAAAGTTAT
        .. LeuAlaVal ArgPheHis GlnIleSerMet Start Beta-Lactamase 13351   TTATTGAAGC ATTTATCAGG GTTATTGTCT CATGAGCGGA TACATATTTG
        AATAACTTCG TAAATAGTCC CAATAACAGA GTACTCGCCT ATGTATAAAC 13401   AATGTATTTA GAAAAATAAA CAAATAGGGG TTCCGCGCAC ATTTCCCCGA
        TTACATAAAT CTTTTTATTT GTTTATCCCC AAGGCGCGTG TAAAGGGGCT 13451   AAAGTGCCAC CTGACGTCTA AGAAACCATT ATTATCATGA CATTAACCTA
        TTTCACGGTG GACTGCAGAT TCTTTGGTAA TAATAGTACT GTAATTGGAT 13501   TAAAAATAGG CGTATCACGA GGCCCTTTCG TCTTCAAGAA TTCTCATGTT
        ATTTTTATCC GCATAGTGCT CCGGGAAAGC AGAAGTTCTT AAGAGTACAA
                            HindIII
                            ~~~~~~~

13551   TGACAGCTTA TCATCGATAA GCTTCACGCT GCCGCAAGCA CTCAGGGCGC
        ACTGTCGAAT AGTAGCTATT CGAAGTGCGA CGGCGTTCGT GAGTCCCGCG

13601   AAGGGCTGCT AAAGGAAGCG GAACACGTAG AAAGCCAGTC CGCAGAAACG
        TTCCCGACGA TTTCCTTCGC CTTGTGCATC TTTCGGTCAG GCGTCTTTGC

13651   GTGCTGACCC CGGATGAATG TCAGCTACTG GGCTATCTGG ACAAGGGAAA
        CACGACTGGG GCCTACTTAC AGTCGATGAC CCGATAGACC TGTTCCCTTT

13701   ACGCAAGCGC AAAGAGAAAG CAGGTAGCTT GCAGTGGGCT TACATGGCGA
        TGCGTTCGCG TTTCTCTTTC GTCCATCGAA CGTCACCCGA ATGTACCGCT

13751   TAGCTAGACT GGGCGGTTTT ATGGACAGCA AGCGAACCGG AATTGCCAGC
        ATCGATCTGA CCCGCCAAAA TACCTGTCGT TCGCTTGGCC TTAACGGTCG
```

-continued

```
13801 TGGGGCGCCC TCTGGTAAGG TTGGGAAGCC CTGCAAAGTA AACTGGATGG
      ACCCCGCGGG AGACCATTCC AACCCTTCGG GACGTTTCAT TTGACCTACC

13851 CTTTCTTGCC GCCAAGGATC TGATGGCGCA GGGGATCAAG ATCCTGCTTC
      GAAAGAACGG CGGTTCCTAG ACTACCGCGT CCCCTAGTTC TAGGACGAAG

13901 ATCCCCGTGG CCCGTTGCTC GCGTTTGCTG GCGGTGTCCC CGGAAGAAAT
      TAGGGCACC  GGGCAACGAG CGCAAACGAC CGCCACAGGG GCCTTCTTTA

13951 ATATTTGCAT GTCTTTAGTT CTATGATGAC ACAAACCCCG CCCAGCGTCT
      TATAAACGTA CAGAAATCAA GATACTACTG TGTTTGGGGC GGGTCGCAGA

14001 TGTCATTGGC GAATTCGAAC ACGCAGATGC AGTCGGGGCG GCGCGGTCCC
      ACAGTAACCG CTTAAGCTTG TGCGTCTACG TCAGCCCCGC CGCGCCAGGG

14051 AGGTCCACTT CGCATATTAA GGTGACGCGT GTGGCCTCGA ACACCGAGCG
      TCCAGGTGAA GCGTATAATT CCACTGCGCA CACCGGAGCT TGTGGCTCGC

14101 ACCCTGCAGC GACCCGCTTA ACAGCGTCAA CAGCGTGCCG CAGATCTGAT
      TGGGACGTCG CTGGGCGAAT TGTCGCAGTT GTCGCACGGC GTCTAGACTA
Start G418 resist SEQ ID NO: 7     Met IleGluGlnAsp GlyLeuHis •
                                   ~~~~~~~~~~~~~~~~~~~~~~~~~~~

14151 CAAGAGACAG GATGAGGATC GTTTCGCATG ATTGAACAAG ATGGATTGCA
      GTTCTCTGTC CTACTCCTAG CAAAGCGTAC TAACTTGTTC TACCTAACGT
      •AlaGlySer ProAlaAlaTrp ValGluArg LeuPheGly TyrAspTrpAla •
      ~~~~~~~~~~~~~~~~~~~~~~~~~~~~~~~~~~~~~~~~~~~~~~~~~~~~~

14201 CGCAGGTTCT CCGGCCGCTT GGGTGGAGAG GCTATTCGGC TATGACTGGG
      GCGTCCAAGA GGCCGGCGAA CCCACCTCTC CGATAAGCCG ATACTGACCC
      •AGlnGlnThr IleGlyCys SerAspAlaAla ValPheArg LeuSerAla
      ~~~~~~~~~~~~~~~~~~~~~~~~~~~~~~~~~~~~~~~~~~~~~~~~~~~~

14251 CACAACAGAC AATCGGCTGC TCTGATGCCG CCGTGTTCCG GCTGTCAGCG
      GTGTTGTCTG TTAGCCGACG AGACTACGGC GGCACAAGGC CGACAGTCGC
      GlnGlyArgPro ValLeuPhe ValLysThr AspLeuSerGly AlaLeuAsn •
      ~~~~~~~~~~~~~~~~~~~~~~~~~~~~~~~~~~~~~~~~~~~~~~~~~~~~~

14301 CAGGGGCGCC CGGTTCTTTT TGTCAAGACC GACCTGTCCG GTGCCCTGAA
      GTCCCCGCGG GCCAAGAAAA ACAGTTCTGG CTGGACAGGC CACGGGACTT
      •GluLeuGln AspGluAlaAla ArgLeuSer TrpLeuAla ThrThrGlyVal •
      ~~~~~~~~~~~~~~~~~~~~~~~~~~~~~~~~~~~~~~~~~~~~~~~~~~~~~

14351 TGAACTGCAG GACGAGGCAG CGCGGCTATC GTGGCTGGCC ACGACGGGCG
      ACTTGACGTC CTGCTCCGTC GCGCCGATAG CACCGACCGG TGCTGCCCGC
      •VProCysAla AlaValLeu AspValValThr GluAlaGly ArgAspTrp
      ~~~~~~~~~~~~~~~~~~~~~~~~~~~~~~~~~~~~~~~~~~~~~~~~~~~~

14401 TTCCTTGCGC AGCTGTGCTC GACGTTGTCA CTGAAGCGGG AAGGAACGCG
      AAGGAACGCG TCGACACGAG CTGCAACAGT GACTTCGCCC TTCCCTGACC
      LeuLeuLeuGly GluValPro GlyGlnAsp LeuLeuSerSer HisLeuAla •
      ~~~~~~~~~~~~~~~~~~~~~~~~~~~~~~~~~~~~~~~~~~~~~~~~~~~~~

14451 CTGCTATTGG GCGAAGTGCC GGGGCAGGAT CTCCTGTCAT CTCACCTTGC
      GACGATAACC CGCTTCACGG CCCCGTCCTA GAGGACAGTA GAGTGGAACG
                                                ~~~~~~~~
      •ProAlaGlu LysValSerIle MetAlaAsp AlaMetArg ArgLeuHisThr •
      ~~~~~~~~~~~~~~~~~~~~~~~~~~~~~~~~~~~~~~~~~~~~~~~~~~~~~

14501 TCCTGCCGAG AAAGTATCCA TCATGGCTGA TGCAATGCGG CGGCTGCATA
      AGGACGGCTC TTTCATAGGT AGTACCGACT ACGTTACGCC GCCGACGTAT
      ~~~~~~~~~~~~~~~~~~~~~~~~~~~~~~~~~~~~~~~~~~~~~~~~~~~~
      •TLeuAspPro AlaThrCys ProPheAspHis GlnAlaLys HisArgIle
      ~~~~~~~~~~~~~~~~~~~~~~~~~~~~~~~~~~~~~~~~~~~~~~~~~~~~

14551 CGCTTGATCC GGCTACCTGC CCATTCGACC ACCAAGCGAA ACATCGCATC
      GCGAACTAGG CCGATGGACG GGTAAGCTGG TGGTTCGCTT TGTAGCGTAG
      ~~~~~~~~~~~~~~~~~~~~~~~~~~~~~~~~~~~~~~~~~~~~~~~~~~~~
      GluArgAlaArg ThrArgMet GluAlaGly LeuValAspGln AspAspLeu •
      ~~~~~~~~~~~~~~~~~~~~~~~~~~~~~~~~~~~~~~~~~~~~~~~~~~~~~

14601 GAGCGAGCAC GTACTCGGAT GGAAGCCGGT CTTGTCGATC AGGATGATCT
      CTCGCTCGTG CATGAGCCTA CCTTCGGCCA GAACAGCTAG TCCTACTAGA
      ~~~~~~~~~~~~~~~~~~~~~~~~~~~~~~~~~~~~~~~~~~~~~~~~~~~~
      •AspGluGlu HisGlnGlyLeu AlaProAla GluLeuPhe AlaArgLeuLys •
      ~~~~~~~~~~~~~~~~~~~~~~~~~~~~~~~~~~~~~~~~~~~~~~~~~~~~~

14651 GGACGAAGAG CATCAGGGGC TCGCGCCAGC CGAACTGTTC GCCAGGCTCA
      CCTGCTTCTC GTAGTCCCCG AGCGCGGTCG GCTTGACAAG CGGTCCGAGT
      ~~~~~~~~~~~~~~~~~~~~~~~~~~~~~~~~~~~~~~~~~~~~~~~~~~~~
```

-continued

•LAlaArgMet ProAspGly GluAspLeuVal ValThrHis GlyAspAla

14701 AGGCGCGCAT GCCCGACGGC GAGGATCTCG TCGTGACCCA TGGCGATGCC
      TCCGCGCGTA CGGGCTGCCG CTCCTAGAGC AGCACTGGGT ACCGCTACGG

CysLeuProAsn IleMetVal GluAsnGly ArgPheSerGly PheIleAsp •

14751 TGCTTGCCGA ATATCATGGT GGAAAATGGC CGCTTTTCTG GATTCATCGA
      ACGAACGGCT TATAGTACCA CCTTTTACCG GCGAAAAGAC CTAAGTAGCT

•CysGlyArg LeuGlyValAla AspArgTyr GlnAspIle AlaLeuAlaThr •

14801 CTGTGGCCGG CTGGGTGTGG CGGACCGCTA TCAGGACATA GCGTTGGCTA
      GACACCGGCC GACCCACACC GCCTGGCGAT AGTCCTGTAT CGCAACCGAT

•TArgAspIle AlaGluGlu LeuGlyGlyGlu TrpAlaAsp ArgPheLeu

14851 CCCGTGATAT TGCTGAAGAG CTTGGCGGCG AATGGGCTGA CCGCTTCCTC
      GGGCACTATA ACGACTTCTC GAACCGCCGC TTACCCGACT GGCGAAGGAG

ValLeuTyrGly IleAlaAla ProAspSer GlnArgIleAla PheTyrArg •

14901 GTGCTTTACG GTATCGCCGC TCCCGATTCG CAGCGCATCG CCTTCTATCG
      CACGAAATGC CATAGCGGCG AGGGCTAAGC GTCGCGTAGC GGAAGATAGC

•LeuLeuAsp GluPhePhe*** Stop

14951 CCTTCTTGAC GAGTTCTTCT GAGCGGGACT CTGGGGTTCG AAATGACCGA
      GGAAGAACTG CTCAAGAAGA CTCGCCCTGA GACCCCAAGC TTTACTGGCT

15001 CCAAGCGACG CCCAACCTGC CATCACGAGA TTTCGATTCC ACCGCCGCCT
      GGTTCGCTGC GGGTTGGACG GTAGTGCTCT AAAGCTAAGG TGGCGGCGGA

15051 TCTATGAAAG GTTGGGCTTC GGAATCGTTT TCCGGGACGC CGGCTGGATG
      AGATACTTTC CAACCCGAAG CCTTAGCAAA GGCCCTGCG GCCGACCTAC

15101 ATCCTCCAGC GCGGGGATCT CATGCTGGAG TTCTTCGCCC ACCCCGGGAG
      TAGGAGGTCG CGCCCCTAGA GTACGACCTC AAGAAGCGGG TGGGGCCCTC

15151 ATGGGGGAGG CTAACTGAAA CACGGAAGGA GACAATACCG GAAGGAACCC
      TACCCCCTCC GATTGACTTT GTGCCTTCCT CTGTTATGGC CTTCCTTGGG

15201 GCGCTATGAA CGGCAATAAA AAGACAGAAT AAAACGCACG GTGTTGGGTC
      CGCGATACTT GCCGTTATTT TTCTGTCTTA TTTTGCGTGC CACAACCCAG

15251 GTTTGTTCAT AAACGCGGGG TTCGGTCCCA GGGCTGGCAC TCTGTCGATA
      CAAACAAGTA TTTGCGCCCC AAGCCAGGGT CCCGACCGTG AGACAGCTAT

15301 CCCCACCGAG ACCCCATTGG GGCCAATACG CCCGCGTTTC TTCCTTTTCC
      GGGGTGGCTC TGGGGTAACC CCGGTTATGC GGGCGCAAAG AAGGAAAAGG

15351 CCACCCCACC CCCCAAGTTC GGGTGAAGGC CCAGGGCTCG CAGCCAACGT
      GGTGGGGTGG GGGGTTCAAG CCCACTTCCG GGTCCCGAGC GTCGGTTGCA

15401 CGGGGCGGCA AGCCCTGCCA TAGCCACGGG CCCCGTGGGT TAGGGACGGC
      GCCCCGCCGT TCGGGACGGT ATCGGTGCCC GGGGCACCCA ATCCCTGCCG

15451 GGATCGCGGC CC
      CCTAGCGCCG GG

What is claimed is:

1. A non-small cell adenocarcinoma lung cancer cell line that comprises and stably expresses a eukaryotic expression vector comprising the nucleotide sequence of SEQ ID NO:1, which encodes (a) CD80 (B7.1) and (b) an HLA antigen, HLA A1.

2. A method of treating a non-small cell lung cancer in a human subject comprising administering to the subject an effective amount of cells of the non-small cell adenocarcinoma lung cancer cell line of claim 1, wherein the non-small cell lung cancer is not adenocarcinoma.

3. The method of claim 2, wherein the cells of the non-small cell adenocarcinoma lung cancer cell line are administered more than once.

4. The method of claim 2, wherein the-non-small cell lung cancer cell line is allogeneic.

5. The method of claim 2, wherein the non-small cell lung cancer is bronchoalveolar carcinoma and/or squamous cell carcinoma.

6. A method of manufacturing a vaccine against non-small cell lung cancer comprising genetically modifying a non-small cell adenocarcinoma lung cancer cell line to stably expresses a eukaryotic expression vector comprising the nucleotide sequence of SEQ ID NO:1, which encode CD80 (B7.1) and an HLA antigen, HLA A1.

* * * * *

UNITED STATES PATENT AND TRADEMARK OFFICE
CERTIFICATE OF CORRECTION

| | | |
|---|---|---|
| PATENT NO. | : 10,279,020 B2 | Page 1 of 1 |
| APPLICATION NO. | : 14/812416 | |
| DATED | : May 7, 2019 | |
| INVENTOR(S) | : Eckhard R. Podack | |

It is certified that error appears in the above-identified patent and that said Letters Patent is hereby corrected as shown below:

On the Title Page

Item (56) References Cited, OTHER PUBLICATIONS, Page 4, Column 1, Line 43, Toh et al. cite: Please correct "small-cell ung cancer" to read -- small-cell lung cancer --

Item (56) References Cited, OTHER PUBLICATIONS, Page 4, Column 2, Line 3, Borghael et al. cite: Please correct "1527-1639" to read -- 1627-1629 --

In the Claims

Column 98, Line 60, Claim 6: Please correct "encode" to read -- encodes --

Signed and Sealed this
Seventeenth Day of September, 2019

Andrei Iancu
*Director of the United States Patent and Trademark Office*